United States Patent
Blackwell et al.

(10) Patent No.: US 8,367,680 B2
(45) Date of Patent: Feb. 5, 2013

(54) ANTIBACTERIAL SMALL MOLECULES AND METHODS FOR THEIR SYNTHESIS

(75) Inventors: Helen E. Blackwell, Middleton, WI (US); Matthew D. Bowman, Waunakee, WI (US); Joseph R. Stringer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 477 days.

(21) Appl. No.: 12/412,658

(22) Filed: Mar. 27, 2009

(65) Prior Publication Data

US 2009/0270423 A1 Oct. 29, 2009

Related U.S. Application Data

(60) Provisional application No. 61/040,562, filed on Mar. 28, 2008.

(51) Int. Cl.
| | |
|---|---|
| A61K 31/165 | (2006.01) |
| A61K 31/505 | (2006.01) |
| A61K 31/4418 | (2006.01) |
| A61P 31/04 | (2006.01) |
| C07C 235/78 | (2006.01) |
| C07D 213/85 | (2006.01) |
| C07D 239/24 | (2006.01) |
| C40B 30/06 | (2006.01) |

(52) U.S. Cl. ........ 514/256; 514/344; 514/621; 544/242; 546/286; 564/169; 506/10

(58) Field of Classification Search .................. 564/169; 546/286; 544/242
See application file for complete search history.

(56) References Cited

U.S. PATENT DOCUMENTS

| | | |
|---|---|---|
| 3,711,472 A | 1/1973 | Siegrest et al. |
| 3,725,395 A | 4/1973 | Siegrist et al. |
| 3,732,221 A | 5/1973 | Siegrest et al. |
| 3,758,462 A | 9/1973 | Siegrest et al. |
| 3,781,228 A | 12/1973 | Siegrest et al. |
| 3,830,848 A | 8/1974 | Siegrest et al. |
| 3,849,163 A | 11/1974 | Siegrist et al. |
| 4,464,457 A | 8/1984 | Bosse et al. |
| 7,737,164 B2 | 6/2010 | Blackwell et al. |
| 2003/0175988 A1 | 9/2003 | Yarmoluk et al. |
| 2003/0229065 A1 | 12/2003 | Levy et al. |
| 2005/0124678 A1 | 6/2005 | Levy et al. |
| 2007/0128658 A1 | 6/2007 | Blackwell et al. |
| 2007/0184559 A1 | 8/2007 | Yarmoluk et al. |
| 2008/0009528 A1 | 1/2008 | Blackwell et al. |
| 2010/0261763 A1 | 10/2010 | Blackwell et al. |

FOREIGN PATENT DOCUMENTS

| | | |
|---|---|---|
| CH | 539 101 | 8/1973 |
| CH | 542212 | 11/1973 |
| DE | 2 148015 | 4/1972 |

(Continued)

OTHER PUBLICATIONS

Morissette et al. "High-throughput crystallization: polymorphs, salts, co-crystals and solvates of pharmaceutical solids" Advanced Drug Delivery Reviews, 2004, 56, 275-300.*

(Continued)

Primary Examiner — Kortney L Klinkel
(74) Attorney, Agent, or Firm — Greenlee Sullivan P.C.

(57) ABSTRACT

The present invention relates generally to compounds providing antibacterial therapeutic agents and preparations, and related methods of using and making antibacterial compounds. Antibacterial compounds of the present invention include chalcone, alkylpyrimidine, aminopyrimidine and cyanopyridine compounds and derivatives thereof exhibiting minimum inhibitory concentrations (MIC) similar to or less than conventional antibacterial compounds in wide use.

33 Claims, 28 Drawing Sheets

FOREIGN PATENT DOCUMENTS

| | | |
|---|---|---|
| DE | 32 32 620 | 3/1984 |
| EP | 0 062 467 | 10/1982 |
| EP | 0 659 582 | 6/1995 |
| EP | 1 308 728 | 5/2003 |
| JP | 56 004781 | 1/1981 |
| JP | 4-279568 A | 10/1992 |
| JP | 2002-8862 | 1/2002 |
| NL | 6615211 | 5/1967 |
| WO | WO 98/15532 | 4/1998 |
| WO | WO 2004/046103 | 6/2004 |
| WO | WO 2006/084056 | 8/2006 |
| WO | WO 2008/016738 | 2/2008 |

OTHER PUBLICATIONS

Seddon et al. "Pseudopolymorph: A Polemic" Crystal Growth and Design, 2004, 4, 1087.*
Vippagunta et al. "Crystalline solids" Advanced Drug Delivery Reviews, 2001, 48, 3-26.*
Braga et al. "Making crystals from crystals: a green route to crystal engineering and polymorphism" Chem. Commun. 2005, 3635-3645.*
Palanowski et al. ("Synteza Zwiazkow O Spodziewanym Dzialanium Na Uklad Krazenia" Acta Poloniae Pharmaceutica, 1967, 24(6), 567-74).*
Palanowski et al. ("Synthesis of potential vasoactive compounds. I. Phenylacrylophenone Derivatives" Acta Poloniae Pharmaceutica (English Translation), 1967, 24(6), 567-74, accessed via SciFinder® Jun. 30, 2011.*
Palanowski et al. "Synthesis of Compounds with Action Expected Upon the Circulatory System; Part I: Derivatives of Phenylacrylophenone" Acta Poloniae Pharmaceutica, 1967, 24(6), p. 567-74, certified English translation p. 1-13.*
Hafez, A.A. A. et al. (1992) Nitriles in Heterocyclic Synthesis. Part III: New Sulpha Drugs related to Cyanopyridine Derivatives, J. Chem. Tech. Biotechnology 55:333-338.
Stringer, J.R. et al. (Jan. 6, 2011) "Improved Small-Molecule Macroarray Platform for the Rapid Synthesis and Discovery of Antibacterial Chalcones," ACS Combinatorial Science 13(2):175-180.
Stringer, J.R. et al. (Mar. 17, 2011) Correction to Improved Small-Molecule Macroarray Platform for the Rapid Synthesis and Discovery of Antibacterial Chalcones, ACS Combinatorial Science 13(3):345.
Stringer et al. (Jan. 29, 2007) "Rapid Identification of Antibacterial Agents Effective Against *Staphylococcus aureus* Using Small-Molecule Macroarrays," Abstract for Poster Presentation at the American Chemical Society Meeting held in Chicago IL (USA) Mar. 2007.
Stringer et al. "Rapid Identification of Antibacterial Agents Effective Against *Staphylococcus aureus* Using Small-Molecule Macroarrays," Poster Presentation at the American Chemical Society Meeting held in Chicago IL (USA) presented Mar. 28, 2007.
Andrews, J.M. (2001) "Determination of Minimum Inhibitory Concentrations," *J. Antimicrob. Chemother*. 48(Supp. 1):5-16.
Ansari et al. (2005) "Combinatorial Synthesis and Antibacterial Evaluation of an Indexed Chalcone Library," *Chem. Biodiv*. 2:1656-1664.
Bailey et al. (1973) "Synthesis and Some Properties of Dyes Containing the Pyrano[2,3-d]pyrimidine Nucleus," *J. Chem. Soc. Perkin Trans 1: Organic Bio-Organic Chem*. 8:823-828.
Balasubramanian, S. (2001) "Solid Phase Chemical Technologies for Combinatorial Chemistry," *J. Cell. Biochem*. :28-33.
Bannwarth, W. (2000) "Solid Phase Chemistry. Linkers for Solid-Phase Organic Synthesis (SPOS) and Combinatorial Approaches on Solid Support," In; *Methods and Principles in Medicinal Chemistry*, vol. 9, *Combinatorial Chemistry a Practical Approach*, Bannwarth et al. Eds., Ch. 3, pp. 47-98.
Barnick et al. (1979) "A Convenient Direct Method for the Preparation of β-Keto-Acids," *Synthesis* 79:787-788.
Bassler et al. (Apr. 21, 2006) "Bacterially Speaking," *Cell* 125:237-246.
Bassler et al. (1995) "Intracellular Communication in Marine *Vibrio* Species: Density-Dependent Regulation of the Expression of Bioluminescence," In; *Two Component Signal Transduction*, Hoch et al. Eds., Am. Soc. Microbiol., Washington D.C., pp. 431-435.
Bassler et al. (1993) "Intercellular Signaling in *Vibrio harveyi*: Sequence and Function of Genes Regulating Expression of Luminescence," *Mol. Microbiol*. 9(4):773-786.
Bassler et al. (1994) "Multiple Signaling Systems Controlling Expression of Luminescence in *Vibrio Harvey*: Sequence and Function of Genes Encoding a Second Sensory Pathway," *Mol. Micobiol*. 13(2):273-286.
Bauer et al. (1966) "Antibiotic Susceptibility Testing by a Standardized Single Disk Method," *Tech Bull. Reg. Med. Technologists* 36(3):49-52.
Behrendt et al. (1999) "Photomodulation of the Conformation of Cyclic Peptides with Azobenzene Moieties in the Peptide Backbone," *Angew. Chem. Int. Ed. Engl*. 38(18):2771-2774.
Bernatowicz et al. (1989) "An Efficient Method for Racemization Free Attachment of 9-Fluorenylmethyloxycarbonyl-Amino Acids to Peptide-Synthesis Supports," *Tetrahedron Lett*. 30(33):4341-4344.
Blackwell et al. (2003) "Out of the Oil Bath and into the Oven—Microwave-Assisted Combinatorial Chemistry Heats Up," *Org. Biomol. Chem*. 1:1251-1555.
Blackwell, H.E. (2006) "Hitting the SPOT: Small-Molecule Macroarrays Advance Combinatorial Synthesis," *Curr. Opin. Chem. Biol*. 10:203-212.
Bowden et al. (1990) "Structure-Activity Relations. Part 5. Antibacterial Activity of a Series of Substituted (*E*)-3-(4-Phenyl benzoyl)acrylic Acids, -Chalcones, -2-Hydroxychalcones and -α-Bromochalcones; Addition of Cyteine to Substitutes 3-Benzoylacrylic Acids and Related Compounds," *J. Chem. Res*. (*M*) :377.
Bowden et al. (1979) "Structure-Activity Relations. Part 4. Reactivity and Anti-Bacterial Activity of 3-Aroylacrylic Acids and Their Methyl Esters," *J. Chem. Res*. (*S*) 8.
Bowman et al. (Web Release Mar. 18, 2006) "Discovery of Fluorescent Cyanopyridine and Deazalumazine Dyes Using Small Molecule Macroarrays," *Org. Lett*. 8:1645-1648.
Bowman et al. (Web Release Mar. 31, 2006) "Efficient Synthesis of Small Molecule Macroarrays: Optimization off the Macroarray Synthesis Platform and Examination of Microwave and Conventional Heating Methods," *Tetrahedron* 62:4715-4727.
Bowman et al. (Web Release May 18, 2004) "Microwave-Accelerated SPOT-Synthesis on Cellulose Supports," *Org. Lett*. 6:2019-2022.
Bowman et al. (Apr. 2007) "Rapid Identification of Antibacterial Agents Effective Against *Staphylococcus aureus* Using Small-Molecule Macroarrays," *Chem. Biol*. 14:351-357.
Brown et al. (Jan. 14, 2005) "New Targets and Screening Approaches in Antimicrobial Drug Discovery," *Chem. Rev*. 105:759-774.
Bundgaard et al. (1992) "(C) Means to Enhance Penetration: (1) Prodrugs as a Means to Improve the Delivery of Peptide Drugs," *Adv. Drug Deliv. Rev*. 8(1):1-38.
Bundgaard, H.(1991) "Design and Application of Prodrugs," In; *A Textbook of Drug Design and Development*, Krosgaard-Larsen et al. Eds., Ch. 5, pp. 113-191.
Carpino et al. (1972) "9-Fluorenylmethoxycarbonyl Amino-Protecting Group," *J. Org. Chem*. 37(22):3404-3409.
Coates et al. (Nov. 2002) "The Future Challenges Facing the Development of New Antimicrobial Drugs," *Nat. Rev. Drug Disc*. 1:895-910.
Cohen et al. (Jan. 25, 2005) "A Fluorescent Probe Designed for Studying Protein Conformational Change," *Proc. Nat. Acad. Sci. USA* 102(4):965-970.
Constable et al. (1994) "4-*tert*-butylphenyl Solubilized Oligopyridines," *Tetrahedron* 50(26):7799-7806.
Del Carmen et al. (1973) "2,4,6-Trisubstituted Pyrdidines. Synthesis, Fluorescence, and Scintillator Properties," *J. Am. Chem. Soc*. 95(15):4891-4895.
Dobaria et al. (Sep. 2002) "Synthesis and antimicrobial screening of cyanopyridines," *J. Indian Chem. Soc*. 79:772-773.
Eberhard et al. (1986) "Analogs of the Autoinducer of Bioluminescence in Vibrio fischeri," *Arch. Microbiol*. 146:35-40.
Eberhard et al. (2000) "Chemical Synthesis of Bacterial Autoinducers and Analogs," *Methods Enzymol*. 305:301-315.

Elagamey, A. G. A.. et al. (1990) "Nitriles in Heterocyclic Synthesis: A Novel Route for the Synthesis of Naphthodipyrans, Pyridines, 2H- and 4-H-Pyrans," Collect. Czech. Chem. Commun. 55:524-534.

Epand et al. (Web Release Jul. 3, 2004) "Antimicrobial 14-Helical Beta-Peptides: Potent Bilayer Disrupting Agents," *Biochemistry* 43:9527-9535.

Fleming et al. (Nov. 13, 1995) "Chemical Reagents in Photoaffinity Labeling," *Tetrahedron* 51(46):12479-12520.

Frank, R. (1992) "Spot-Synthesis—An Easy Technique for the Positionally Addressable, Parallel Chemical Synthesis on a Membrane Support," *Tetrahedron* 48(42):9217-9232.

Frank R.J. (2002) "The SPOT-Synthesis Technique: Synthetic Peptide Arrays on Membrane Supports—Principles and Applications," *J. Immunol. Methods.* 267:13-26.

Fray et al. (Oct. 1999) "Plants Genetically Modified to Prodice N-acylhomoserine Lactones Communicate with Bacteria," *Nat. Biotechnol.* 17:1017-1020.

Frezza et al. (Web Release Mar. 29, 2006) "Synthesis and Biological Evaluation of Homoserine Lactone Derived Ureas as Antafonists of Bacterial Quorum Sensing," *Bioorg. Med. Chem.* 14:4781-4791.

Fuqua et al. (2002) "Listening in on Bacteria: Acyl-Homoserine Lactone Signaling," *Nat. Rev. Mol. Cell Biol.* 3:685-695.

Fuqua et al. (Sep. 2001) "Regulation of Gene Expression by Cell-to-Cell Communication: Acyl-Homoserine Lactone Quorum Sensing," *Ann. Rev. Genet.* 35:439-468.

Gafner et al. (1996) "Antifungal and Antibacterial Chalcones from *Myrica serrata,*" *Planta Med.* 62:67-69.

Ganesan et al. (Jan. 2002) "Recent Developments in Combinatorial Organic Synthesis," *Drug Disc. Today* 7(1):47-55.

Grosche et al. (1999) "Pyrazole, Pyridine and Pyridone Synthesis on Solid Support," *Synthesis* 11:1961-1970.

Hensler et al. (Web Release Aug. 4, 2006) "Pyrrolidine Bis-Cyclic Guanidines with Antimicrobial Activity Against Drug-Resistant Gram-Positive Pathogens Identified from a Mixture-Based Combinatorial Library," *Bioorg. Med. Chem. Lett.* 16:5073-5079.

Hilpert et al. (Aug. 2005) "High-Throughput Generation of Small Antibacterial Peptides with Improved Activity," *Nature Biotechnol.* 23(8):1008-1012.

International Search Report and Written Opinion, Corresponding to International Application No. PCT/US2007/069069, Mailed Nov. 17, 2008.

International Preliminary Report on Patentability, Corresponding to International Application No. PCT/US2007/069069, Issued Dec. 16, 2008.

James, I.W. (1999) "Linkers for Solid Phase Organic Synthesis," *Tetrahedron* 55:4855-4946.

Jun et al. (Web Release Jan. 17, 2007) "Synthesis and Evaluation of 2',4',6'-Trihydroxychalcones as a New Class of Tyrosinase Inhibitors," *Bioorg. Med. Chem.* 15:2396-2402.

Kappe, C.O. (2004) "Controlled Microwave Heating in Modern Organic Synthesis," *Angew Chem. Int. Ed.* 43:6250-6284.

Kappel et al. (Web Release Nov. 2, 2005) "A Convenient Orthogonally Cleavable Methionine Handle for Anchoring Amines to Polymeric Supports," *J. Comb. Chem.* 7:78-84.

Koch et al. (2005) "The LuxR Receptor: The Sites of Interaction with Quorum-Sensing Signals and Inhibitors," *Microbiology* 151:3589-3602.

Krohnke, F. (1976) "The Specific Synthesis of Pyridines and Oligopyridines," *Synthesis* :1-24.

Kromann et al. (Web Release Sep. 21, 2004) "Synthesis of Prenylated Benzaldehydes and Their use in the Synthesis of Analogues of Licochalcone A," *Eur. J. Med. Chem.* 39:993-1000.

Larsen et al. (Web Release Sep. 8, 2005) "Conformationally Restricted Anti-Plasmodial Chalcones," *Bioorg. Med. Chem. Lett.* 15:4858-4861.

Lawrence et al. (Web Release Sep. 1, 2006) "Effects of $\alpha$-Substitutions on Structure and Biological Activity of Anticancer Chalcones," *Bioorg Med. Chem. Lett.* 16:5844-5848.

Lee et al. (Web Release Nov. 9, 2005) "Activity of Purified QscR, a *Pseudomonas aeruginosa* Orphan Quorum-Sensing Transcription Factor," *Mol. Microbiol.* 59:602-609.

Ley et al. (Aug. 2002) "New Tools and Concepts for Modern Organic Synthesis," *Nat. Rev. Drug. Discov.* 1(8):573-586.

Li et al. (2004) "Solid-Phase Synthesis of Styryl Dyes and Their Applications as Amlyloid Sensors," *Angew Chem. Int. Ed.* 43:6331-6335.

Lin et al. (2006) "Rapid Synthesis of Diketopiperazine Macroarrays Via Ugi Four-Component Reactions on Planar Solid Supports," *Chem. Commun.* :2884-2886.

Lin et al. (Web Release Sep. 3, 2005) "Small Molecule Macroarray Construction Via Ugi Four-Component Reactions," *Org. Lett.* 7(20):4455-4458.

Marzinzik et al. (Web Release Jan. 22, 1998) "Key Intermediates in Combinatorial Chemistry: Access to Various Heterocycles from $\alpha,\beta$-Unsaturated Ketones on the Solid Phase," *J. Org. Chem.* 63:723-727.

Matsui et al. (1992) "Synthesis and Characterization of Fluorescent 4,6-Disubstituted3-cyano-2-Methylpyridines," *J. Chem. Soc. Perk. Trans.* 2:201-206.

Mello et al. (2001) "Dual-Signaling Fluorescent Chemosensors Based on Conformational Restriction and Induced Charge Transfer," *Angew. Chem. Int. Ed.* 40(8):1536-1538.

Mello et al. (2005) "Reversing the Discovery Paradigm: A New Approach to the Combinatorial Discovery of Fluorescent Chemosensors," *J. Am. Chem. Soc.* 127:10124-10125.

Misra et al. (1971) "Studies in Potential Germicides: Part VII, Syntheses of Napthalene and Phenanthrene Analogues of Chalcones" 34(6):260-264.

Modzelewska et al. (Web Release Jan. 24, 2006) "Anticancer Activities of Novel Chalcone and Bis-Chalcone Derivatives," *Biorg. Med. Chem.* 14:3491-3495.

Navre et al. (1998) "Application of Combinatorial Chemistry to Antimicrobial Drug Discovery," *Exp. Opin. Invest. Drugs* 7(8):1257-1269.

Ni et al. (2004) "Recent Advances in Therapeutic Chalones," *Exp. Opin. Ther. Patents* 14(12):1669-1691.

Nielsen et al. (2004) "Antibacterial Chalcones-Bioisoteric Replacement of the 4'-Hydroxy Group," Mioorg. Med. Chem. 12:3047-3054.

Nicolaou et al. (2001) "Discovery of Novel Antibacterial Agents Against Methicillin-Resistant *Staphylococcus aureus* from Combinatorial Benzopyran Libraries," *ChemBioChem.* 2(6):460-465.

Nielsen et al. (Web Release Mar. 4, 2005) "Cationic Chalcone Antibiotics. Design, Synthesis, Mechanism of Action," *J. Med. Chem.* 48:2667-2677.

Nielsen et al. (Apr. 1988) "Glycolamide Esters as Biolable Prodrugs of Carboxylic Acid Agents: Synthesis, Stability, Bioconversion, and Physiocochemical Properties," *J. Pharm. Sci.* 77(4):285-298.

Nogrady (1985) "Pro-Drugs and Soft Drugs," In; *Medicinal Chemistry A Biochemical Approach*, Oxford Press, New York, pp. 388-392.

Notari, R.E. (1985) "Theory and Practice of Prodrug Kinetics," *Methods Enzymol.* 112:309-323.

Powers et al. (1998) "Automated Parallel Synthesis of Chalcone-Based Screening Libraries," *Tetrahedron* 54:4085-4096.

Rajvaidya S. et al. (Apr., 2004) "Synthesis and Microbiological Activities of Some Pyrazolines and Cyanopyridines," *Ind. J. Chem.* 43B:906-908.

Rathke et al (Oct. 1985) "Synthesis of $\beta$-Keto Acids and Methyls Ketones Using *Bis* (trimethylsily) Malonate and Triethylamine in the Presence of Lithium or Magnesium Hal ides," *Synth. Commun.* 15(12):1039-1049.

Rink et al. (1987) "Solid-Phase Synthesis of Protected Peptide Fragments Using a Trialkoxy-Diphenyl-Methyl Ester Resin," *Tetrahedron Lett.* 28(33):3787-3790.

Rubin et al. (Jan.-Mar. 1999) "The Economic Impact of *Staphylococcus aureus* Infection in New York City Hospitals," *Emerg. Infect. Dis.* 5(1):9-17.

Scharn et al. (Web Release May 26, 2000) "Spatially Addressed Synthesis of Amino-and Amino-Oxy-Substituted 1,3,5-Trizine Arrays on Polymeric Membranes," *J. Comb. Chem.* 2:361-369.

Schena et al. (Oct. 20, 1995) "Quantitative Monitoring of Gene Expression Patterns with a Complementary DNA Microarray," *Science* 270:467-470.

Schiedel et al. (2001) "Single-Compound Libraries of Organic Materials: Parallel Synthesis and Screening of Fluorescent Dyes," *Angew Chem. Int. Ed.* 40(24):4677-4680.

Schmitt et al. (2004) "Unexpected Relationships Between Structure and Function in Alpha-, Beta-Peptides: Antimicrobial Foldamers with Heterogenous Backbones," *J. Am. Chem. Soc.* 126:6848-3849.

Schmitt et al. (2007) "Interplay Among Folding, Sequence, and Pipophilicity in the Antibacterial and Hemolytic Activities of Alpha/Beta—Peptides," *J. Am. Chem. Soc.* 129:417-428.

Schultz et al. (2003) "Mechanism and Dynamics of Azobenzene Photoisomerization," *J. Am. Chem. Soc.* 125(27):8098-8099.

Seneci et al. (2000) "Combinatorial Chemistry and High-Throughput Screening in Drug Discovery: Different Strategies and Formats," *Mol. Diversity* 5:75-89.

Shi et al. (Web Release Jul. 6, 2005) "Solid-Phase Synthesis and Anti-Infective Activity of a Combinatorial Library Based on the Natural Product Anisomycin," *Bioorg. Med. Chem. Lett.* 15:4151-4154.

Silen et al. (Jun. 1998) "Screening for Novel Antimicrobials from Encoded Combinatorial Libraries by Using a Two-Dimensional Agar Format," *Antimicrob Agents Chem.* 42(6):1447-1453.

Sivakumar et al. (Web Release Jan 12, 2007) "Synthesis, Antimycobacterial Activity Evaluation, and QSAR Studies of Chalone Derivatives," *Bioorg. Med. Chem. Lett*, 17:1695-1700.

Strøm et al. (Apr. 24, 2003) "The Pharmacophore of Short Cationic Antibacterial Peptides," *J. Med. Chem.* 46(9):1567-1570.

Sun et al. (Web Release Oct. 24, 2005) "Slid-Phase Synthesis Development of a Thymidinyl and 2'-deoxyuridinyl Ugi Library for Anti-Bacterial Agent Screening," *Tetrahedron Lett.* 46:8497-8501.

Tsiodras et al. (Jul. 21, 2001) "Linezolid Resistance in a Clinical Isolate of *Staphylococcus aureus*," *Lancet* 358:207-208.

Tu et al. (2005) "An Efficient Improve for the Kröhnke Reaction: One-Pot Synthesis of 2,4,6-Triarylpyridines Using Raw Materials Under Microwave Irradiation," *Chem. Lett.* 34(5):732-733.

Uttamchandani et al. (Web Release Jan. 8, 2005) "Small Molecule Microarrays: Recent Advances and Applications," *Curr. Opin. Chem. Biol.* 9:4-13.

Weiss et al. (Jan. 5, 1952) "Acetic Acid-Ammonium Acetate Reactions. An Improved Chichibabin Pyridine Synthesis," *J. Am. Chem. Soc.* 74:200-202.

Yamaguchi Y. et al. (Jul.-Aug. 1998) "A New Expedient Route to 2,6-diaryl-3-cyano-4-(trifluoromethyl) Pyridines," *J. Heterocyclic Chem.* 35:805-809.

Yu et al. (Web Release Apr. 3, 2002) "Solid Supports for Combinatorial Chemistry," *Curr. Opin. Chem. Biol.* 6:347-352.

Zasloff, M. (Jan. 24, 2002) "Antimicrobial Peptides of Multicellular Organisms," *Nature* 415:389-395.

Zimmerman et al. (1989) "Rigid Molecular Tweezers: Preorganized Hosts for Electron Donor-Acceptor Complexation in Organic Solvents," *J. Am. Chem. Soc.* 111(4):1373-1381.

Bowden et al. (1990) "Structure-Activity Relations. Part 5. Antibacterial Activity of a Series of Substituted (*E*)-3-(4-Phenyl benzoyl)acrylic Acids, -Chalcones, -2-Hydroxychalcones and -α-Bromochalcones; Addition of Cyteine to Substitutes 3-Benzoylacrylic Acids and Related Compounds," *J. Chem. Res. (M)* 2801-2830.

* cited by examiner

Small molecule macroarray construction using a Rink linker
(a) Acetyl-phenoxyacetic acid (A-F, see Figure 4), DIC, DMF;
(b) Benzaldehydes (1-29, see Figure 4), NaOH, EtO:H2O(1:1), (3x);
(c) Acetamide- or guanidine-HCl, KotBu, DMA;
(d) cleavage: TFA vapor;
(e) 3-aminocrontonitrile, KOH, EtOH.

Can be any primary amine or diamine with one amine protected $R_A$ and $R_B$ represent one or more optional non-hydrogen substituents

* OH group can be attached at any ring carbon

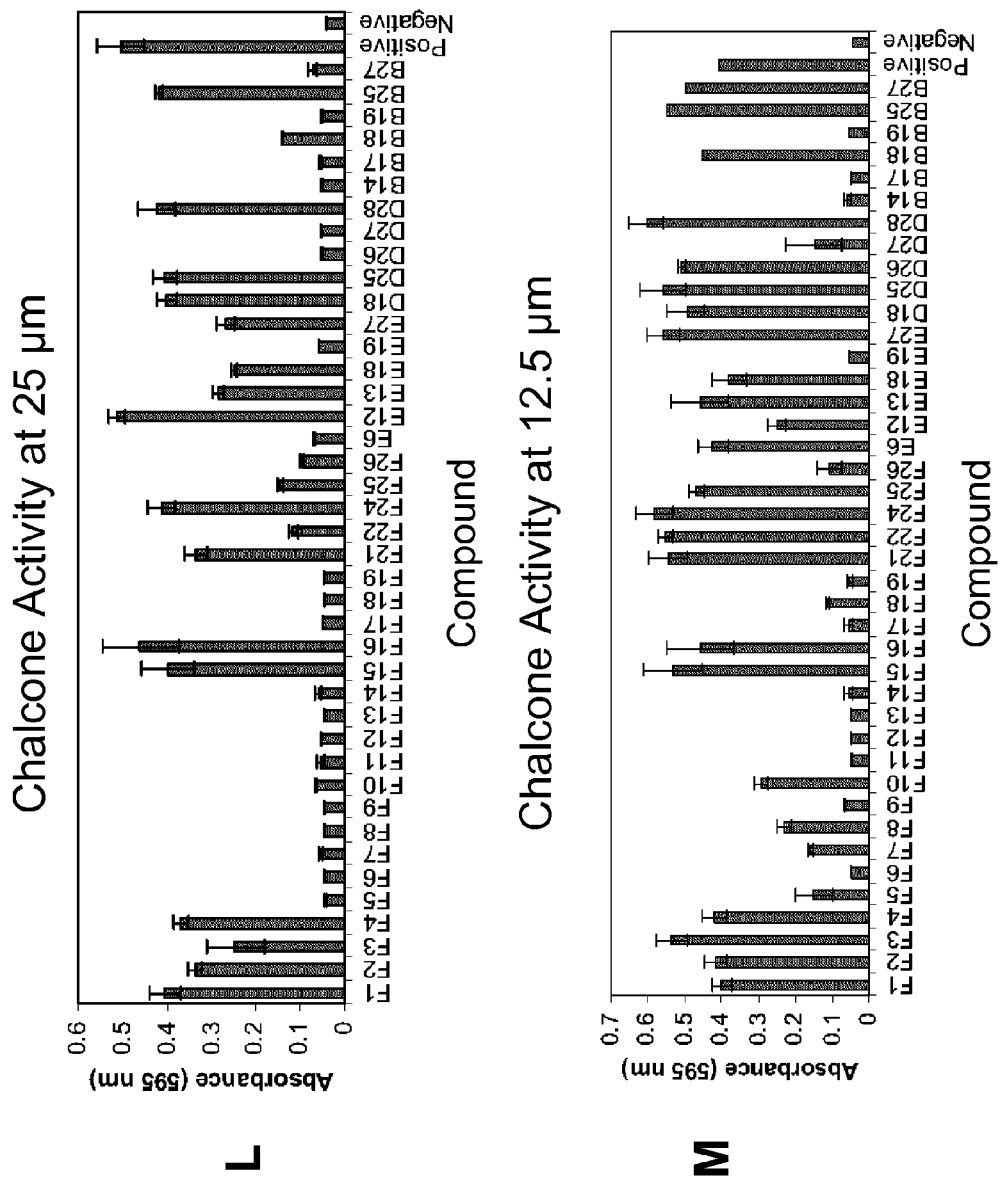

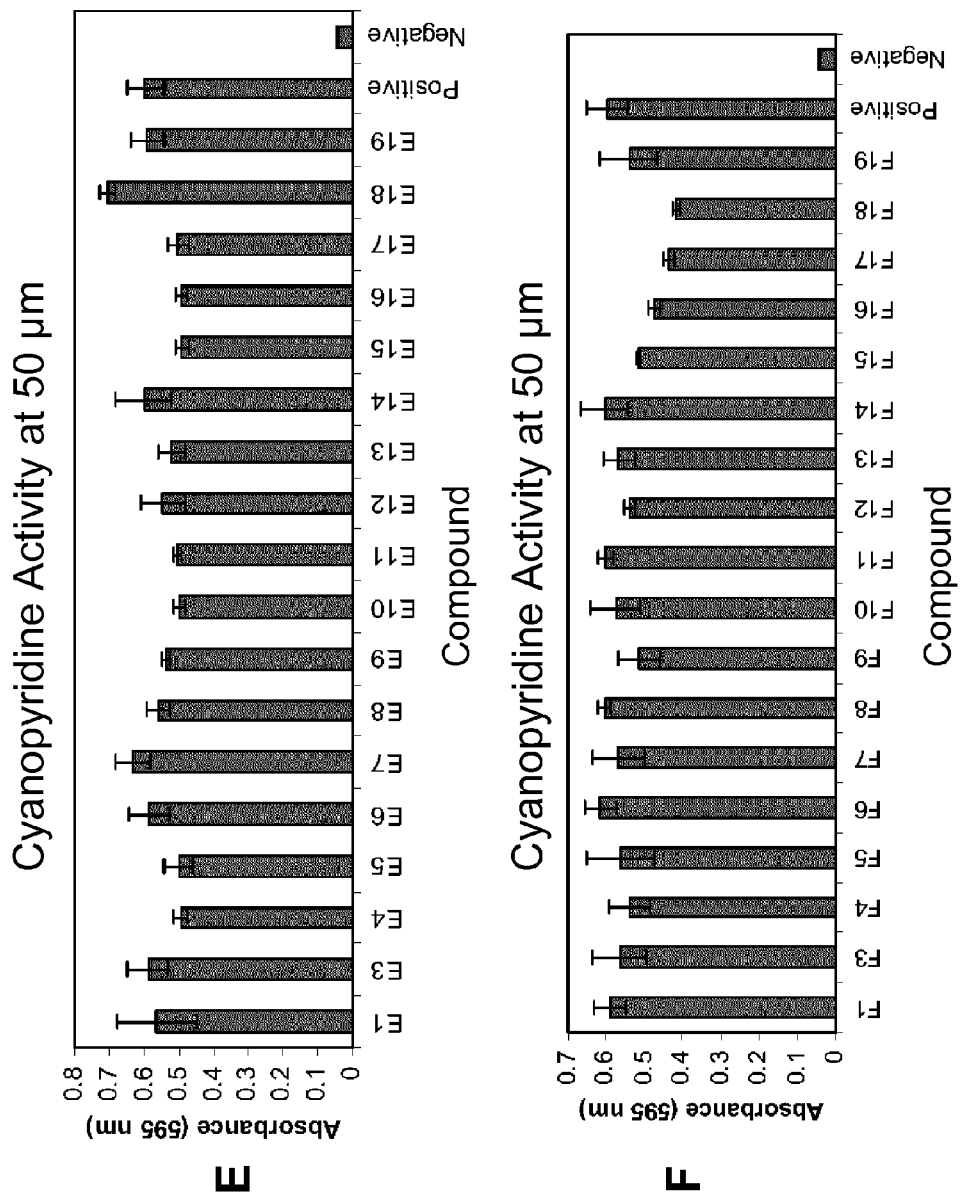

ANTIBACTERIAL SMALL MOLECULES AND METHODS FOR THEIR SYNTHESIS

CROSS-REFERENCE TO RELATED APPLICATIONS

This application claims priority under 35 U.S.C. §119(e) to U.S. Provisional Patent Application 61/040,562, filed Mar. 28, 2008, which is hereby incorporated by reference in its entirety.

STATEMENT REGARDING FEDERALLY SPONSORED RESEARCH OR DEVELOPMENT

This invention was made with United States government support awarded by the following agencies: National Science Foundation Grant CHE-0449959. The United States government has certain rights in the invention.

BACKGROUND OF INVENTION

The emergence of resistant bacterial strains without the increased development of new antibiotic structure classes constitutes a serious medical crisis. Brown, E. D.; Wright, G. D. *Chem. Rev.* 2005, 105, 759-774; Coates, A.; Hu, Y.; Bax, R.; Page, C. *Nat. Rev. Drug Discovery* 2002, 1, 895-910. Infection with the common pathogen *Staphylococcus aureus* has been estimated to double the cost, length of stay, and the even death rate in New York City hospitals. Rubin, R. J.; Harrington, C. A.; Poon, A.; Dietrich, K.; Greene, J. A.; Moiduddin, A. *Emerging Infectious Diseases* 1999, 5, 9-17. Designing antibiotics that treat bacterial infections is a constant struggle for synthetic chemists and biologists because bacteria have an extraordinary ability to adapt and develop resistance to new antibacterial agents. For example, the most recent antibiotic, Linezolid, was released on the market in 2000, only to have cases of Linezolid-resistant bacteria reported the following year. This was alarming news, because Linezolid is a member of the oxazolidinone family, a structure class that had never previously been used as a scaffold for antibacterial agents. This development underscores the need for the discovery of new structural scaffolds with antibacterial activity.

Combinatorial chemistry continues to play an important role in advancing the chemical biology and drug discovery fields. Navre, M., Application of combinatorial chemistry to antimicrobial drug discovery. *Expert Opin. Invest. Drugs* 1998, 7, 1257-1269; Seneci, P.; Miertus, S., Combinatorial chemistry and high-throughput screening in drug discovery: Different strategies and formats. *Mol. Diversity.* 2000, 5, 75-89. One of the main advantages of combinatorial chemistry is the ability to generate a large, diverse library of compounds using a minimum amount of reagents in a relatively short amount of time. Because a combinatorial approach can generate a large number of compounds, this makes it ideal for probing and studying biological targets.

Solid-phase chemistry has taken on a major role in advancing combinatorial chemistry. Ganesan, A., Recent developments in combinatorial organic synthesis. *Drug Discovery Today* 2002, 7, 47-55; Balasubramanian, S., Solid phase chemical technologies for combinatorial chemistry. *J. Cell. Biochem.* 2001, 28-33; Bannwarth, W., Solid phase chemistry. Linkers for solid-phase organic synthesis (SPOS) and combinatorial approaches on solid support. *Methods Princ. Med. Chem.* 2000, 9, 47-98. Traditional solid phase techniques employ hydrophobic polymeric supports, such as polystyrene beads. Yu, Z. R.; Bradley, M., Solid supports for combinatorial chemistry. *Curr. Opin. Chem. Biol.* 2002, 6, 347-352. Although these solid supports offer advantages, including rapid and easy compound purification, there are some disadvantages. The hydrophobic nature of polystyrene beads is not compatible with many reactions that require the use of aqueous or certain polar solvents. Recently, the implementation of small molecule macroarrays in combinatorial chemistry has lead to an improved ability to perform both on- and off-support biological assays. Blackwell, H. E., Hitting the SPOT: small-molecule macroarrays advance combinatorial synthesis. *Curr. Opin. Chem. Biol.* 2006, 10, 203-212; Bowman, M. D.; Jacobson, M. M.; Blackwell, H. E., Discovery of fluorescent cyanopyridine and deazalumazine dyes using small molecule macroarrays. *Org. Lett.* 2006, 8, 1645-1648; Bowman, M. D.; Jacobson, M. M.; Pujanauski, B. G.; Blackwell, H. E., Efficient synthesis of small molecule macroarrays: optimization of the macroarray synthesis platform and examination of microwave and conventional heating methods. *Tetrahedron* 2006, 62, 4715-4727; Lin, Q.; Blackwell, H. E., Rapid synthesis of diketopiperazine macroarrays via Ugi four-component reactions on planar solid supports. *Chem. Commun.* 2006, 2884-2886.

Solid phase synthesis requires a linker to attach or "link" a synthesized substrate to an insoluble support. A variety of linkers have been used in solid phase synthesis, with two of the most widely used being the Wang and Rink linkers. James, I. W., Linkers for solid phase organic synthesis. *Tetrahedron* 1999, 55, 4855-4946. These two acid labile linkers are advantageous for synthesis because they can be cleaved with relatively mild acids in a short period of time.

Small molecule macroarrays can be traced back to the origins of the SPOT-synthesis technique. Frank, R., Spot-Synthesis—an Easy Technique for the Positionally Addressable, Parallel Chemical Synthesis on a Membrane Support. *Tetrahedron* 1992, 48, 9217-9232. Frank originally designed the SPOT-synthesis technique for the construction of peptide libraries as an alternative to standard solid phase peptide synthesis approaches (i.e. the use of polystyrene beads). Using the SPOT technique individual polypeptides can be synthesized in a spatially addressed format, and the resulting polypeptide arrays can be used in a variety of on support biological assays.

The generation of small molecule macroarrays involves the use of a planar cellulose support for library construction. This cellulose support is readily accessible laboratory filter paper, an inexpensive alternative to other solid-phase supports. A variety of organic compounds can be used as building blocks for constructing arrays of small molecules. Recently, Blackwell et al. has constructed small molecule macroarrays utilizing multi-component reactions, and microwave irradiation to construct libraries of heterocylces, chalcones, diketopiperazines, and fluorescent cyanopyridine and deazalumazine dyes. Bowman, M. D.; Jeske, R. C.; Blackwell, H. E., Microwave-accelerated SPOT-synthesis on cellulose supports. *Org. Lett.* 2004, 6, 2019-2022; Lin, Q.; O'Neill, J. C.; Blackwell, H. E., Small molecule macroarray construction via Ugi four-component reactions. *Org. Lett.* 2005, 7, 4455-4458; Bowman, M. D.; Jacobson, M. M.; Blackwell, H. E., Discovery of fluorescent cyanopyridine and deazalumazine dyes using small molecule macroarrays. *Org. Lett.* 2006, 8, 1645-1648; Bowman, M. D.; Jacobson, M. M.; Pujanauski, B. G.; Blackwell, H. E., Efficient synthesis of small molecule macroarrays: optimization of the macroarray synthesis platform and examination of microwave and conventional heating methods. *Tetrahedron* 2006, 62, 4715-4727. Small molecule macroarrays have advantages over traditional solution-phase synthesis, as several hundred compounds can be synthesized in high purity and screened for biological activity in a few days using a minimal amount of reagents, for example as illustrated in FIG. 1.

Application of a combinatorial approach to the identification of antibacterial agents permits the generation of diverse arrays of compounds that can be screened for antibacterial activity. Several new antibacterial agents have been identified in combinatorial libraries using a variety of screening techniques, including pyrrolidine bis-cyclic guanidines, hydrazinyl urea-based compounds, benzopyrans, thymidinyl derivatives, and natural product derivatives, and certain 1,3-diphenyl-2-propen-1-ones (chalcones). Hensler, M. E.; Bernstein, G.; Nizet, V.; Nefzi, A., Pyrrolidine bis-cyclic guanidines with antimicrobial activity against drug-resistant Gram-positive pathogens identified from a mixture-based combinatorial library. *Bioorg. Med. Chem. Lett.* 2006, 16, 5073-5079; Nicolaou, K. C.; Roecker, A. J.; Barluenga, S.; Pfefferkorn, J. A.; Cao, G. Q., Discovery of novel antibacterial agents active against methicillin-resistant *Staphylococcus aureus* from combinatorial benzopyran libraries. *Chembiochem* 2001, 2, 460-465; Sun, D.; Lee, R. E., Solid-phase synthesis development of a thymidinyl and 2'-deoxyuridinyl Ugi library for anti-bacterial agent screening. *Tetrahedron Lett.* 2005, 46, 8497-8501; Shi, S.; Zhu, S.; Gerritz, S. W.; Esposito, K.; Padmanabha, R.; Li, W.; Herbst, J. J.; Wong, H.; Shu, Y. Z.; Lam, K. S.; Sofia, M. J., Solid-phase synthesis and anti-infective activity of a combinatorial library based on the natural product anisomycin. *Bioorg. Med. Chem. Lett.* 2005, 15, 4151-4154; Ansari, F. L.; Nazir, S.; Noureen, H.; Mirza, B., Combinatorial synthesis and antibacterial evaluation of an indexed chalcone library. *Chem. Biodiv.* 2005, 2, 1656-1664.

Chalcones are small molecule natural products found in a variety of plants that exhibit a wide range of biological activities. Kromann, H.; Larsen, M.; Boesen, T.; Schonning, K.; Nielsen, S. F., Synthesis of prenylated benzaldehydes and their use in the synthesis of analogues of licochalcone A. *Eur. J. Med. Chem.* 2004, 39, 993-1000; Jun, N.; Hong, G.; Jun, K., Synthesis and evaluation of 2',4',6'-trihydroxychalcones as a new class of tyrosinase inhibitors. *Bioorg. Med. Chem.* 2007, 15, 2396-2402; Lawrence, N. J.; Patterson, R. P.; Ooi, L.-L.; Cook, D.; Ducki, S., Effects of α-substitutions on structure and biological activity of anticancer chalcones. *Bioorg. Med. Chem. Lett.* 2006, 16, 5844-5848; Modzelewska, A.; Pettit, C.; Achanta, G.; Davidson, N. E.; Huang, P.; Khan, S. R., Anticancer activities of novel chalcone and bis-chalcone derivatives. *Bioorg. Med. Chem.* 2006, 14, 3491-3495.

Certain chalcones exhibit antimicrobial activity. Sivakumar, P. M.; Seenivasan, S. P.; Kumar, V.; Doble, M., Synthesis, antimycobacterial activity evaluation, and QSAR studies of chalcone derivatives. *Bioorg. Med. Chem. Lett.* 2007, 17, 1695-1700; Gafner, S.; Wolfender, J.-L.; Mavi, S.; Hostettmann, K., Antifungal and antibacterial chalcones from *Myrica serratia. Planta Med.* 1996, 62, 67-9. Naturally-occurring chalcones (shown below) are generally lipophilic and have moderate antibacterial activity. There have been solution-phase synthetic efforts directed at improving the antibacterial activity of naturally-occurring chalcones by increasing their water solubility. Nielsen, S. F.; Boesen, T.; Larsen, M.; Schonning, K.; Kromann, H., Antibacterial chalcones-bioisosteric replacement of the 4'-hydroxy group. *Bioorg. Med. Chem.* 2004, 12, 3047-3054; Nielsen, S. F.; Larsen, M.; Boesen, T.; Schonning, K.; Kromann, H., Cationic chalcone antibiotics. design, synthesis, and mechanism of action. *J. Med. Chem.* 2005, 48, 2667-2677.

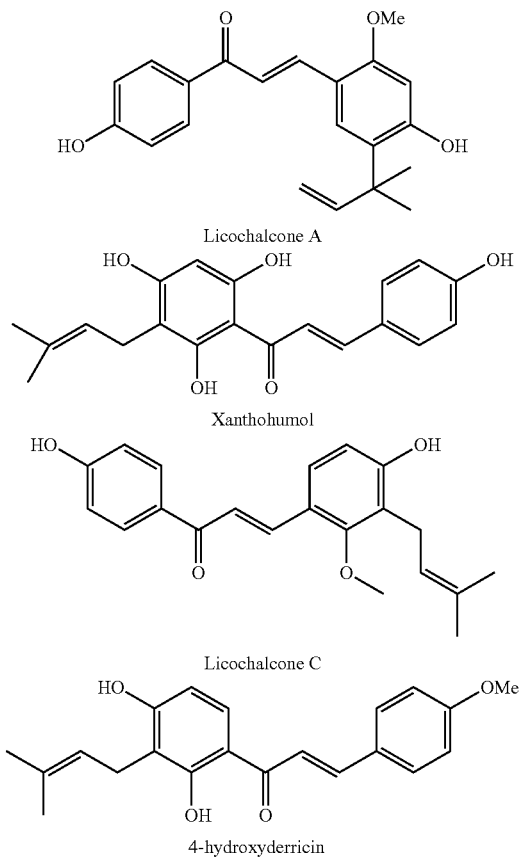

Chalcones should thus be a useful scaffold for making and assessing small molecules for antimicrobial activity. Furthermore, chalcones are adaptable to macroarray methods due to their relatively straightforward synthesis. The key feature of combinatorial chemistry—the speed at which a large number of diverse compounds can be generated—can be applied to the rapid discovery of new lead structures for use as antibacterial agents. The generation of small molecule macroarrays can streamline the process for generating diverse small molecule libraries with potential antibacterial activities, and can be used to identify novel antimicrobial agents, including antibacterial agents.

Backwell et al. WO 2008/016738 (published Feb. 7, 2008) have reported making chalcone-based small molecule macroarrays including chalcones, and cyanopyridine and methylpyrimidine derivatives of chalcones and the screening of the compound libraries made for antibacterial activity. These macroarrays employed planar cellulose membranes derivatized with a Wang-type linker. See: Bowman, et al. *Tetrahedron* 2006.

Bacterial cellular membranes have been identified as a possible target of antibacterial agents. Bacterial membranes are composed mostly of negatively charged phospholipid, phosphatidylglycerol. In contrast, eukaryotic cellular membranes comprise two different phospholipids, phosphatidylcholine and sphingomyelin. Zasloff, M., Antimicrobial peptides of multicellular organisms. *Nature* 2002, 415, 389-395. The differences in the composition of bacterial and eukaryotic membranes represent a unique structural difference that may be exploited as an antibacterial target. This is shown in the effectiveness of certain antimicrobial peptides, which are inherently present in humans, termed host-defense peptides. Host-defense peptides are short peptides (12-50 amino acids) that are found in a variety of living organisms including humans, and there have been synthetic examples of mimicking host-defense peptides for use as a potential antibacterial therapeutic. Schmitt, M. A.; Weisblum, B.; Gellman, S. H., Unexpected relationships between structure and function in alpha-, beta-peptides: antimicrobial foldamers with heterogeneous backbones. *J. Am. Chem. Soc.* 2004, 126, 6848-6849; Epand, R. F.; Raguse, T. L.; Gellman, S. H.; Epand, R. M., Antimicrobial 14-Helical beta-Peptides: Potent Bilayer Disrupting Agents. *Biochemistry* 2004, 43, 9527-9535; Schmitt, M. A.; Weisblum, B.; Gellman, S. H., Interplay among Folding, Sequence, and Lipophilicity in the Antibacterial and Hemolytic Activities of alpha/beta-Peptides. *J. Am. Chem. Soc.* 2007, 129, 417-428. Most of these amphipathic peptides contain structural features that are believed to contribute to their antibacterial activity, including regions of positively charged amino acid residues (for attraction to negatively charged bacterial membranes), and regions of hydrophobic amino acid residues (for insertion and subsequent disruption of the membrane).

Peptoids, or N-substituted glycine oligomers, are possible alternatives to antimicrobial peptides because they are resistant to proteolytic degradation and diverse libraries with a variety of sidechains can be generated using commercially available amines.

The present invention relates to additional methods for synthesis of small molecule macroarrays of chalcones and derivatives thereof and screening of such arrays for useful biological activities, including therapeutic activities and particularly antimicrobial activities. The invention relates in a second aspect to methods for covalently linking amino acids, peptides and/or peptoids to the chalcones and chalcone derivatives of such macroarrays to expand the potential for new antimicrobial compounds. The invention additionally relates to novel chalcones and chalcone derivatives exhibiting antimicrobial, particularly antibacterial activity.

SUMMARY OF THE INVENTION

Figure 1:
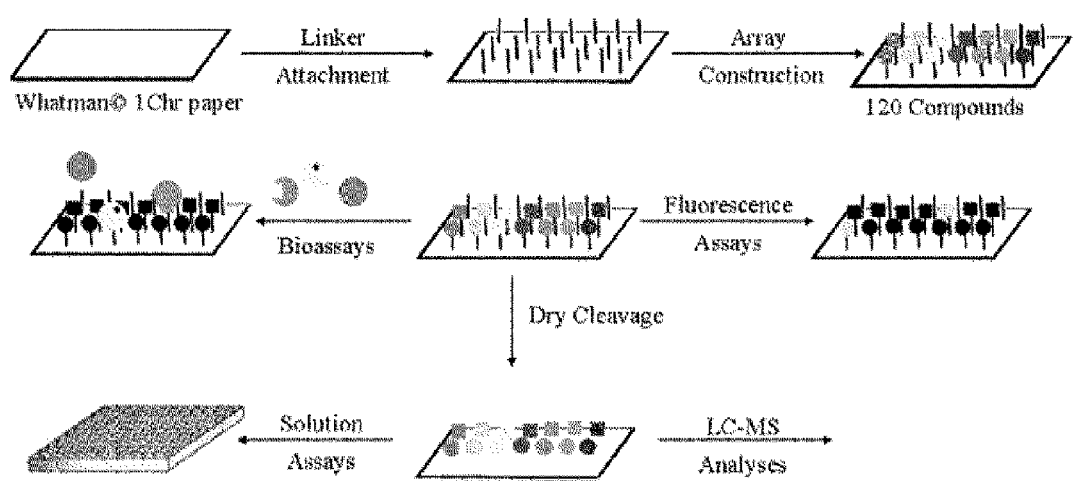
FIG. 1 illustrates a graphical representation of small molecule macroarray construction.

In one aspect, the invention relates to methods for generating small molecule macroarrays useful for screening of the molecules therein for antimicrobial activity. The methods employ a solid-support platform, preferably a planar cellulose support, which involves the use of a Rink amide linker (See FIG. 2) to attach small molecules of the library to the support. The use of this linker results in the formation of an amide group on small molecules released from the support (See FIG. 3). This group is polar and generally enhances the water-solubility of the small molecule which in turn can enhance the biological activity of the small molecule. The use of the Rink linker in synthesis of macroarrays and or microarrays allows additional chemical moieties to be covalently attached to the small molecules to enhance the diversity of molecules which can be synthesized and screened using the macroarray methods. In particular, the invention provides methods for making such small molecules linked to amino acids, peptides, N-substituted glycines, or peptoids (oligomers of N-substituted glycines). The attachment of such species can enhance and/or expand the biological activity of the small molecules to which they are attached and allow for targeting of the small molecules to specific sites in a cell or in an organism.

The use of the Rink linker for attachment of library compounds to the solid platform provides better mechanical properties for the on-support screening of the small molecule macroarrays.

The present invention provides versatile methods for screening compounds for antimicrobial activity, including antibacterial activity. The present methods are based on using combinatorial synthetic methods to generate arrays (e.g., macroarrays) comprising a large number of candidate molecules, identifying compounds of the array exhibiting antimicrobial activity and quantifying MICs of select compounds in the array. Structurally distinct candidate molecules are synthesized and bonded to distinct known locations (e.g., spots or regions) on a surface of a unitary substrate via linkers (i.e., linking groups attaching the candidates to the substrate). Candidate molecules are subsequently liberated from the substrate by cleaving the linkers and assayed for antibacterial activity by bringing the array into contact with a microbial culture, such as a bacterial culture or fungal culture. An advantage provided by the macroarray platform of the present screening methods is that qualitative and/or quantitative characterization of the antibacterial properties of large numbers of candidate compounds can be achieved on a relatively short time scale (i.e. days) using a single overlay visualization and/or quantification assay step.

In specific embodiments, the methods of this invention are applied to the synthesis of small molecule chalcones and derivatives thereof, particularly, cyanopyridine derivatives, alkyl pyrimidine derivatives and aminopyrimidine derivatives thereof.

In specific embodiments, the methods of this invention are applied to the synthesis of macroarrays for screening for antimicrobial activity. In more specific embodiments, the methods of this invention are applied to the synthesis of macroarrays for screening for antibacterial activity. In additional specific embodiments, the methods of this invention are used for screening macroarrays for activity against strains of the genus *Staphylococcus* and more particularly against strains of *S. aureus* and even more particularly against strains of *Staphylococcus* and *S. aureus* which exhibit methicillin-resistance (e.g., MRSA). The methods herein can be employed for the synthesis and identification of antibacterial compounds.

In another aspect, the present invention relates generally to compounds providing antibacterial therapeutic agents and preparations, and related methods of using and making antibacterial compounds. Antibacterial compounds of the present invention include chalcone, and alkylpyrimidine, aminopyrimidine and cyanopyridine derivatives of chalcones exhibiting antibacterial activity. In particular, certain antibacterial compounds of the invention exhibit minimum inhibitory concentrations (MIC) against a given bacterium similar to or less than conventional antibacterial compounds in wide use.

In an aspect, the present invention provides a composition of matter comprising a chalcone or chalcone derivative having Formula I:

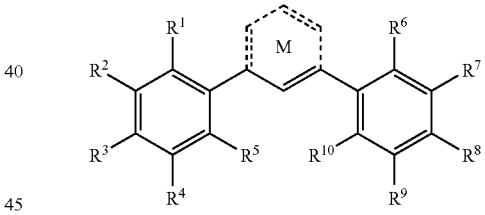

Formula I and salts, esters and solvates thereof,
where:
M is

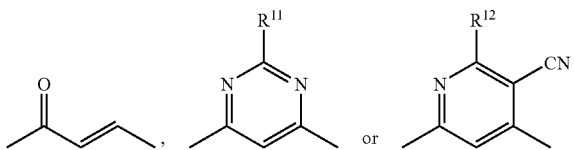

where $R^{11}$ is a an optionally substituted C1-C6 alkyl or NRR', $R^{12}$ is an optionally substituted C1-C6 alkyl and R and R' are independently selected from the group consisting of hydrogen, an optionally substituted C1-C6 alkyl, particularly a C1-C6 alkyl substituted with a C6-C13 aryl group, or an optionally substituted C3-C8 cycloalkyl, an optionally substituted C3 to C10 heterocycloalkyl or an optionally substituted C3 to C10 heterocycloalkene, each of which heterocycles contain 1, 2 or 3 heteroatoms (e.g., O, N or S), or an optionally substituted C6-C13 aryl group which includes an C1-C6 alkyl-substituted aryl group,
at least one of $R^1$-$R^5$ is a —O—(CH$_2$)$_n$—CO—NH$_2$ group, where n is an integer ranging from 1-6 (inclusive) and the remaining $R^1$-$R^5$ are selected from hydrogen, halogen, hydroxyl, an amino group (—NH$_2$, —NRR'), a —CN group, an azide group, a —NO$_2$ group, an optionally substituted C1-C12 alkyl, alkenyl or alkynyl group, an optionally substituted C6-C13 aryl group, an optionally substituted heterocycloalkyl C3-C8 (where the heteroatom(s) are N, O or S) and optionally substituted C1-C12 alkoxy or C6-C13 aryloxy groups;
at least one of $R^6$-$R^{10}$ is a non-hydrogen substituent, where $R^6$-$R^{10}$ are independently selected from the group consisting of hydrogen, halogen, hydroxyl, an amine group, a —CN group, an azide group, a —NO$_2$ group, an optionally substituted C1-C12 alkyl, C2-C12 alkenyl or C2-C12 alkynyl group, an optionally substituted C6-C13 aryl group, an optionally substituted C1-C12 alkoxy or C6-C13 aryloxy group, or a —O—(CH$_2$)$_m$—CO—NH$_2$ group, where m is an integer ranging from 1-6 (inclusive).

In the above definitions, R and R' are selected from hydrogen, C1-C6 alkyl (preferably C1-C3 alkyl), C3-C8 cycloalkyl, including cyclohexyl, C4-C8 heterocycloalkyl (heteroatom=N, O or S), and C6-C13 aryl.

Optional substitution, includes substitution with one or more halogens, —OH, —OR, —SH, —SR, —COOH, —COO$^-$, —NRR', —NRR'R", —CONRR', —NR—C(NRR')=NR, —NR—C(NRR')=NRR'$^+$, or C1-C3-alkyl groups, which in turn are optionally substituted with one or more halogens, —OH, —SH, —COOH, —COO$^-$, C1-C3 alkoxy, —NRR', —NRR'R", —CONRR', —NR—C(NRR')=NR, or —NR—C(NRR')=NRR', where R, R' and R" are in particular hydrogen, or C1-C3 alkyl groups or C6-C13 aryl groups, which in turn can be substituted with one or more halogens, —OH, —SH, —COOH, —COO$^-$, or C1-C3 alkoxy.

In another aspect, the invention provides, chalcones, alkyl-substituted cyanopyridines and alkyl-substituted alkyl or animopyrimidines of Formula X:

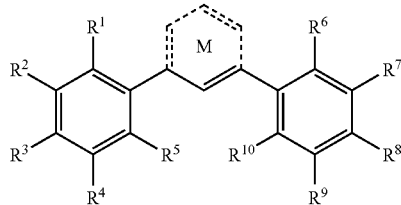

Formula X and salts, esters and solvates thereof
where:
M is

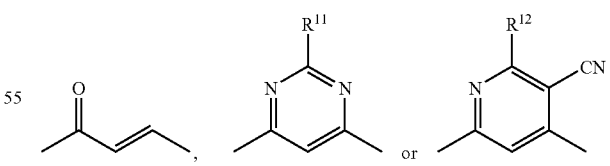

$R^{11}$ is a C1-C6 alkyl or NRR' and $R^{12}$ is $C_1$-$C_6$ alkyl and R and R' are independently selected from the group consisting of hydrogen, C1-C6 alkyl which can be substituted with one or more of halogen, C6-C13 aryl group, a C3-C8 cycloalkyl, a C3 to C10 heterocycloalkyl, (where the heteroatom(s) are N, O or S) which contains 1 or 2 heteroatoms (e.g., O, N or S), or a C6-C13 aryl group which includes an C1-C6 alkyl-substituted aryl group;

at least one of $R^1$-$R^5$ is selected from

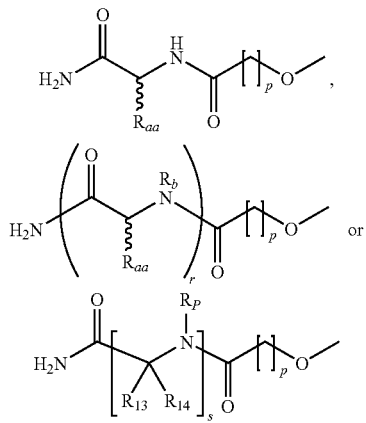

where:
each p, independently, is an integer from 1 to 6, inclusive, and r and s, independently are integers ranging from 1 to 100, inclusive, and more preferably r and s range from 2-10, 6-20, or 10-50 inclusive, $R_{aa}$ is selected from hydrogen, C1-C8 alkyl, C1-C8 alkenyl, C1-C8 alkynyl, C6-C13 aryl, C6-C13 aralkyl, C1-C8 ether, C1-C8 thioether, C3-C8 cycloalkyl or cycloalkenyl, C3-C10 heterocylic which contains 1, 2 or 3 heteroatoms (e.g., N, O or S), or a C3-C13 heteroaromatic group having 1, 2 or 3 heteroatoms (N, O or S) all of which groups are optionally substituted, particularly with one or more halogens, OH, OR, SH, SR, C1-C3-alkyl, —COOH, —COO$^-$, —NRR', —NRR'R'', —CONRR', —NR—C(NRR')=NR, and —NR—C(NRR')=NRR'$^+$, where R, R' and R'' are in particular hydrogen, and C1-C3 alkyl groups; and $R_b$ is hydrogen, C1-C3 alkyl or $R_{aa}$ and $R_b$ together form an optionally substituted C3-C8 cycloalkyl or cycloalkenyl which optionally contains one or two heteroatoms (e.g., N, O or S), or $R_b$ is

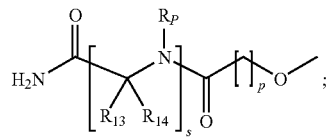

$R_p$ is selected from hydrogen, C1-C8 alkyl, C1-C8 alkenyl, C1-C8 alkynyl, C6-C13 aryl, C1-C8 ether, C1-C8 thioether, C3-C8 cycloalkyl or cycloalkenyl group, which optionally contains one or two heteroatoms (e.g., N, O or S), and a C3-C13 heteroaromatic group having 1, 2 or 3 heteroatoms (N, O or S), all of which are optionally substituted, particularly with one or more halogens, OH, OR, SH, SR, C1-C3-alkyl, —COOH, —COO$^-$, —NRR', —NRR'R'', —CONRR', —NR—C(NRR')=NR, and —NR—C(NRR')=NRR'$^+$, where R, R' and R'' are in particular hydrogen, and optionally substituted C1-C3 alkyl groups; and one of $R_{13}$ or $R_{14}$ together with $R_{aa}$ form an optionally substituted C3-C8 cycloalkyl or cycloalkenyl group which optionally contains one or two heteroatoms (e.g., N, O or S);

each $R_{13}$ and $R_{14}$ are independently selected from hydrogen, C1-C6 alkyl which may be substituted with one or more halogens and benzyl or phenyl optionally substituted with one or more halogens, hydroxyl or C1-C3 alkyl groups;

remaining $R^1$-$R^{10}$ are independently selected from the group consisting of hydrogen, hydroxy, halogen, nitro, alkyl, alkenyl, alkynyl, cycloalkyl, alkoxy, aryl, aralkyl, aryloxy, arylthio, heteroaryl, heteroarylalkyl, heterocyclic, amino, aminoalkyl, aminoarylalkyl, hydroxyaminoalkyl, cycloalkylaminoalkyl, heteroarylaminoalkyl, heterocyclicaminoalkyl, hydroxyl, hydroxyalkyl, alditol, carbohydrate, polyol alkyl, —(O(CH$_2$)$_{2(1-3)}$O—C1-C3 alkyl, polyoxyalkylene, cycloalkyloxy, cycloalkylalkoxy, haloalkoxy, arylalkoxy, heteroarylalkoxy, heterocyclicoxy, heterocyclicalkoxy, —O(C(R)$_2$)$_{1-6}$C(O)OR, —O(C(R)$_2$)$_{1-6}$C(O)NRR', amino, alkylamino, acylamino, dialkylamino, cycloalkylamino, arylamino, aralkylamino, heteroarylamino, heteroaralkylamino, heterocyclicamino, heterocyclicalkylamino, —NRR', —NH(C(R)$_2$)$_{1-6}$C(O)OR', —NRC(O)R', —NRC(O)OR', —NRC(O)SR', —NRSO$_2$NRR', —NHSO$_2$R', —NRSO2NRR', —N(C(O)NRR')$_2$, —NRSO$_2$R, —NRC(O)NRR', thiol, alkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —S(CRR')$_{1-6}$COOR, —S(CF$_2$)$_{1-6}$COOR, —SO$_2$NRR', —SO$_2$NROR, —SO$_2$NR(O)NRR', sulfonic acid, sulfonate, sulfate, sulfinic acid, sulfenic acid, cyano, tetrazol-5-yl, carboxy, —C(O)OR, —CONRR', —C(O)NR(O)R, —CONRSO$_2$R, —CONRSO$_2$NRR', —(CRR')$_{1-6}$(O)OH, —PO$_2$H$_2$, —PO$_3$H$_2$, —P(R)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, alkoxy, oxo, cyano, carboxy, carboxyalkyl, alkoxycarbonyl, and groups formed by replacing one (preferably) or more non-adjacent CH$_2$ groups of an alkyl group with an —O-(ether)-S-(thioether), —NR—, —CO—, —SO—, SO$_2$—, —NR—CO—, —NR—CO—NR—, —NR—CO—O—, —CO—O—, —CO—S—, —CO—, -aryl-, -aryl-O—, -aryl-S—, -heteroaryl-, or a -heterocyclic-moiety; and optionally two $R^1$-$R^5$ on adjacent ring carbons and/or two $R^6$-$R^{10}$ on adjacent ring carbons taken together form a 3-8 member cycloalkyl, a 3-8 member heterocyclic group having 1-3 heteroatoms (e.g., N, O and/or S), a C6-C12 aryl, a 3-8 member heteroaryl group (having 1-3 heteroatoms (e.g., N, O and/or S) optionally substituted by one or more C1-C3 alky, acyl, alkoxycarbonylalkyl, carboxyalkyl, hydroxyalkyl, aminoalkyl, aminohydroxylalkyl, hydroxy, alkyl, carboxy, hydroxyalkyl, carboxyalkyl, amino, cyano, alkoxy, alkoxycarbonyl, acyl, oxo, —NRR', cyano, carboxy, and halo.

In specific embodiments, $R_{aa}$, $R_{13}$ or $R_{14}$, independently of each other, are selected from one or more of hydrogen, methyl, isopropyl, isobutyl, sec-butyl, methylthioethyl, phenylmethyl, 4-OH-phenylmethyl, mercaptomethyl, hydroxylmethyl, 2-hydroxy-ethyl, 4-aminobutyl, carbamoylmethyl, 2-carbamoylethyl, carboxymethyl, 2-carboxyethyl, 1H-imidazol-4-yl-methyl, 3-guanidopropyl, or -(1H-indol-3-yl)methyl groups.

The present invention provides compounds exhibiting useful in vitro antibacterial activities against a variety of bacteria strains, including drug resistant bacterial strains, thereby providing antibacterial therapeutic agents and preparations useful for a range of important clinical applications.

In another aspect, the present invention provides combinatorial libraries of compounds, including candidate compounds for screening microbial activity including antibacterial activity. In an embodiment of this aspect of the present invention, the present invention provides one or more combinatorial libraries of chalcone compounds and/or derivative thereof having any one of the formulas herein.

In another aspect, the present invention provides pharmaceutical and therapeutic preparations comprising a therapeutically effective amount of one or more compounds of the present invention of Formula I and X above optionally in combination with a pharmaceutically acceptable carrier. In particular, pharmaceutical and therapeutic preparations of this invention comprise an amount or combined amount of one or more compounds of this invention effective for inhibiting the growth of a selected bacterium, particularly a bacterial pathogen and more particularly a bacterial human or veterinary pathogen. Compounds useful in the methods of this invention include pharmaceutically-acceptable salts and esters of the compounds of formulas herein. Compounds useful in the methods of this invention include pharmaceutically-acceptable prodrugs of the compounds of formulas herein.

Salts include any salts derived from the acids of the formulas herein which are acceptable for use in human or veterinary applications. The term esters refer to hydrolyzable esters of chalcone compounds, or chalcone derivatives of the present invention. The term ester includes, among others, esters of the compounds of the formulas herein (e.g., Formulas I and X), in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms. Salts and esters of this invention are prepared by methods that are well known in the art. Salts and esters of the compounds of the formulas herein are those which have the same or similar pharmaceutical or therapeutic (human or veterinary) properties as the chalcone compounds and/or chalcone derivatives of the present invention. Therapeutic and pharmaceutical preparations of the present invention comprise one or more of the compounds of the present invention in an amount or in a combined amount effective for obtaining the desired therapeutic benefit. Therapeutic and pharmaceutical preparations of the invention optionally further comprise a pharmaceutically acceptable carrier as known in the art.

In another aspect, the present invention provides a method of treating an infectious disease comprising administering to a patient in need of treatment, a composition comprising a compound of the present invention. In an embodiment, the infectious disease relates to that associated with an infectious agent comprising a bacterium. In an embodiment, the bacteria are Gram-positive bacteria. In a specific embodiment, the bacteria include one or more of *Bacillus, Listeria, Staphylococcus, Streptococcus, Enterococcus, Corynebacterium, Propionibacterium* and *Clostridium*. In a specific embodiment, the bacteria are one or more selected from the group consisting of *S. aureus, S. epidermidis* and *B. subtilis*. In a specific embodiment, the bacteria are one or more drug resistant bacteria.

In another aspect, the present invention provides methods of inhibiting growth of bacteria. In a specific embodiment of this aspect, a method of the present invention comprises the step of contacting the bacteria with an effective amount of one or more chalcone or chalcone derivative compounds of this invention which exhibit antibacterial activity. In an embodiment, the bacteria are Gram-positive bacteria. In a specific embodiment, the bacteria include one or more of *Bacillus, Listeria, Staphylococcus, Streptococcus, Enterococcus, Corynebacterium, Propionibacterium* and *Clostridium*. In a specific embodiment, the bacteria are one or more selected from the group consisting of *S. aureus, S. epidermidis* and *B. subtilis*. In a specific embodiment, the bacteria are one or more drug resistant bacteria. Methods of inhibiting bacteria of the present invention include methods useful for treatment of a subject (human or veterinary) and also include methods useful for inhibiting bacteria outside of a subject, such as use for sterilization and disinfection.

In another embodiment, the invention provides a medicament for treatment of a an infectious disease, particularly one associated with or caused by a bacterium. The medicament comprises a therapeutically effective amount of one or more compounds of this invention as illustrated in one or more formulas herein which compounds exhibit antimicrobial and/or antibacterial activity. The invention also provides a method for making this medicament which comprises combining a therapeutically effective amount of one or more compounds of this invention having antimicrobial and/or antibacterial activity with a selected pharmaceutical carrier appropriate for a given method of administration. The medicament may be an oral dosage form, an intravenous dosage form or any other art-recognized dosage form.

Figure 3:
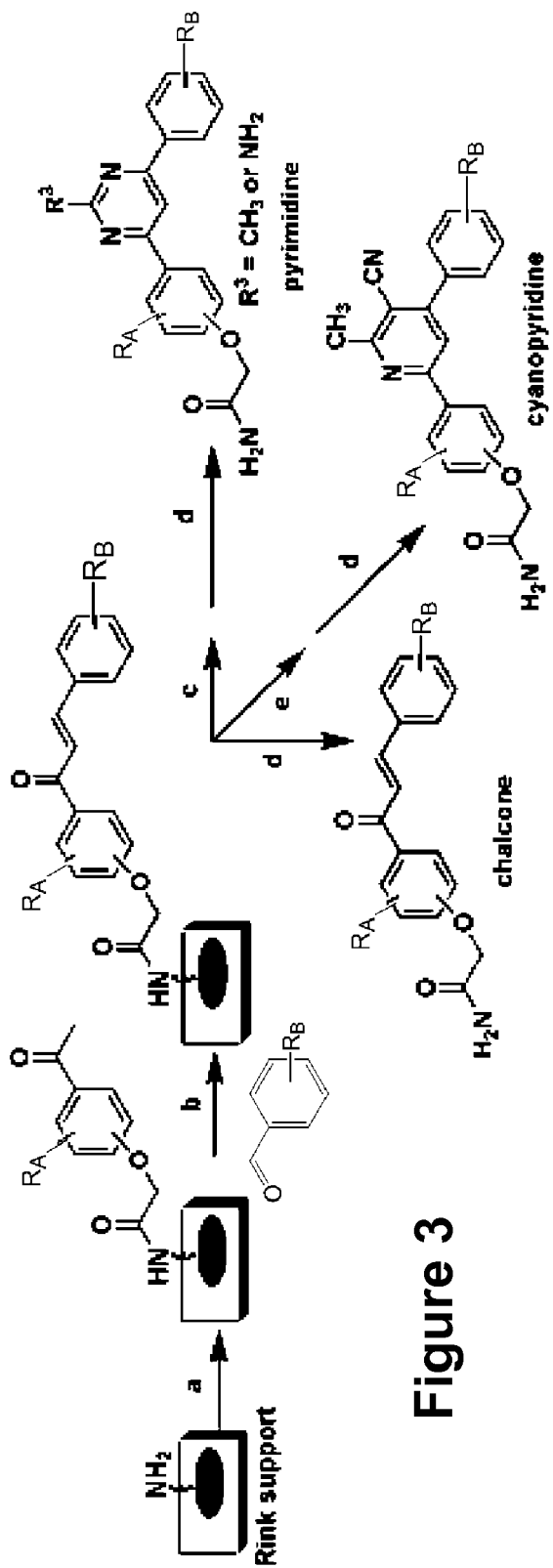
FIG. 3 provides a synthetic scheme showing the pathway for synthesis of library members.

In another aspect, the present invention provides methods of synthesizing the compounds of the present invention, including methods of synthesizing chalcones, cyanopyridine derivatives of chalcones, alkylpyrimidine derivatives of chalcones, and aminopyrimidine derivatives of chalcones. In an embodiment, for example, the present invention includes methods of synthesizing compounds employing a Rink linker as illustrated in FIG. 3 herein.

In another aspect, the present invention provides methods of screening compounds, classes of compounds and combinatorial libraries of compounds for antimicrobial activity, including antibacterial activity. In an embodiment of this aspect, a method for screening a plurality of candidate compounds for antimicrobial activity of the present invention comprises the steps of: (i) providing a spatially-addressed array of the candidate compounds supported by a first unitary substrate, wherein the candidate compounds are individually addressed to selected positions of the substrate via linkers; (ii) contacting a microbial culture with the array or with a portion of the array transferred to a second unitary substrate in a manner retaining the relative positions of candidate compounds in the array, whereby candidate compounds having antimicrobial activity exhibit a zone of inhibition in the microbial culture; and (iii) identifying one or more positions in the array or transferred portion of the array corresponding to one or more candidate compounds exhibiting zones of inhibition. In the methods herein, the candidate compounds of the spatially addressed array are linked to that array employing a Rink linker as illustrated in FIG. 3 herein. Optionally, methods of this aspect of the present invention further comprise the step of transferring the portion of the array to a second unitary substrate in a manner retaining the relative positions of candidate compounds in the array. In some embodiments, this transfer step is carried out multiple times so as to generate a plurality of array samples for screening. In a specific embodiment, the invention provides a method of screening the plurality of candidate compounds for antibacterial activity wherein the microbial culture is a bacterial culture. Alternatively, the invention provides a method of screening the plurality of candidate compounds for anti-fungal activity wherein the microbial culture is a fungal culture. Useful arrays in the present methods include macroarrays and microarrays of candidate compounds.

The present invention includes methods using overlay assaying techniques wherein a microbial culture is provided in contact with the entire array or a portion thereof to provide effective, nearly simultaneous readout of the activities of a large number of candidate compounds. Overlay assaying techniques useful in these methods include, but are not limited to, techniques wherein an agar medium inoculated with bacteria is provided in contact with the array to provide screening of the antibacterial activities of candidate compounds of the array.

In some embodiments, the methods of the present invention further comprise the step of cleaving the linkers prior to the step of contacting the bacterial culture with the array or transferred portion of the array. This additional step facilitates achieving effective and biologically significant contact between compounds of the array and the microbial culture. Preferably, the step of cleaving the linkers connecting compounds of the array and the substrate is carried out in a way that does not substantially disrupt the position of individual compounds of the array on the substrate. In some embodiments, the screening methods further comprises the step of transferring the portion of the array to a second unitary substrate in a manner retaining the relative positions of candidate compounds in the array. Exemplary means of transferring a portion of the array in these embodiments include, but are not limited to, overlay transfer methods, such as positioning cleaved arrays between a solvent saturated surface and one or more dry cellulose sheets. An advantage of this embodiment of the present invention is that a single array may be used to generate a plurality of "copies" (i.e., transferred portions of the array which retain the spatially address nature of the compounds in the array) that can be screened to provide replicated assays.

Screening methods of the present invention may further comprise a number of optional steps. In an embodiment, for example, the method further comprises incubating the microbial culture, such as a bacteria culture, in contact with the array or transferred portion of the array. In an embodiment, for example, the method further comprises the step of measuring a zone of inhibition parameter exhibited by one or more candidate compounds of the array. Useful zone of inhibition parameters for the present methods include, but are not limited to, a diameter of inhibition, a radius of inhibition, and an area of inhibition. In an embodiment, for example, the method further comprises the step of contacting the bacterial culture with a visualization agent, whereby the visualization agent is capable of differentiating between zones of inhibition and zones of no activity. Useful visualization agents include, but are not limited to, redox indicators such as triphenyl tetrazolium chloride capable of providing clear and reproducible visualization of areas of live and dead bacteria for the measuring one or more zone of inhibition parameters.

Preferably for many applications, candidate compounds are linked to the substrate in a manner such that they can be non-destructively cleaved from the first unitary substrate. The choice of linker and mechanism of cleavage from the substrate may affect the composition of candidate compounds released from the substrate via cleavage reactions. When the Rink linker is used, for example, cleavage of linkers results in candidate compounds having an —CO—NH$_2$ group introduced through the linking chemistry.

Substrates useful in the present methods include planar (2D) substrates and three-dimensional substrates. Three-dimensional substrates include beaded materials, such as beaded cellulose, and other useful materials such as tissue engineering scaffolds. A range of substrate compositions are useful in the present invention including, but not limited to, cellulose substrate, nylon substrate, polypropylene substrate, polycarbonate substrate, glass substrate, gold substrate, silicone substrate or amorphous carbon substrate. In some embodiments, the unitary substrate supporting the arrays of this invention is a planar substrate.

In some methods candidate compounds are synthesized in an array bound to a surface. The candidate compounds are typically linked to the surface by a linker group, preferably for many screening applications a cleavable linker group. In the methods described herein a Rink Linker is employed. The methods of this invention are particularly useful when practiced with macroarrays. However, the methods can be practiced employing microarrays.

DETAILED DESCRIPTION OF THE INVENTION

All technical and scientific terms used herein have the broadest meanings as commonly understood by one of ordinary skill in the art to which this invention pertains.

The present invention relates in part to libraries of compounds prepared in array form for testing for biological activity. The array format of the methods herein is particularly suited to assessing activity of library compounds for antimicrobial activity, including anti-fungal, anti-yeast, anti-protozoan, and antibacterial activity. Compounds of libraries herein exhibit antimicrobial activity including antibacterial activity.

For example, the present invention provides in one aspect a composition of matter comprising a chalcone or chalcone derivative having Formula I:

Formula I

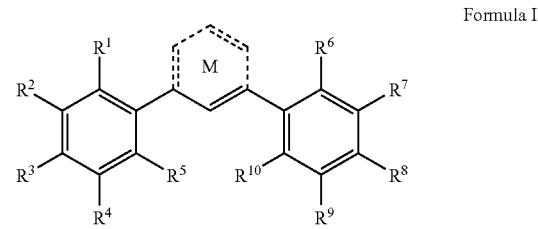

and salts, esters and solvates thereof,
where:
M is

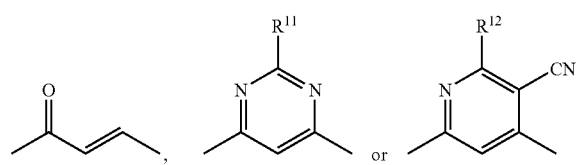

where $R^{11}$ is a C1-C6 alkyl or NRR' and $R^{12}$ is $C_1$-$C_6$ alkyl and R and R' are independently selected from the group consisting of hydrogen, C1-C6 alkyl which can be substituted with a C6-C13 aryl group, a C1-C8 cycloalkyl, a heterocycloalkyl C3-C8 (where the heteroatom(s) are N, O or S) which optionally contains 1 or 2 heteroatoms (e.g., O, N or S), or a C6-C13 aryl group which includes an C1-C6 alkyl-substituted aryl group,
one of $R^1$-$R^5$ is a —O—(CH$_2$)$_n$—CO—NH$_2$ group, where n is 1-6 and the remaining $R^1$-$R^5$ are selected from hydrogen, halogen, hydroxyl, an amino group (—NH$_2$, —NRR'), a —CN group, an azide group, a —NO$_2$ group, an optionally substituted C1-C12 alkyl, alkenyl or alkynyl group, an optionally substituted C6-C13 aryl group, an optionally substituted heterocycloalkyl C3-C8 (where the heteroatom(s) are N, O or S) and optionally substituted C1-C12 alkoxy or C6-C13 aryloxy groups;

wherein at least one of $R^6$-$R^{10}$ is a non-hydrogen substituent and where $R^6$-$R^{10}$ are independently selected from the group consisting of hydrogen, halogen, hydroxyl, an amine group, a —CN group, an azide group, a —NO$_2$ group, an optionally substituted C1-C12 alkyl, alkenyl or alkynyl group, an optionally substituted C6-C13 aryl group, an optionally substituted C1-C12 alkoxy or C6-C13 aryloxy group, and a —O—(CH$_2$)$_m$—CO—NH$_2$ group, where m is 1-6.

More specifically the invention provides a chalcone compound of Formula II:

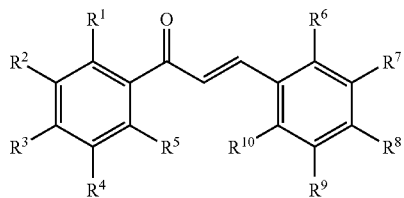

Formula II and salts, esters and solvates thereof wherein one of $R^1$-$R^5$ is a —O—(CH$_2$)$_n$—CO—NH$_2$ group where n is 1-6 and the remaining $R^1$-$R^5$ are selected from hydrogen, halogen, hydroxyl, an amine group (—NH$_2$, —NRR'), a —CN group, an azide group, a —NO$_2$ group, optionally substituted C1-C12 alkyl, alkenyl or alkynyl groups, optionally substituted C6-C13 aryl groups, optionally substituted heterocycloalkyl C3-C8 (where the heteroatom(s) are N, O or S) and optionally substituted C1-C12 alkoxy or C6-C13 aryloxy groups, wherein at least one of $R^6$-$R^{10}$ is a non-hydrogen substituent and where $R^6$ to $R^{10}$ are selected from the group consisting of from hydrogen, halogen, hydroxyl, an amine group, a —CN group, an azide group, a —NO$_2$ group, optionally substituted C1-C12 alkyl, alkenyl or alkynyl groups, optionally substituted C6-C13 aryl groups, optionally substituted C1-C12 alkoxy or C6-C13 aryloxy groups, and a —O—(CH$_2$)$_m$—CO—NH$_2$ group, where m is 1-6.

Additionally the invention provides compounds of Formulas III and IV:

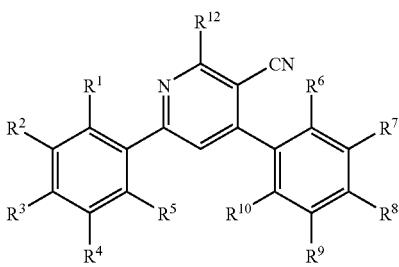

Formula III

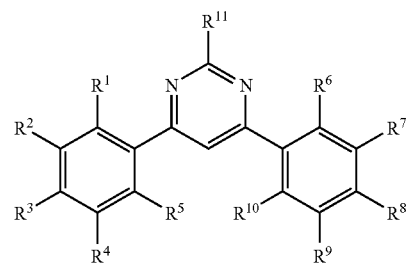

Formula IV where variables are as defined above, and where $R^{11}$ is more preferably an optionally substituted C1-C3 alkyl or an —NH$_2$ group and $R^{12}$ is more preferably a C1-C3 alkyl or hydrogen.

In specific embodiments of the compounds of Formulas I-IV, X and XI (below), one, two or three of $R^6$-$R^{10}$ are halogens, including one, two or three bromines, one, two or three chlorines or one, two or three fluorines. In a specific embodiment the remaining $R^6$-$R^{10}$ are hydrogens.

In specific embodiments of the compounds of Formulas I-IV, X and XI, one, two or three of $R^6$-$R^{10}$ are C1-C6 haloalkyl groups, including one, two or three C1-C6 perfluoralkyl groups, one, two or three C1-C3 perfluoralkyl groups or one, two or three trifluoromethyl groups and the remaining $R^6$-$R^{10}$ are hydrogens.

In specific embodiments of the compounds of Formulas I-IV, X and XI, $R^6$, $R^7$ and $R^9$ or $R^{10}$ are halogens or haloalkyl groups, particularly bromines, chlorines or fluorines and particularly trifluoromethyl groups. In a specific embodiment the remaining $R^8$ and $R^9$ or $R^{10}$ are hydrogens.

In specific embodiments of the compounds of Formulas I-IV, X and XI, $R^6$, $R^7$ and $R^9$ or $R^{10}$ are halogens, particularly bromines, chlorines or fluorines. In a specific embodiment the remaining $R^8$ and $R^9$ or $R^{10}$ are hydrogens.

In specific embodiments of the compounds of Formulas I-IV, X and XI, $R^6$, $R^7$ and $R^9$ or $R^{10}$ are C1-C6 fluoroalkyl groups, more specifically perfluoroalkyl group, and even more specifically trifluoromethyl groups. In a specific embodiment the remaining $R^8$ and $R^9$ or $R^{10}$ are hydrogens.

In specific embodiments of the compounds of Formulas I-IV, X and XI, $R^{11}$ and $R^{12}$ are C1-C3 alkyl or hydrogen.

In specific embodiments of the compounds of Formulas I-IV, X and XI, $R^6$ or $R_7$ or $R_8$ is a halogen or a C1-C3 perfluoralkyl group. In a specific embodiment the remaining $R^6$-$R^{10}$ groups are hydrogens.

In specific embodiments of the compounds of Formulas I-IV, X and XI, one of $R^1$-$R^5$ is an OH, C1-C3 alkoxy, a phenoxy, a benzyloxy, —COC1-C3 alkyl, C1-C6 haloalkyl, or halo. In another specific embodiment of the compounds of Formulas I-IV, X and XI, one of $R^1$-$R^5$ is an OH, methoxy, trifluoromethyl, bromo, fluoro or chloro group.

In specific embodiments of the compounds of Formulas I-IV, one of $R^1$, $R^2$ or $R^3$ is —O—(CH$_2$)$_n$—CO—NH$_2$, where n is 1-6. In other embodiments, $R^1$ is —O—(CH$_2$)$_n$—CO—NH$_2$, where n is 1-6. In other embodiments, $R^2$ is —O—(CH$_2$)$_n$—CO—NH$_2$, where n is 1-6. In other embodiments one of $R^1$, $R^2$ or $R^3$ is —O—CH$_2$CO—NH$_2$. In other embodiments, $R^1$ is —O—CH$_2$—CO—NH$_2$. In other embodiments, $R^2$ is —O—CH$_2$—CO—NH$_2$. In other embodiments, all other $R^1$-$R_5$ are hydrogens.

In specific embodiments of the compounds of Formulas I-IV, $R^1$ is —O—(CH$_2$)$_n$—CO—NH$_2$, where n is 1-6 and $R^4$ is a halogen. In specific embodiments, all of $R^2$, $R^3$ and $R^5$ are hydrogens.

In specific embodiments of the compounds of Formulas I-IV, $R^1$ is —O—$(CH_2)_n$—CO—$NH_2$, where n is 1-6 and all of $R^2$, $R^3$, $R^4$ and $R^5$ are hydrogens.

In specific embodiments of the compounds of Formulas I-IV, $R^3$ is —O—$(CH_2)_n$—CO—$NH_2$, where n is 1-6 and $R^4$ is a C1-C3 alkyl or perfluoralkyl. In specific embodiments, all of $R^1$, $R^2$ and $R^5$ are hydrogens.

In specific embodiments of the compounds of Formulas I-IV and X, none of $R^1$-$R^{10}$ is an OH group. In specific embodiments of the compounds of Formulas I-IV and X, none of $R^1$-$R^5$ is an OH group. In specific embodiments of the compounds of Formulas I-IV and X, none of $R^6$-$R^{10}$ is an OH group.

Figure 4:
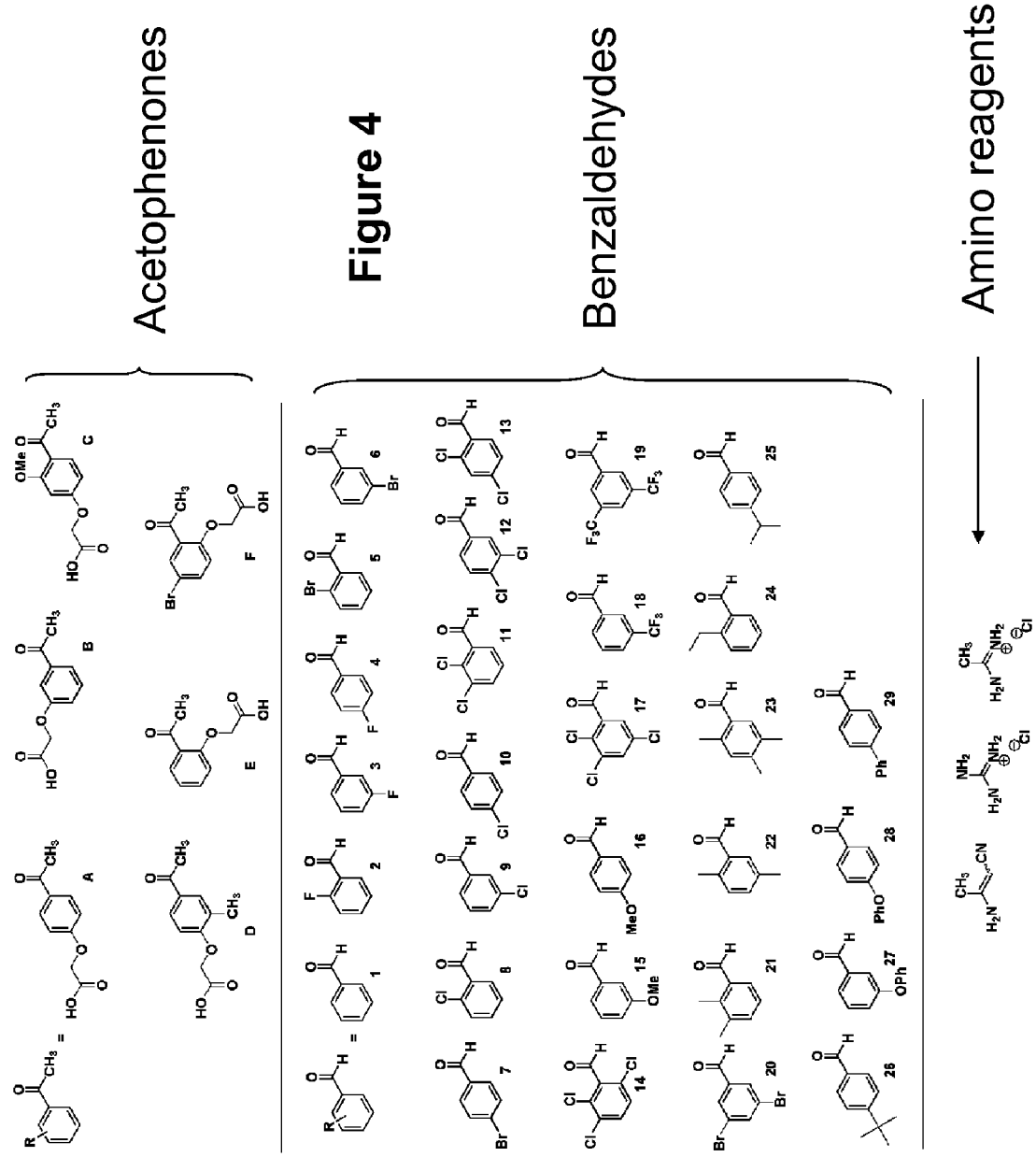
FIG. 4 provides a list of materials used in the synthetic scheme of FIG. 3 for synthesis of library members.
Figure 16:
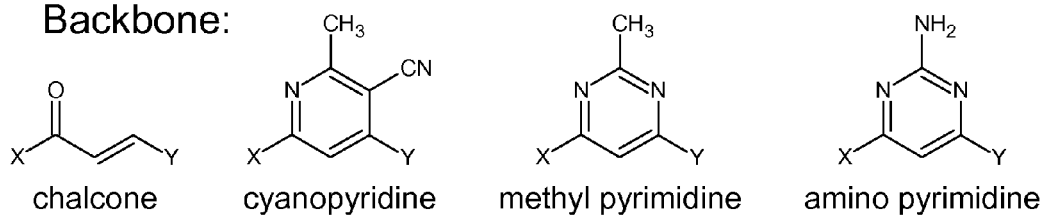
FIG. 16 illustrates the structures of a number of library members.
Figure 16:
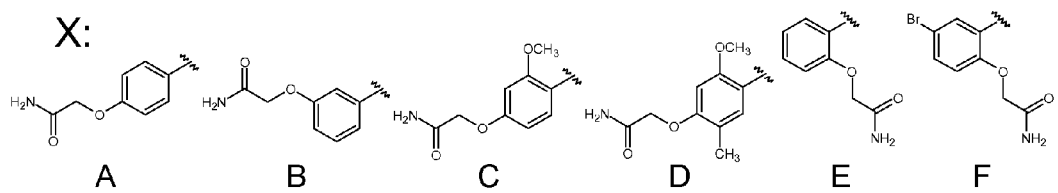
Figure 16:
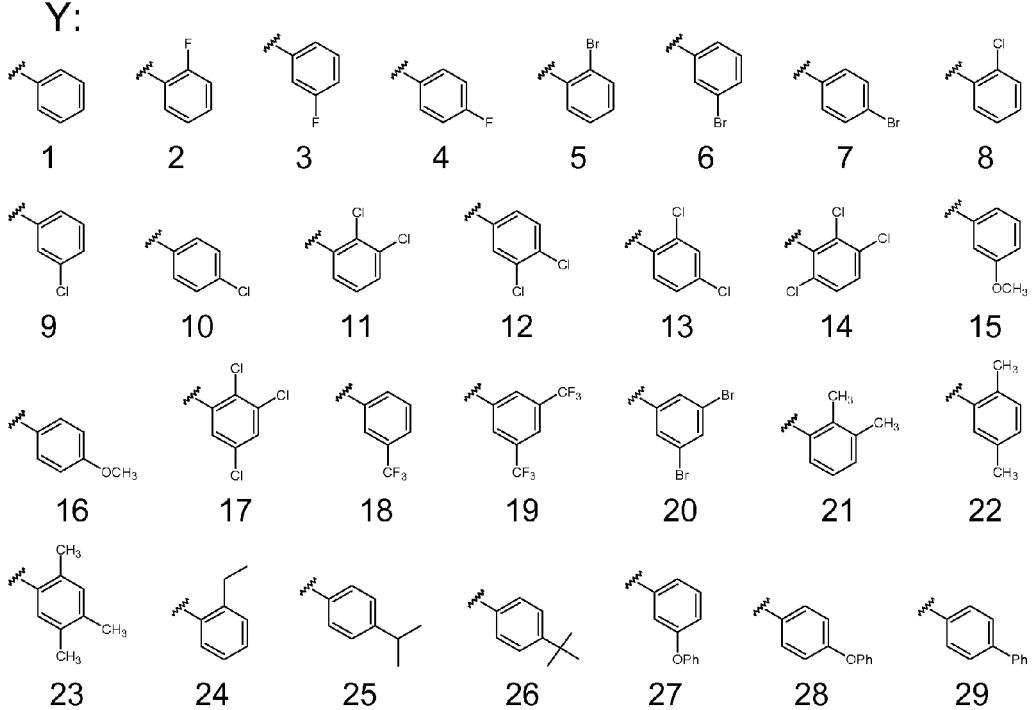

The invention provides antimicrobial, particularly antibacterial, compounds including F17, F19, F11, F12, F13, F6, B17, B19, or B14 (see FIGS. 3, 4 and 16 for naming convention).

The invention provides antimicrobial, particularly antibacterial, compounds including F5, F7, F9, F18. F26 and D27.

The invention provides antimicrobial, particularly antibacterial, compounds including F8. F10, F22, F25, E6 and B27.

In another aspect the invention provides compounds of Formula X:

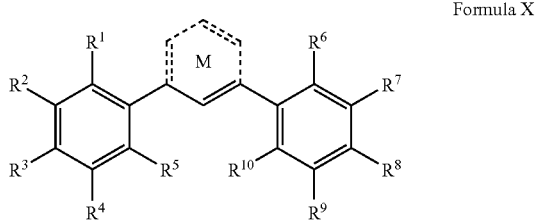

Formula X and salts, esters and solvates thereof
where:
M is

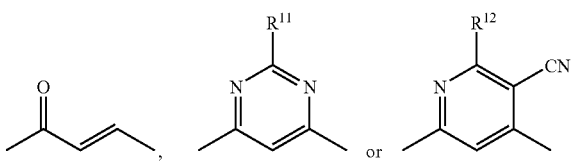

$R^{11}$ is a C1-C6 alkyl or NRR' and $R^{12}$ is $C_1$-$C_6$ alkyl and R and R' are independently selected from the group consisting of hydrogen, C1-C6 alkyl which can be substituted with one or more of halogen, C6-C13 aryl group, a C3-C8 cycloalkyl, a C3 to C10 heterocycloalkyl, (where the heteroatom(s) are N, O or S which contains 1 or 2 heteroatoms (e.g., O, N or S), or a C6-C13 aryl group which includes an C1-C6 alkyl-substituted aryl group;

at least one of $R^1$-$R^5$ is selected from

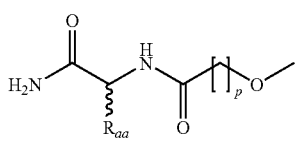

wherein p is an integer 1-6;

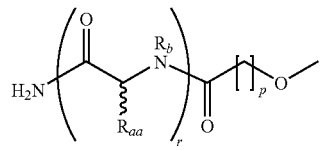

(including $NH_2$-peptide-CO—$(CH_2)p$-O—), where p is an integer from 1 to 6, r is an integer ranging from 1 to 100 and more preferably from 10 to 50, $R_{aa}$ is selected from hydrogen, C1-C8 alkyl, C1-C8 alkenyl, C1-C8 alkynyl, C6-C13 aryl, C6-C13 aralkyl, C1-C8 ether, C1-C8 thioether, C3-C8 cycloalkyl or cycloalkenyl which optionally contains one or two heteroatoms (e.g., N, O or S), and a C3-C13 heteroaromatic group having 1, 2 or 3 heteroatoms (N, O or S) all of which are optionally substituted, particularly with one or more halogens, OH, OR, SH, SR, C1-C3-alkyl, —COOH, —COO⁻, —NRR', —NRR'R", —CONRR', —NR—C(NRR')=NR, and —NR—C(NRR')=NRR'⁺, where R, R' and R" are in particular hydrogen, and C1-C3 alkyl groups; $R_b$ is hydrogen, C1-C3 alkyl or $R_{aa}$ and $R_b$ together form an optionally substituted C3-C8 cycloalkyl or cycloalkenyl which optionally contains one or two heteroatoms (e.g., N, O or S),

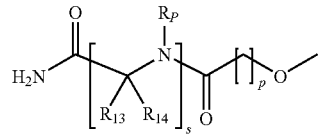

where p is 1-6, s is an integer ranging from 1 to 100 and more preferably from 10 to 50;

$R_p$ is selected from hydrogen, C1-C8 alkyl, C1-C8 alkenyl, C1-C8 alkynyl, C6-C13 aryl, C1-C8 ether, C1-C8 thioether, C3-C8 cycloalkyl or cycloalkenyl group which optionally contains one or two heteroatoms (e.g., N, O or S), and a C3-C13 heteroaromatic group having 1, 2 or 3 heteroatoms (N, O or S), all of which are optionally substituted, particularly with one or more halogens, OH, OR, SH, SR, C1-C3 alkyl, —COOH, —COO⁻, —NRR', —NRR'R", —CONRR', —NR—C(NRR')=NR, and —NR—C(NRR')=NRR'⁺, where R, R' and R" are in particular hydrogen, and C1-C3 alkyl groups; and one of $R_{13}$ or $R_{14}$ together with $R_{aa}$ form an optionally substituted C3-C8 cycloalkyl or cycloalkenyl group which optionally contains one or two heteroatoms (e.g., N, O or S);

$R_{13}$ and $R_{14}$ are independently selected from hydrogen, C1-C6 alkyl which may be substituted with one or more halogens and benzyl or phenyl optionally substituted with one or more halogens, hydroxyl or C1-C3 alkyl groups;

$R^1$-$R^{10}$ are independently selected from the group consisting of hydrogen, hydroxy, halogen, nitro, alkyl, alkenyl, alkynyl, cycloalkyl, alkoxy, aryl, aralkyl, aryloxy, arylthio, heteroaryl, heteroarylalkyl, heterocyclic, amino, aminoalkyl, aminoarylalkyl, hydroxyaminoalkyl, cycloalkylaminoalkyl, heteroarylaminoalkyl, heterocyclicaminoalkyl, hydroxyl, hydroxyalkyl, alditol, carbohydrate, polyol alkyl, —O($CH_2$)$_2$$_{(1-3)}$O—C1-C3 alkyl, polyoxyalkylene, cycloalkyloxy, cycloalkylalkoxy, haloalkoxy, arylalkoxy, heteroarylalkoxy, heterocyclicoxy, heterocyclicalkoxy, —O(C(R)$_2$)$_{1-6}$ C(O)OR, —(C(R)$_2$)$_{1-6}$C(O)NRR', amino, alkylamino, acylamino, dialkylamino, cycloalkylamino, arylamino, aralkylamino, heteroarylamino, heteroaralkylamino, heterocyclicamino, heterocyclicalkylamino, —NRR', —NH(C(R)$_2$)$_{1-6}$C(O)OR', —NRC(O)R', —NRC(O)OR', —NRC(O)SR, —NRSO$_2$NRR', —NHSO$_2$R', —NRSO2NRR', —N(C(O)NRR')$_2$, —NRSO$_2$R, —NRC(O)NRR', thiol, alkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —S(CRR')$_{1-6}$COOR, —S(CF$_2$)$_{1-6}$COOR, —SO$_2$NRR', —SO$_2$NROR, —SO$_2$NR(O)NRR', sulfonic acid, sulfonate, sulfate, sulfinic acid, sulfenic acid, cyano, tetrazol-5-yl, carboxy, —C(O)OR, —CONRR', —C(O)NR(O)R, —CONRSO$_2$R, —ONRSO$_2$NRR', —(CRR')$_{1-6}$(O)OH, —PO$_2$H$_2$, —PO$_3$H$_2$, —P(R)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, alkoxy, oxo, cyano, carboxy, carboxyalkyl, alkoxycarbonyl, and groups formed by replacing one (preferably) or more nonadjacent CH$_2$ groups of an alkyl group with an —O-(ether)-S-(thioether), —NR—, —CO—, —SO—, SO$_2$—, —NR—CO—, —NR—CO—R—, —NR—CO—O—, —CO—O—, —CO—S—, —CO—, -aryl-, -aryl-O—, -aryl-S—, -heteroaryl-, or a -heterocyclic-moiety;

two $R^1$-$R^5$ on adjacent ring carbons and/or two $R^6$-$R^{10}$ on adjacent ring carbons taken together form a 3-8 member cycloalkyl, a 3-8 member heterocyclic group having 1-3 heteroatoms (e.g., N, O and/or S), a C6-C12 aryl, a 3-8 member heteroaryl group (having 1-3 heteroatoms (e.g., N, O and/or S) optionally substituted by one or more C1-C3 alky, acyl, alkoxycarbonylalkyl, carboxyalkyl, hydroxyalkyl, aminoalkyl, aminohydroxylalkyl, hydroxy, alkyl, carboxy, hydroxyalkyl, carboxyalkyl, amino, cyano, alkoxy, alkoxycarbonyl, acyl, oxo, —NRR', cyano, carboxy, and halo.

The invention provides compounds of Formula XI:

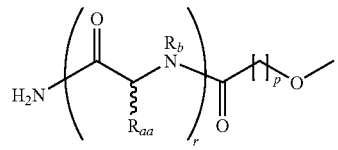

Formula XI where $R^1$-$R^{10}$ are as defined for Formula X.

In a specific embodiment of Formulas X and XI, $R^1$-$R^{10}$ groups other than those which comprise amino acid, peptide, N-substituted glycines or peptoids, are selected from halogens, hydroxyl, C1-C3 alkyl, C1-C6 haloalkyl, —COC1-C3 alkyl, phenoxy, and phenyl.

In specific embodiments of Formulas X and XI, $R^1$, $R^2$, $R^3$ or $R^6$ is selected from:

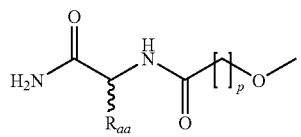

wherein p 1, 2 or 3;

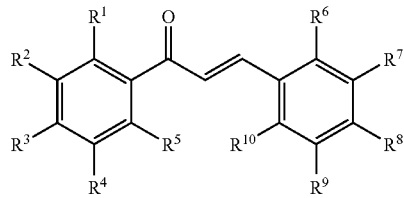

(including NH$_2$-peptide-CO—(CH$_2$)p-O—), where p is 1, 2 or 3, and r is an integer ranging from 1 to 100 and more preferably from 10 to 50, and each $R_b$ is hydrogen or linked to $R_{aa}$ and each $R_{aa}$ alone or in combination with $R_b$ are amino acids side groups of amino acids found in proteins and in particular the 20 common amino acids (Ala, Arg, Asn, Asp, Cys, Gln, Glu, Gly, His, Ile, Leu, Lys, Met, Phe, Ser, Thr, Trp, Tyr, and Val);

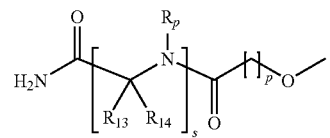

where p is 1, 2 or 3; s is an integer ranging from 1 to 100 and more preferably from 10 to 50; $R_p$ is selected from hydrogen, C1-C8 alkyl, alkenyl, or alkynyl, C6-C13 aryl, C3-C8 cycloalkyl which optionally contains one or two heteroatoms (e.g., N, O or S), an C1-C8 alkyl amino group, a C1-C8 alkylamide, —(CH$_2$)$_m$NRR', —(CH$_2$)$_m$CONRR', —(CH$_2$)$_m$—NR—C(NRR')=NR, where m is an integer ranging from 1-6, and R, R' are in particular hydrogen, and C1-C3 alkyl groups; and $R_{13}$ or $R_{14}$ are hydrogen except that one of $R_{13}$ or $R_{14}$ together with $R_p$ can form an optionally substituted C3-C8 cycloalkyl or cycloalkenyl group which optionally contains one or two heteroatoms (e.g., N, O or S);

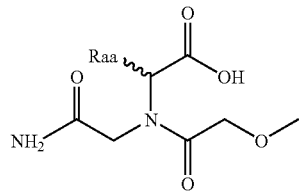

where Raa is as defined above; or

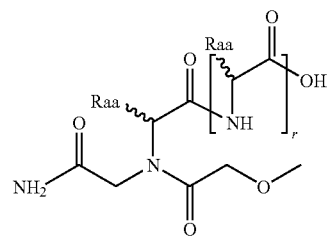

where r is an integer ranging from 1-100 (also 10-50) and Raa is as defined above.

In a specific embodiment of Formulas X and XI which contains

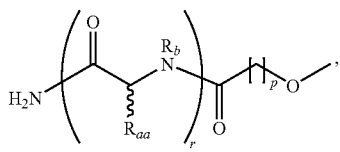

the selected $R_{aa}$ and $R_b$ form a peptide that is amphipathic, In another embodiment, the peptide formed by the combined $R_{aa}$ and $R_b$ is a host defense peptide as is known in the art. Peptides in this group may contain 1-10, 20-30, 25-40, or 50-100 amino acids, In a specific embodiment of Formulas X and XI which contains

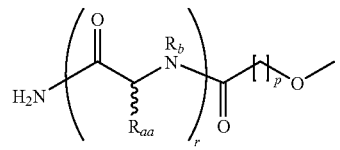

and is 10 to 50, the combined $R_{aa}$ and $R_b$ form a peptide that is amphipathic. In another embodiment, the peptide formed by the combined $R_{aa}$ and $R_b$ is a host defense peptide as is known in the art. Peptides in this group may contain 1-10, 20-30, or 25-40 amino acids.

In additional specific embodiments of Formulas X and XI which contains

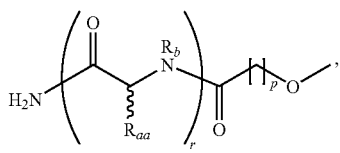

the independently selected Raa and Rb groups together form a peptide that is cationic, e.g, that is rich in Lys, Arg and/or His amino acid groups. More specifically, in an embodiment, the peptide is one wherein 50% of more of the $R_{aa}$ and Rb groups are those of cationic amino acids, for example Lys, Arg and/or His. More specifically, in an embodiment, the peptide is one wherein 75% of more of the $R_{aa}$ and Rb groups are those of cationic amino acids, for example Lys, Arg and/or His In more specific embodiments, the peptide formed has only Lys and/or Arg groups. In more specific embodiments, the peptide formed has only Lys and/or Arg groups and r is 1-10, 2-10, 3-10, 6-10 or 6-20. In more specific embodiments, the peptide formed has only His groups. In more specific embodiments, the peptide formed has only His groups and r is 1-10, 2-10, 3-10, 6-10 or 6-20. In specific embodiments, the peptides are formed from L-amino acids. In other embodiments, the peptides are formed from D-amino acids.

In additional specific embodiments of Formulas X and XI which contains

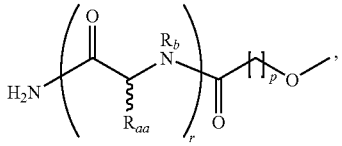

the independently selected Raa and Rb groups together form a peptide that is cationic but which has hydrophobic and/or aromatic peptide regions flanking the cationic regions. For example, the peptide can contains a poly Arg, poly Lys or poly His portion, ranging in size from 6-20 amino acids, with one or two flanking region having 2 or more, including 2-10 or 2-20, hydrophobic or aromatic amino acids. In specific embodiments, the peptides are formed from L-amino acids. In other embodiments, the peptides are formed from D-amino acids.

In any of the formulas herein where appropriate any of the variable groups can comprise a protecting group.

As used herein optional substitution means substitution with one or more non-hydrogen substituents selected from the group consisting of hydroxyl group, halide, —CN group, —NO$_2$ group, a-NH$_2$, an amine group (—NRR'), an amide group (—NR—CO—R' or —CO—NR'R), an acyl group (—CO—R), thiol, substituted or unsubstituted C1-C6 alkyl, akenyl or alkynyl groups, substituted or unsubstituted C6-C13 aryl groups, substituted or unsubstituted C1-C6 alkoxy groups, substituted or unsubstituted C6-C13 aryloxy groups, substituted or unsubstituted C3-C12 heterocyclic groups where the heteroatoms are N, O or S. Non-hydrogen substitution for substituents mean substitution with one or more non-hydrogen groups selected from hydroxyl, halogen, —CN, —NO$_2$, —NR"R"', unsubstituted C1-C3 alkyl, unsubstituted phenyl or benzyl groups.

In the above definitions, R and R' are selected from hydrogen, C1-C6 alkyl (preferably C1-C3 alkyl), C3-C8 cycloalkyl, C4-C8 heterocycloalkyl (heteroatom=N, O or S), and C6-C13 aryl; and R" and R"' are selected from hydrogen, C1-C6 alkyl (preferably C1-C3 alkyl), C3-C8 cycloalkyl, C4-C8 heterocycloalkyl (heteroatom=N, O or S), and C6-C13 aryl.

In addition, hereinafter, the following definitions apply:

As used herein, the term "array" refers to an ordered arrangement of structural elements, such as an ordered arrangement of individually addressed and spatially localized elements. Arrays useful in the present invention include arrays of containment structures and/or containment regions, such as fluid containment structures or regions, provided in a preselected, spatially organized manner. In some embodiments, for example, different containment structures and/or regions in an array are physically separated from each other and hold preselected materials, such as the reactants and/or products of chemical reactions, for example candidate compounds for screening of antimicrobial activity.

Arrays of the present invention include "microarrays" and "macroarrays" which comprise an ordered arrangement of containment structures and/or containment regions capable of providing, confining and/or holding reactants, products, solvent and/or catalysts corresponding to one or more chemical reactions, reaction conditions and/or screening conditions. In some embodiments, a portion of the reactants and/or products confined in a containment structure/region of a microarray or macroarray are immobilized, for example by spatially localized conjugation to a selected region of containment structure or region. Microarrays and macroarrays of the present invention, for example, are capable of providing an organized arrangement of containment structures and/or regions, wherein different containment structures and/or regions are useful for providing, confining and/or holding preselected combinations of reactants, products and/or candidate compounds having well defined and selected compositions, concentrations and phases. Containment structures and/or regions of microarrays and macroarrays are also useful for providing, confining and/or holding the products of chemical reactions. In some embodiments, for example, each containment structure and/or region of the microarrays and macroarrays is physically separated and contains the product of a different chemical reaction or a chemical reaction carried out under different reaction conditions.

The terms "microarray" and "macroarray" are used herein in a manner consist with the art. In some embodiments, a microarray comprises a plurality of containment structures or regions having at least one microsized (e.g., 1 to 1000s of microns) or sub-microsized (e.g., less than 1 micron) physical dimension. In some contexts, containment structures/regions of a microarray are smaller than containment structures/regions of a macroarray. In some contexts, containment structures/regions of a microarray are provided in a higher density than containment structures/regions of a macroarray. In some contexts, the number of containment structures/regions of a microarray is larger than the number of containment structures/regions of a macroarray. In specific embodiments, the invention provides macroarrays produced by SPOT synthesis are described herein and as known in the art. Macroarrays in the context of the present invention which are arrays of candidate compound for screening are prepared such that each compound member of the array (each spatially-localized compound) is present in an amount sufficient to allow its removal form the array for further analysis, for example, to measure spectral properties or to obtain confirmatory structural analysis (e.g., by mass spectroscopic analysis or NMR analysis). As will be understood by one having ordinary skill in the art may different microarray and macroarray formats are useable in the present invention including, but not limited to, standard 96, 384 or 1536 microarray configurations.

As defined herein, "contacting" means that a compound used in the present invention is provided such that is capable of making physical contact with another element, such as a microorganism, a microbial culture or a substrate. In another embodiment, the term "contacting" means that the compound used in the present invention is introduced into a subject receiving treatment, and the compound is allowed to come in contact in vivo.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxyl group is an alkyl group linked to oxygen and can be represented by the formula R—O.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl having one or more hydrogens replaced with one or more fluorine atoms, chlorine atoms, bromine atoms and/ or iodine atoms.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:
—COOR where R is a hydrogen or an alkyl group or an aryl group and more specifically where R is methyl, ethyl, propyl, butyl, or phenyl groups all of which are optionally substituted;
—COR where R is a hydrogen, or an alkyl group or an aryl groups and more specifically where R is methyl, ethyl, propyl, butyl, or phenyl groups all of which groups are optionally substituted;
—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;
—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds;
—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;
—OCOOR where R is an alkyl group or an aryl groups;
—SO$_2$N(R)$_2$ where R is a hydrogen, an alkyl group, or an aryl group and R and R can form a ring;
—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

Pharmaceutically acceptable salts comprise pharmaceutically-acceptable anions and/or cations. Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$_4^+$) and substituted ammonium (N(R')$_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Cl$^-$, Br$^-$), sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

The compounds of this invention may contain one or more chiral centers. Accordingly, this invention is intended to include racemic mixtures, diasteromers, enantiomers and mixture enriched in one or more steroisomer. The scope of the invention as described and claimed encompasses the racemic forms of the compounds as well as the individual enantiomers and non-racemic mixtures thereof.

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

As used herein, the term "treating" includes preventative as well as disorder remittent treatment. As used herein, the terms "reducing", "suppressing" and "inhibiting" have their commonly understood meaning of lessening or decreasing.

In certain embodiments, the present invention encompasses administering the compounds useful in the present invention to a patient or subject. A "patient" or "subject", used equivalently herein, refers to an animal. In particular, an animal refers to a mammal, preferably a human. The subject either: (1) has a condition remediable or treatable by administration of a compound of the invention; or (2) is susceptible to a condition that is preventable by administering a compound of this invention.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The inventors have a developed an expedient approach to synthesize and screen focused parallel libraries prepared in a macroarray format for antibacterial behavior. Using this format, the inventors have discovered several new antibacterial agents, some of which are comparable to linezolid with respect to antibacterial activity. The inventors have discovered a new structure class for antibacterial compounds that displays excellent activity against S. aureus.

Figure 2:
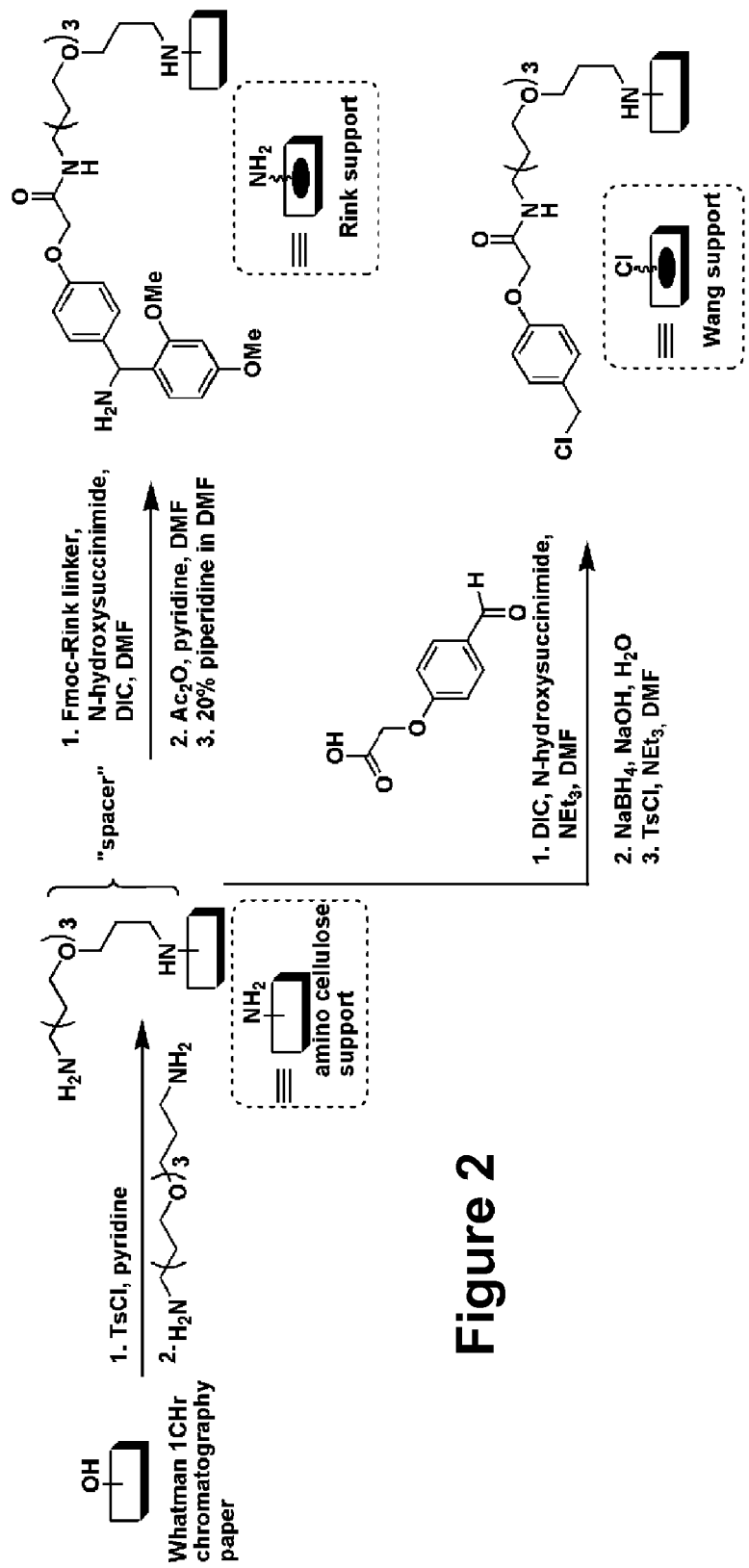
FIG. 2 provides a synthetic scheme showing Rink and Wang linking routes.

Cellulose paper is a robust, easy-to-manipulate support for the synthesis of macroarrays of chalcones and chalcone derived heterocycles (FIG. 2). Bowman, M. D.; Jacobson, M. M.; Pujanauski, B. G.; Blackwell, H. E. Tetrahedron 2006, 62, 4715-4727.

To further expand the utility of this platform, the synthesis of the macroarrays was coupled with high throughput screening techniques. Antimicrobial cationic peptides had been previously prepared by the SPOT-synthesis technique and subsequently screened to find inhibitors at the μg/mL range. Hilpert, K.; Volkmer-Engert, R.; Walter, T.; Hancock, R. E. W. Nature Biotechnology 2005, 23, 1008-1012. Encouraged by this work and previously published accounts of the antibacterial activity of chalcones, the inventors looked at the synthesis and the screening of small molecules by both on-support and solution-based assays. Nielsen, S. F.; Larsen, M.; Boesen, T.; Schønning, K.; Kromann, H. J. Med. Chem. 2005, 48, 2667-2677; Nielsen, S. F; Boesen, T.; Larsen, M.; Schønning, K.; Kromann, H. Biorganic Medicinal Chemistry 2004, 12, 3047-3054; Bowden, K. Dal Pozzo, A.; Duah, C. K. J. Chem. Res. (S) 1990, 12, 2801-2830.

The invention may be further understood by the following non-limiting examples:

EXAMPLE 1

Synthesis of Libraries Employing Rink Linkers

FIG. 1 illustrates a general schematic of small molecule macroarray library construction and screening. In order to improve coupling efficiency of the initial building blocks and expand the set of possible building blocks used in library construction, we chose to explore the use of the well-characterized Rink-amide linker system. Bernatowicz, M. S.; Kearney, T.; Neves, R. S.; Koster, H., An Efficient Method for Racemization Free Attachment of 9-Fluorenylmethyloxycarbonyl-Amino Acids to Peptide-Synthesis Supports. Tetrahedron Lett. 1989, 30, 4341-4344; Rink, H., Solid-phase synthesis of protected peptide fragments using a trialkoxydiphenyl-methyl ester resin. Tetrahedron Lett. 1987, 28, 3787-90. FIG. 2 illustrates the generation of the Rink linker on planar cellulose substrate (e.g., chromatography paper). The figure shows a comparison to the Wang linker used in previous work (WO08/016,738).

It was reasoned that the use of this system would circumvent some of the problems that are associated with using the Wang linker system to construct small molecule macroarrays. One main advantage of using the Rink linker system is the relatively mild conditions required (standard diisopropylcarbodiimide (DIC) coupling conditions) for coupling the Rink linker to the amino-cellulose support. These conditions are beneficial as they permit the support to stay robust throughout the entire macroarray construction, making it easier to perform syntheses and on-support biological assays post cleavage. Furthermore, we found the Rink linker support to be highly stable, as the support could be prepared and used after sitting on the bench-top for several weeks. This Rink linker strategy also reduces the number of synthetic steps needed to generate a linker suitable for substrate attachment, as an Fmoc-Rink-amide linker can be attached and deprotected in three high-yielding steps. Also, the Rink linker is acid labile, so similar cleavage conditions (TFA vapor) can be used as previously described for the Wang linker system.

Blackwell et al. has previously had success attaching initial building blocks to Rink linker-derivatized cellulose support using standard peptide coupling reagents. Lin, Q.; O'Neill, J. C.; Blackwell, H. E., Small molecule macroarray construction via Ugi four-component reactions. Org. Lett. 2005, 7, 4455-4458. Using Fmoc-Rink-amide linker and amino-cellulose support, Rink support was prepared with a coupling efficiency of ~75%. All coupling efficiencies were quantified using standard UV-Fmoc analysis. Carpino, L. A.; Han, G. Y., 9-Fluorenylmethoxycarbonyl Amino-Protecting Group. J. Org. Chem. 1972, 37, 3404. Because of the relative expense of the Fmoc-Rink-amide linker, it was "spotted" (along with coupling reagents) onto the amino-cellulose support, in contrast to the blanket functionalization used with the Wang linker system. Bowman, M. D.; Jacobson, M. M.; Blackwell, H. E., Discovery of fluorescent cyanopyridine and deazalumazine dyes using small molecule macroarrays. Org. Lett. 2006, 8, 1645-1648. We observed a dramatic improvement in the coupling efficiency of the Rink linker compared to previous results with the Wang linker system (75% vs. 15%), especially since the spotting approach employed relied on the use of significantly less linker material.

In order to attach the acetophenones to the Rink linker, bromoacetic acid (BrAcOH) could be attached using standard DIC coupling conditions, followed by displacement of the bromide by an amino acetophenone. Hydroxyacetophenones however, would still need to be subjected to a KOtBu/DMF solution, in which we found certain hydroxyacetophenones to be insoluble. In order to overcome these solubility problems, the hydroxyacetophenones could first be converted into acetyl-phenoxyacetic acids via $S_N2$ reaction with methyl bromoacetate and subsequent saponification. These acetyl-phenoxyacetic acids could be directly attached to the Rink-amide linker via a DIC coupling reaction at room temperature to produce support-bound acetophenones, which were then available for further derivatization reactions. Coupling of the acetyl-phenoxyacetic acids to the Rink support proceeded with excellent purity (>95% as determined by HPLC analysis) and modest conversion (60-90% as determined by HPLC analysis). We found that this reaction step could be performed at lower temperatures (43° C.) relative to the Wang linker support (80° C.), which was advantageous as we had observed that multiple reactions at high temperatures "wrinkled" the cellulose support, making it incompatible with on-support biological assays.

With the acetophenones attached to the Rink linker support, we needed to determine if the same reaction conditions used for the Claisen-Schmidt condensation (benzaldehyde spotted 3× in 1.5 M KOH in 50% EtOH/$H_2O$, 80° C., 10 min) would be compatible with the Rink linker system. Before it would be practical to construct larger macroarrays, it was beneficial to optimize the Claisen-Schmidt condensation reaction on the planar array. Initial results from small test libraries had indicated low purities (<60% as determined by HPLC analysis) for the corresponding "Rink" chalcones after TFA cleavage. After several optimization attempts, we found that performing the reaction at a lower temperature (43° C.) resulted in the best reaction conversion and purity of the corresponding Rink support bound chalcones (>85% as determined by HPLC analysis) after TFA cleavage. Again, the low reaction temperatures also helped to preserve the robustness of the cellulose support.

With the optimized reaction conditions in hand, we proceeded to construct a small molecule macroarray of chalcone derivatives. This library was designed to validate the utility of the Rink system as an improved platform for small molecule macroarray construction, compared to the previous Wang linker system. Acetophenone and benzaldehyde building blocks as shown in FIG. 4 where chosen for preparing a library of chalcones as shown in FIG. 3. Pyrimidine and pyridine heterocycle derivatives of chalcones were synthesized using previously reported reaction conditions (see FIG. 3). Bowman, M. D.; O'Neill, J. C.; Stringer, J. R.; Blackwell, H. E., Rapid Identification of Antibacterial Agents Effective against *Staphylococcus aureus* Using Small-Molecule Macroarrays. *Chem. Biol.* 2007, 14, 351-357; see also WO 2008/016738.

Libraries containing 174 chalcones, 174 cyanopyridines, and 24 pyrimidines were synthesized on a planar cellulose support system (FIG. 3). LC-MS analyses of a subset of the total compounds (20%) cleaved from the macroarray showed good to excellent purities (80-99%).

Figure 5:
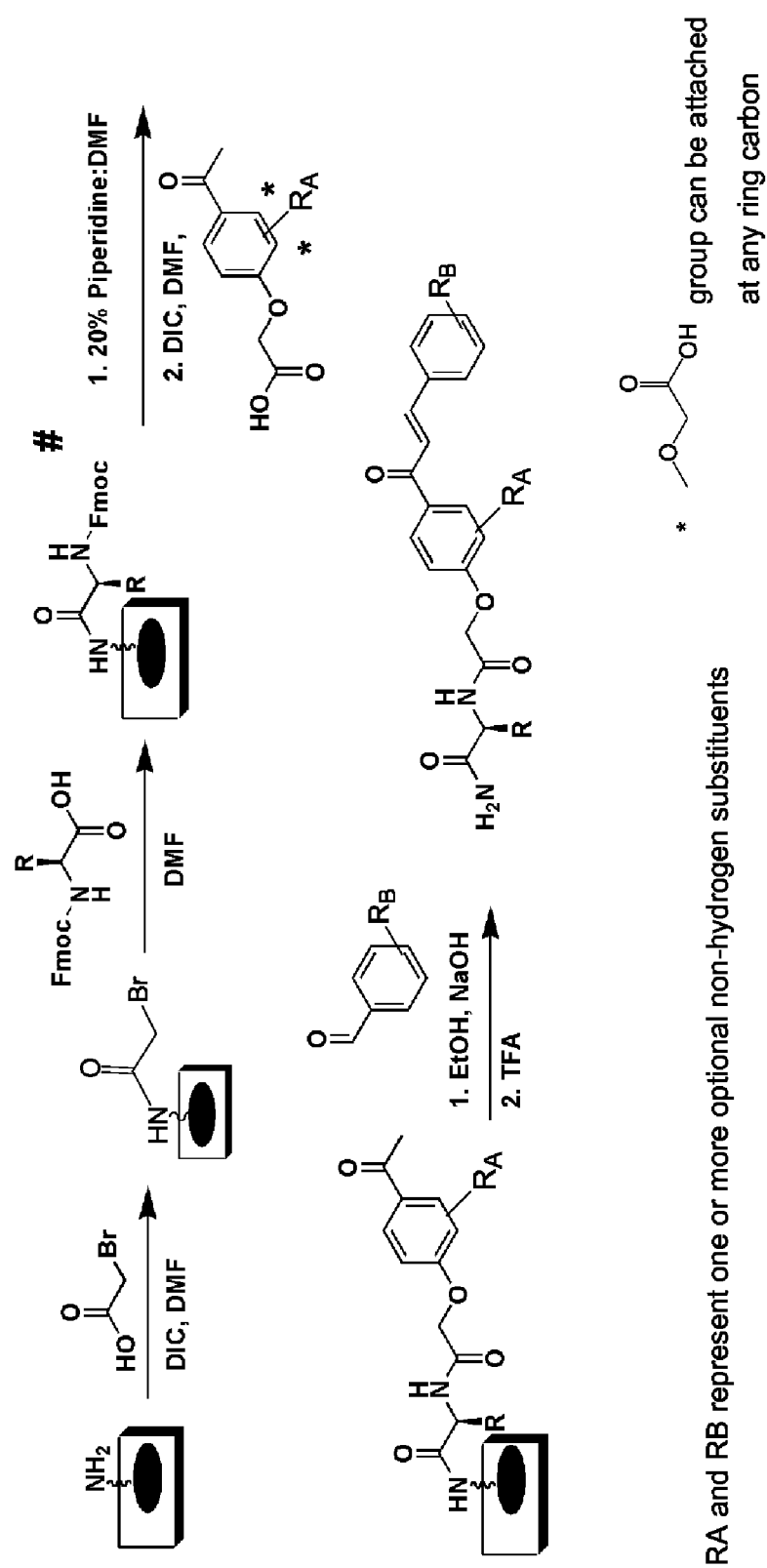
FIG. 5 provides a synthetic scheme showing a pathway for chalcone/peptide synthesis.
Figure 6:
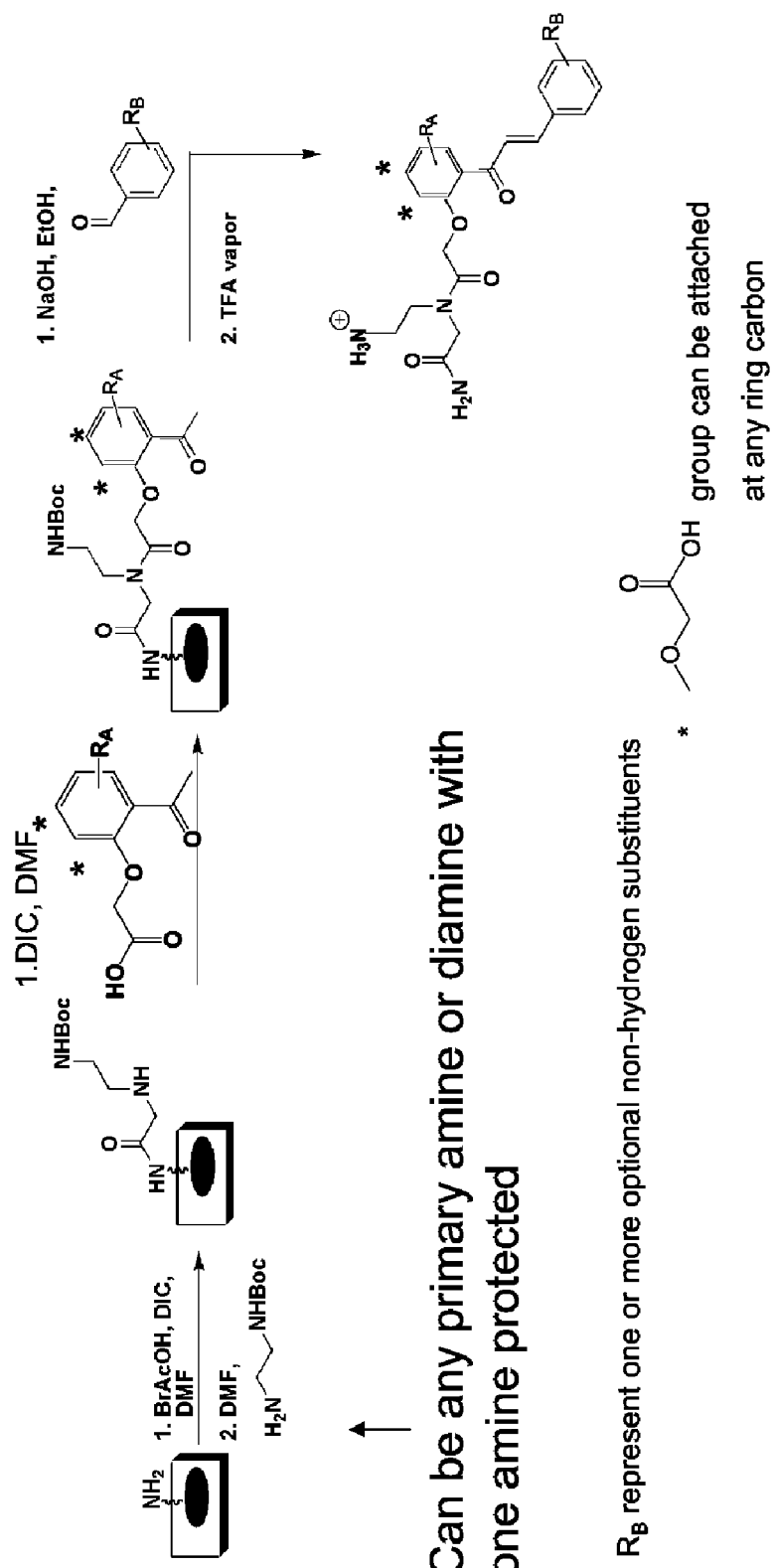
FIG. 6 provides a synthetic scheme showing a pathway for peptoid/chalcone synthesis.
Figure 7:
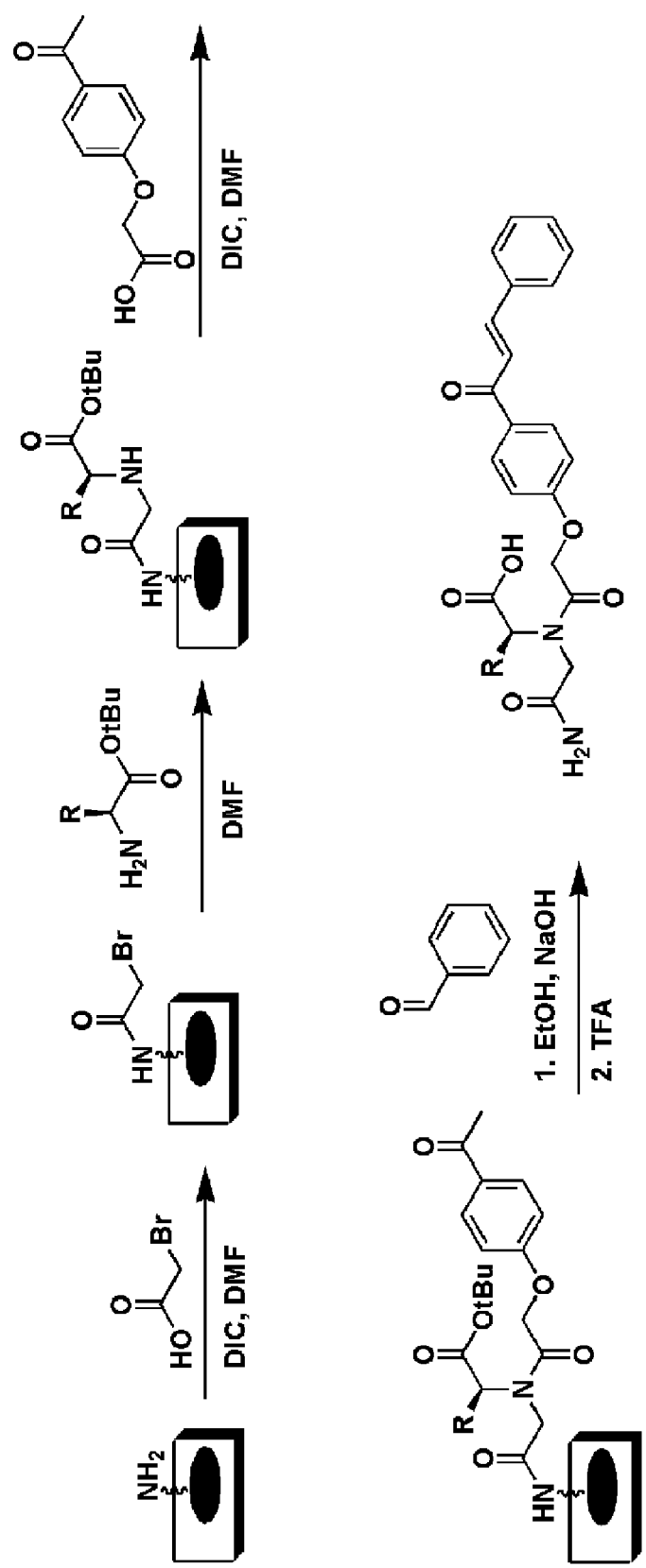
FIG. 7 provides a synthetic scheme showing an alternative pathway for peptide synthesis.

FIGS. 5-7 illustrate one advantage of the use of the Rink linker for array synthesis in that it can be used to attach amino acids, peptides, N-substituted glycines or peptoids (oligomers of N-substituted glycines) to the chalcone backbone. FIG. 5 illustrates addition of a N-protected amino acid to the Rink linker followed by reaction with an acetophenone (as described above, exemplary acetophenones listed in FIG. 4).

Thereafter the benzaldehyde (as described above, exemplary benzaldehydes listed in FIG. 4) is reacted with the attached acetophenone to form the chalcone. As illustrated the chalcone derivatized with the amino acid can be released from the substrate. Also as illustrated in FIG. 5 multiple amino acids can be added at point "#" in the synthesis using standard solid-phase peptide synthesis. The R group of the amino acid can in general be any group that does not interfere with the chemistry illustrated in FIG. 5. As is known in the art certain R groups that might be sensitive or interfere with the chemistry shown may be provided with protective groups. A wide variety of protective groups is known in the art and one of ordinary skill in the art understands how to chose a protective group useful for a given set of reaction conditions.

FIG. 6 illustrates attachment of an N-substituted glycine to a chalcone backbone. The Rink linker is first reacted as illustrated in FIG. 6 with bromoacetic acid to form a solid attached bromoacetamide which in turn is reacted with a primary amine (most generally $NH_2$—$R_p$, see formulas above for exemplary definition of $R_b$) forming an N-substituted glycine on the solid. The primary amine may be a diamine (as illustrated) a triaminer or a polyamine, in each case the additional amine groups in the $R_b$ group must be protected during synthesis). Steps 1 and 2 of FIG. 6 can be repeated to form a peptoid on the solid, e.g.:

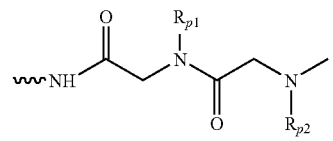

The unprotect amine group attached to the solid is then reacted with the acetophenone as described above and thereafter reacted with the benzaldehyde to form the chalcone. FIG. 7 illustrates an alternative peptide synthesis combined with chalcone formation on a solid. In this case an O-protected amino acid (e.g., using OtBu protecting group) is reacted with bromo acetamide on the solid. The unprotected NH of the attached amino acid is then reacted with the acetophenone followed by reaction with the benzaldehyde to form the chalcone. Peptide synthesis can be continued after deprotection of the O-tBu group (other appropriate protecting groups can be used) either before or after chalcone formation. In all of FIGS. 5-7, the chalcone formed can be further reacted as illustrated in FIG. 3 to form cyanopyridines and pyrimidines.

EXAMPLE 2

Solution Phase Synthesis of Rink Acetophenones and Rink Chalcones

As previously discussed, the acetophenones used in macroarray construction required a carboxylic acid functionality for attachment to the Rink amide linker. To efficiently install this moiety, a general synthetic scheme was designed to derivatize a variety of acetophenones (Scheme 1). An acetophenone was reacted with methyl bromo acetate in the presence of potassium carbonate ($K_2CO_3$), and the product was isolated by precipitation from water. Hydrolysis of the ester with NaOH in $H_2O$/THF afforded the acetyl-phenoxyacetic acid carboxylic acid in excellent purity.

Scheme 1: Solution phase synthesis of acetyl-phenoxyacetic acids

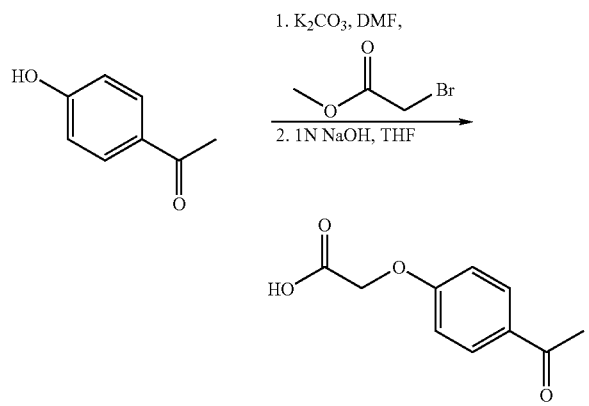

In order to estimate the loadings of individual macroarray members, the corresponding acetophenones were cleaved from the macroarray and analyzed by HPLC analysis. An accurate calibration curve was needed for each acetophenone building block to estimate the loading of each macroarray member. Initial attempts at solid phase synthesis of the desired control compounds resulted in low purities and low yields (data not shown), therefore a solution-phase method was pursued.

An acetophenone was reacted with commercially available 2-bromoacetamide in the presence of $K_2CO_3$, with the product precipitating out after addition of the reaction mixture to water. This solution-phase reaction produced the desired "Rink" acetophenone acid in high yield (70-90%) and excellent purity; allowing for calibration curve generation.

EXAMPLE 3

Lead Compound Re-synthesis

Once active compounds had been identified in the biological assays (as described under Aim 2), they were synthesized in solution to obtain an authentic sample for characterization and further biological evaluation. As some of the active chalcones were similar in structure to our previously reported active chalcones synthesized with the Wang linker[43], our initial synthetic route was aimed at generating the chalcone first, followed by an $S_N2$ reaction with 2-bromoacetamide. Although this short synthesis allowed us to obtain the desired chalcone in sufficient quantities after several re-crystallizations, an alternate synthesis was devised to increase reaction yields and decrease purification time.

Scheme 2: Solution-phase synthesis of chalcones

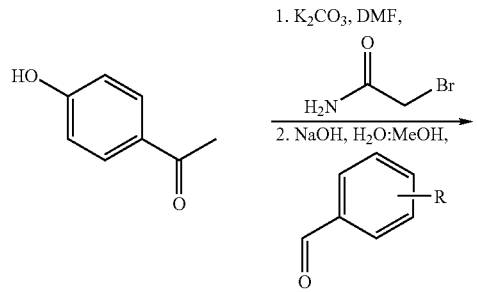

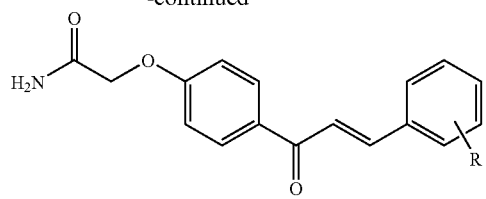

We found that our solution-phase synthesis of Rink acetophenones could be modified to yield our target chalcones in moderate yields and high purities (Scheme 2). The high purities were attributed to the careful choice of solvent used in the Claisen-Schmidt condensation between the Rink acetophenone and an aldehyde. After dissolving the Rink acetophenone and benzaldehyde in a 1:1 $H_2O$:MeOH mixture, 100 uL of a 1:1 (w:v) NaOH:$H_2O$ solution was added with the chalcone product precipitating out of solution. Purification was thus greatly simplified (no re-crystallization or column chromatography required), as the precipitate was simply filtered and washed several times with a 1:1 $H_2O$:MeOH solution to afford the desired Rink chalcone product in excellent purity.

In order to verify that solution phase synthesis affords only the trans chalcone product, a $^1H$ NMR spectrum was analyzed by measuring the coupling constants of the two vinylic protons present in the $\alpha,\beta$-unsaturated enone moiety. Only one set of vinylic proton peaks were observed and these had coupling constants ranging from 16-17 Hz, indicating a trans double bond. In order to rule out the possibility of the vinylic proton peaks of the cis isomer being obscured or overlapping with other aromatic peaks in the $^1H$ NMR spectrum, the solution phase Rink chalcones were subjected to LC-MS analysis, which indicated the presence of only 1 peak at 254 nm, thus confirming our initial hypothesis that the trans chalcone is formed when solution phase synthesis is employed.

It was important to determine which isomers (trans or cis) were produced in the our solution phase Rink chalcone synthesis because it had been previously reported that the trans chalcone isomer is responsible for the antimicrobial activity, while the cis isomer was virtually inactive. Larsen, M.; Kromann, H.; Kharazmi, A.; Nielsen, S. F., Conformationally restricted anti-plasmodial chalcones. *Bioorg. Med. Chem. Lett.* 2005, 15, 4858-4861.

Although the double bond of the chalcone is prone to photoisomerization under certain conditions, it is difficult to predict the rate and extent of isomerization for individual chalcones because it is highly dependent on a variety of factors including solvent and type of substitution on aromatic rings. Larsen et al. 2005. The activity results observed for the chalcones may be affected by some level of isomerization of the chalcones.

EXAMPLE 4

Antibacterial Screening

After preparation of the small molecule macroarray, we examined several methods for analyzing the antibacterial activity of individual compounds on the macroarray. Our first plan was to analyze each compound using a standard Kirby-Bauer disk diffusion assay. However, this assay gave only a qualitative assessment of antibacterial activity and furthermore, all of the compound was consumed in the assay.

Next examined was a solution-based assay that consisted of "punching out" individual spots from the macroarray with a standard desktop hole-punch, cleaving the compound in the presence of TFA vapor, and eluting with acetonitrile, and generating stock solutions in DMSO to test antibacterial activity. This procedure allowed for evaluation of antibacterial activity using a minimal amount of compound in a solution-based antibacterial assay, while the remaining compound could be used in HPLC analysis. This allowed direct assessment of the purity of compounds that were used in the solution-based antibacterial assay.

Figure 8:
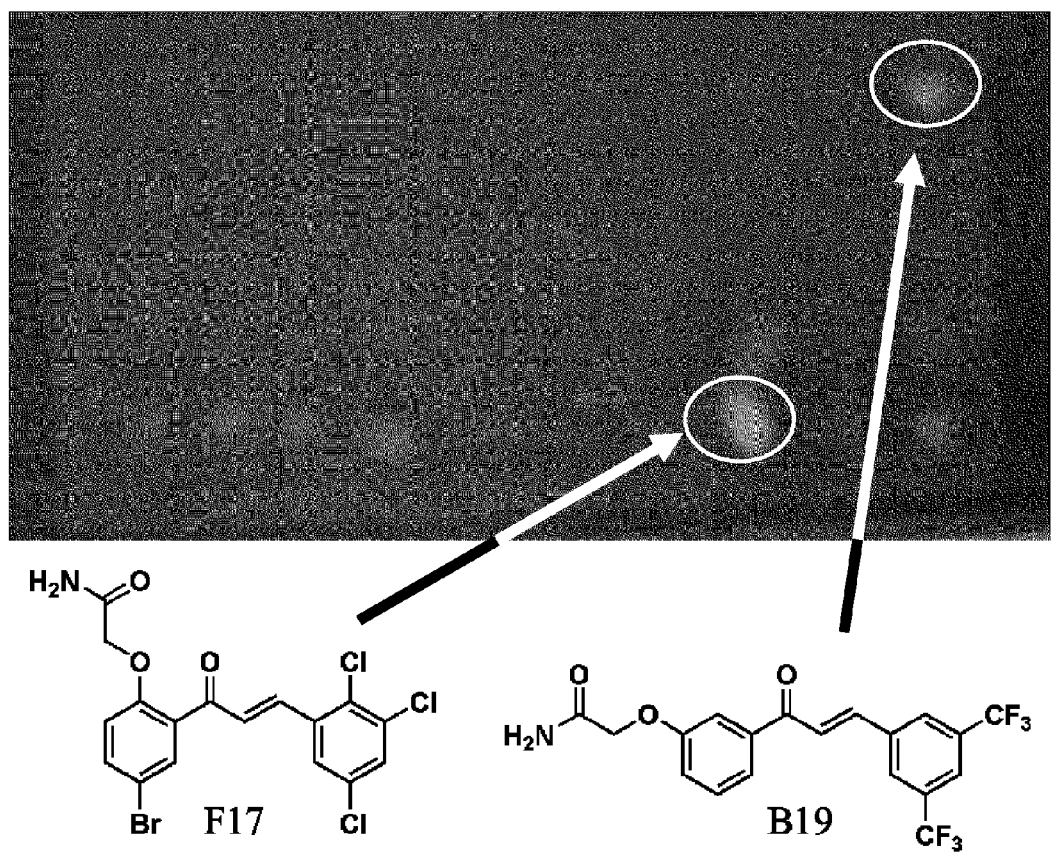
FIG. 8 shows an image of a TTC-stained agar-overlay assay showing active chalcones F17 and B19.
Figure 9:
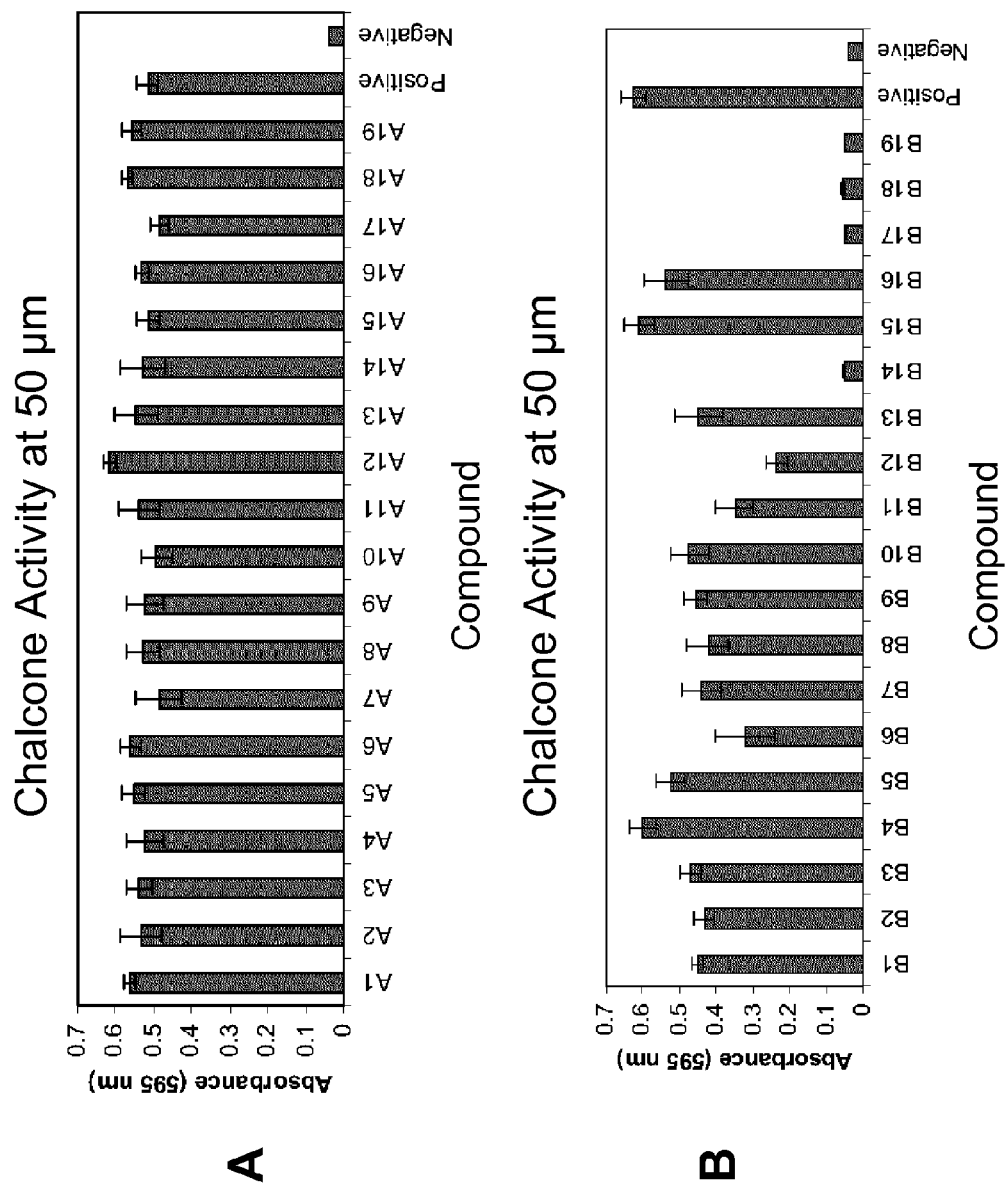
FIGS. 9A through 9O provide data showing the activity of chalcone library members.
Figure 9:
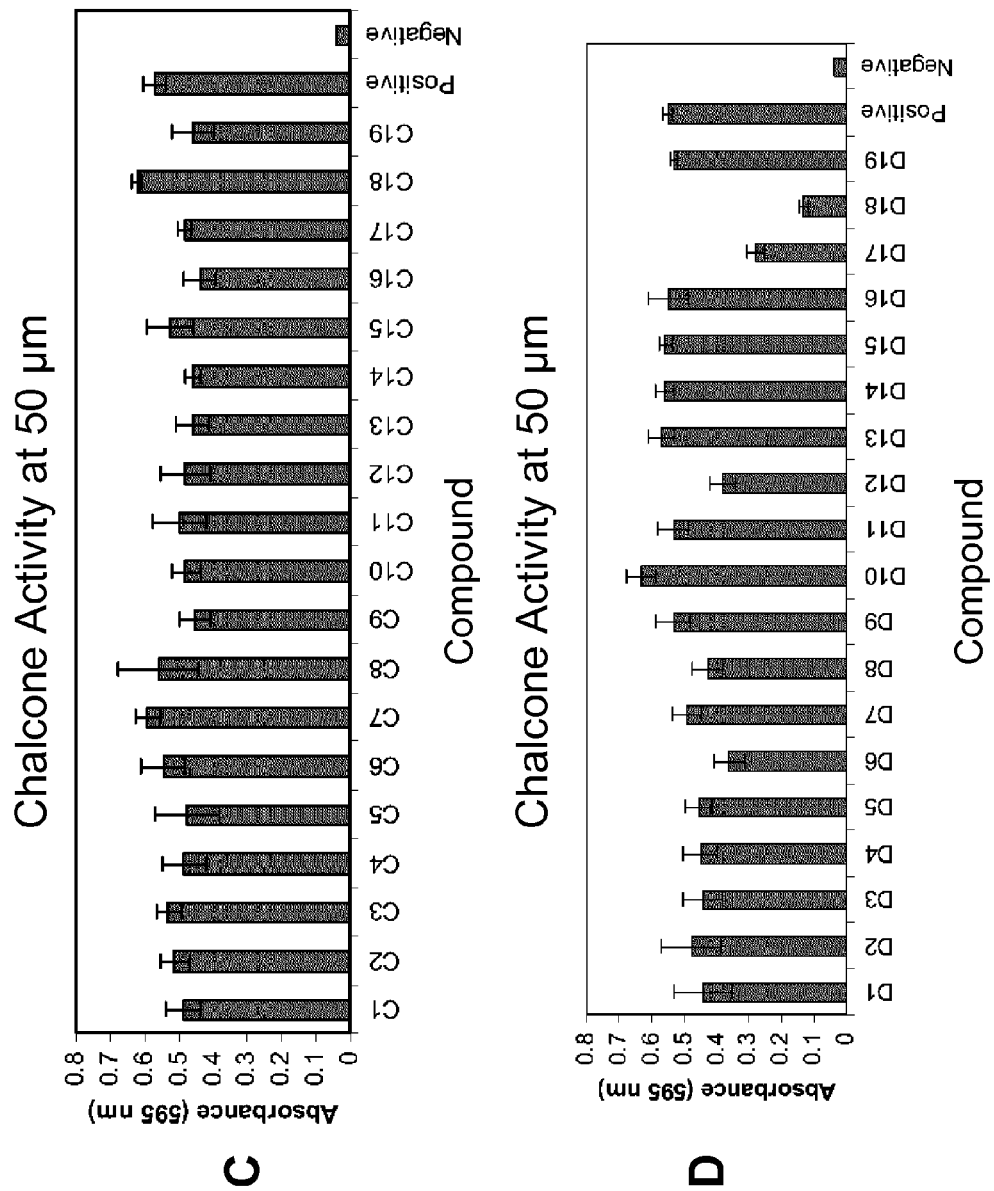
Figure 9:
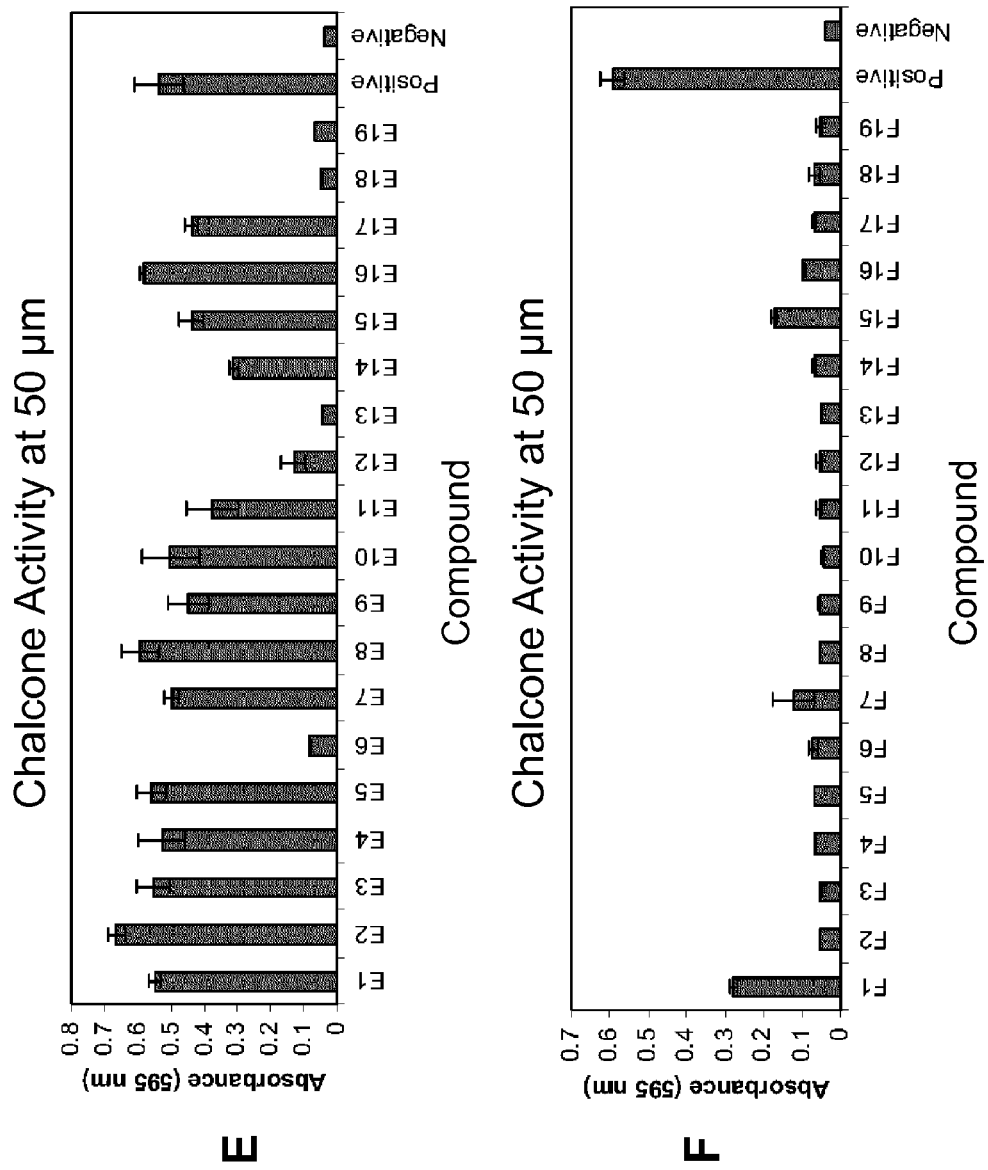
Figure 9:
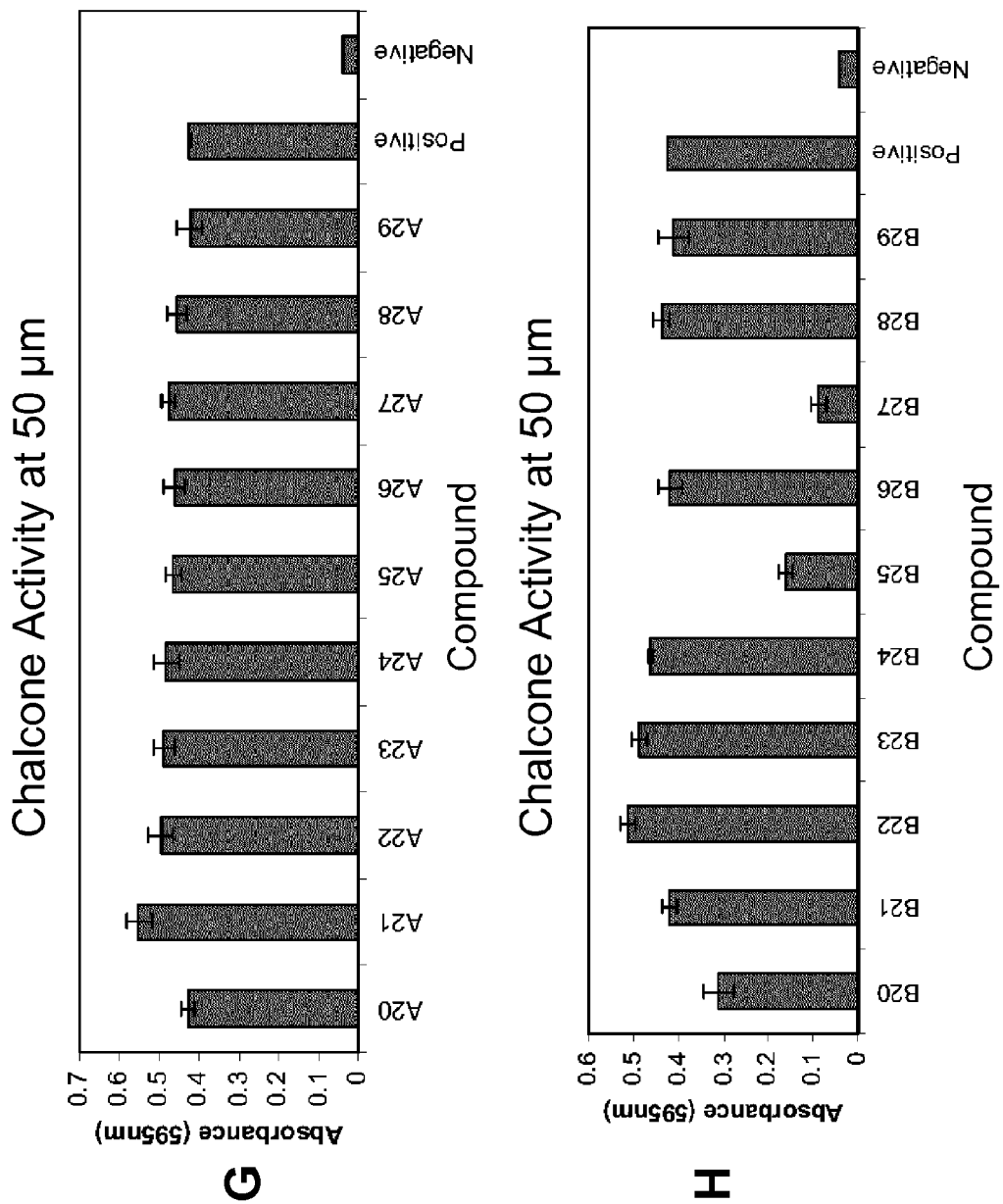
Figure 9:
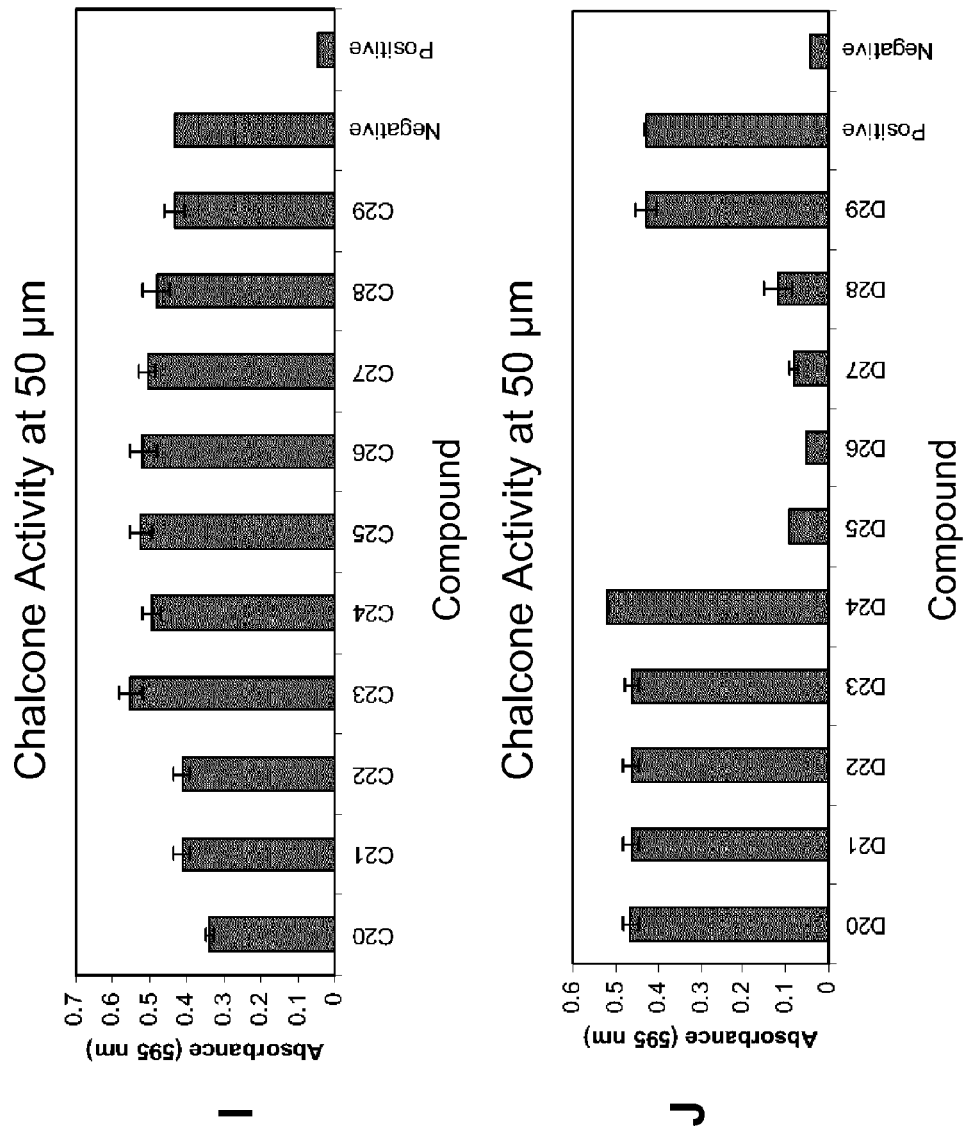
Figure 9:
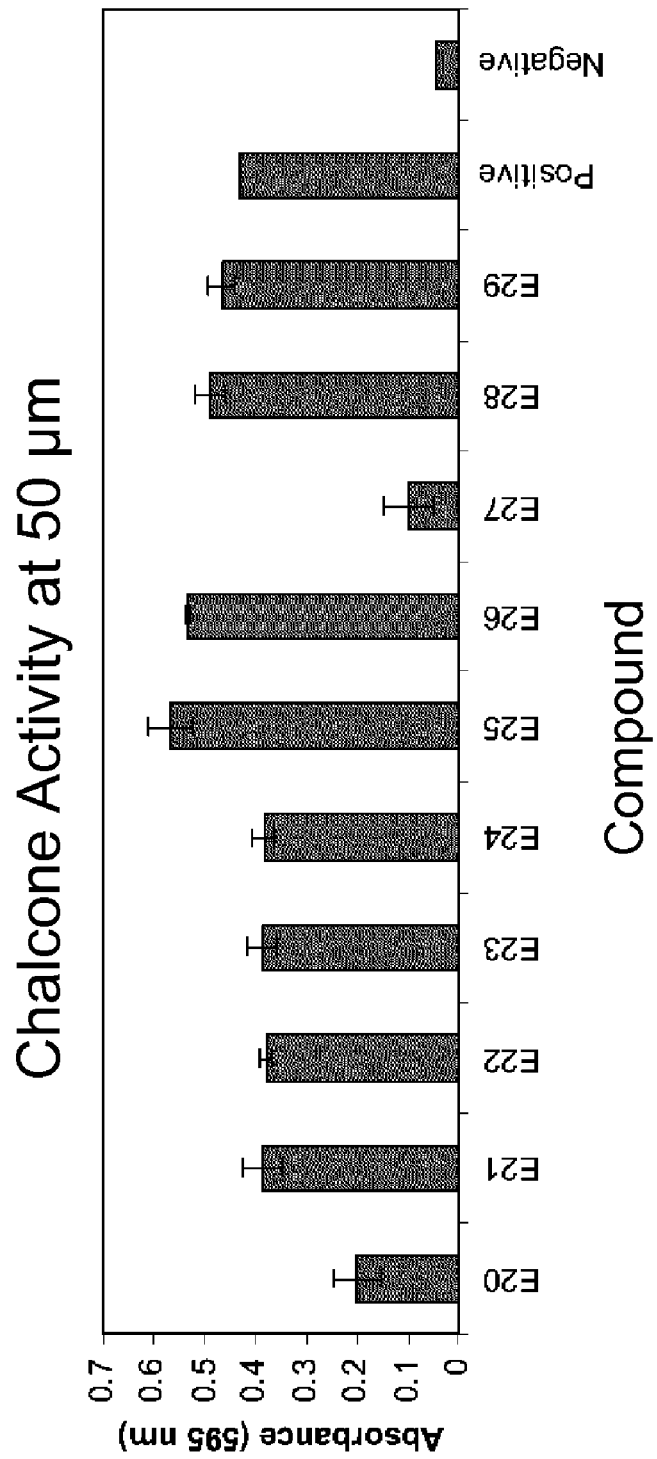
Figure 9:
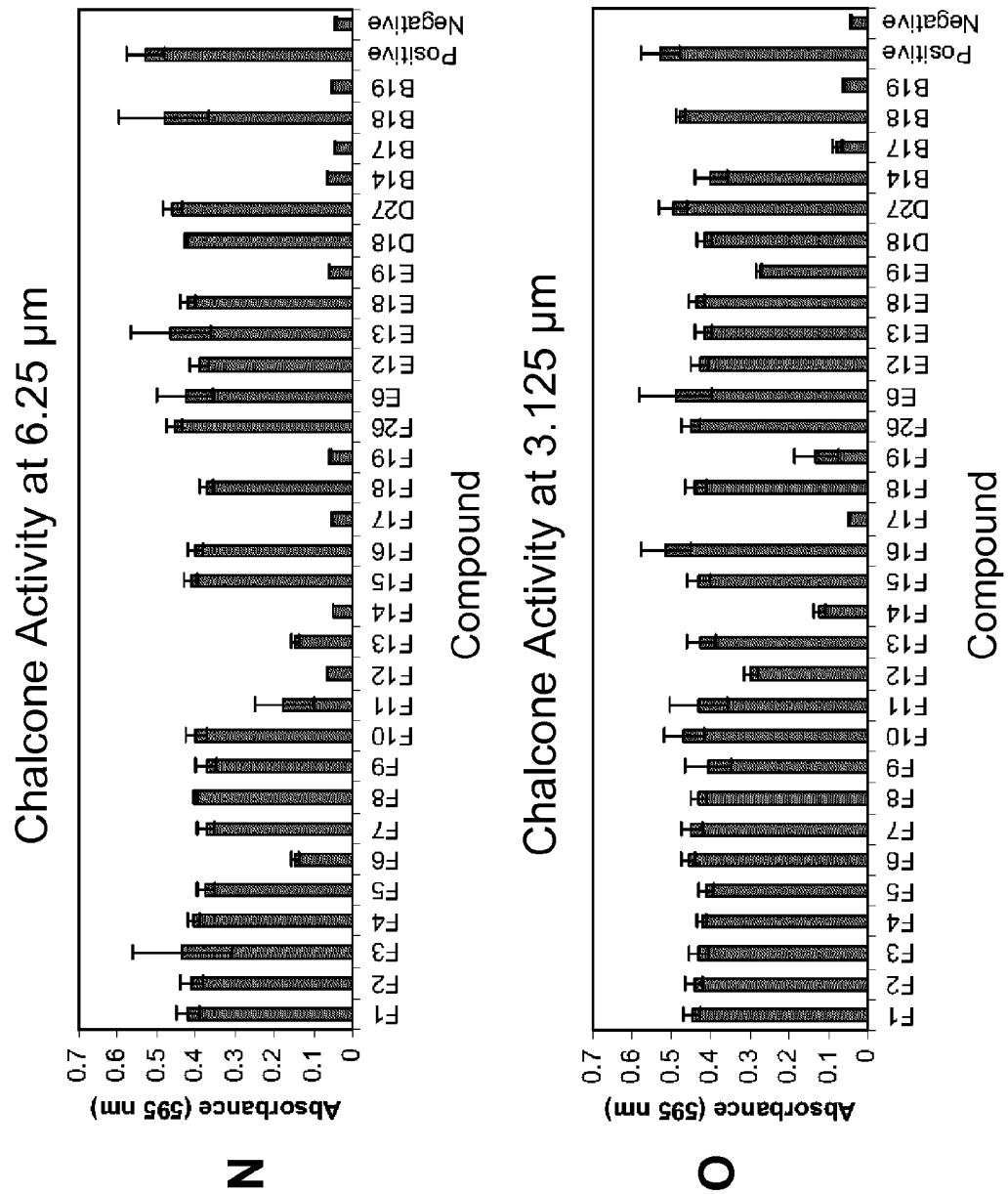
Figure 10:
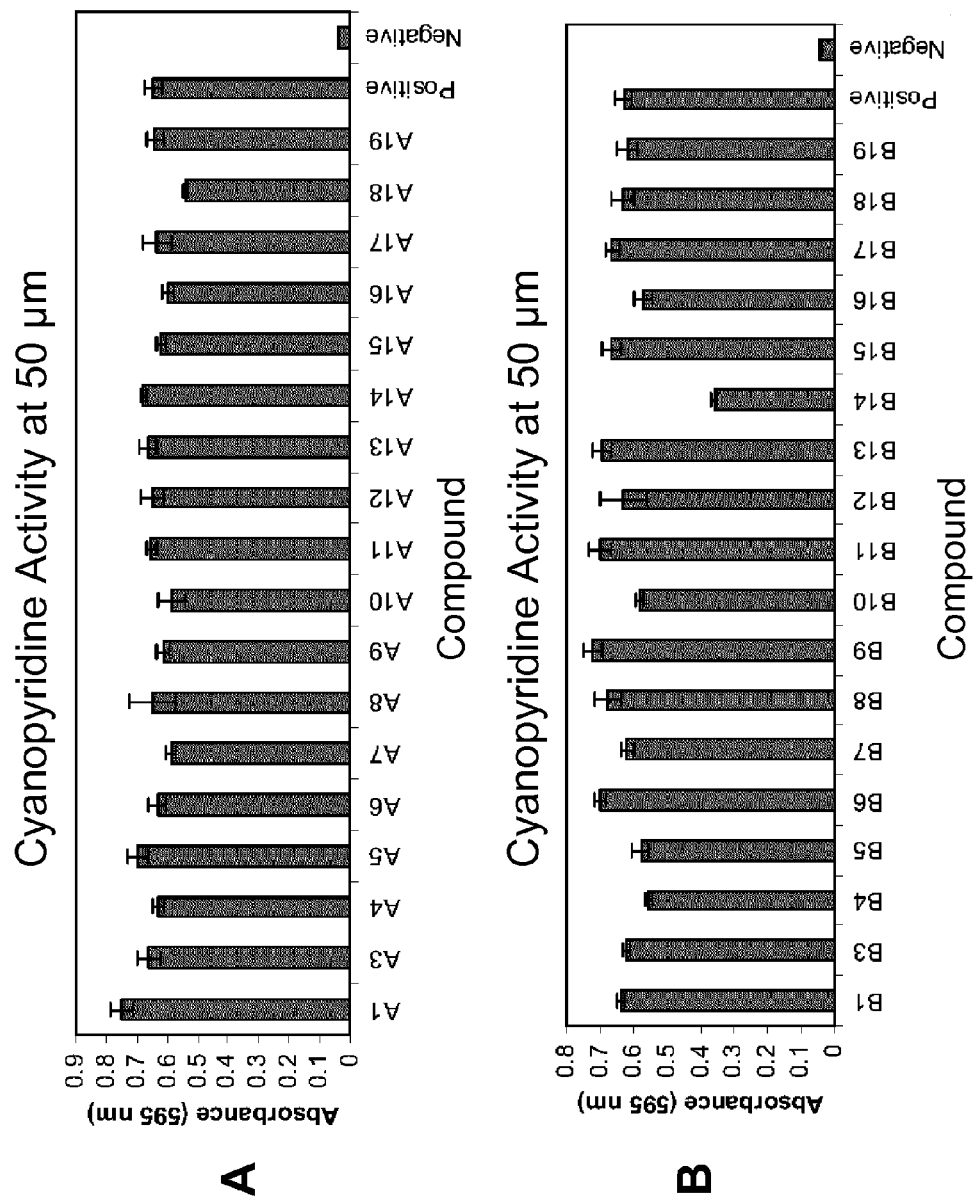
FIGS. 10A through 10F provide data showing the activity of cyanopyridine library members.
Figure 10:
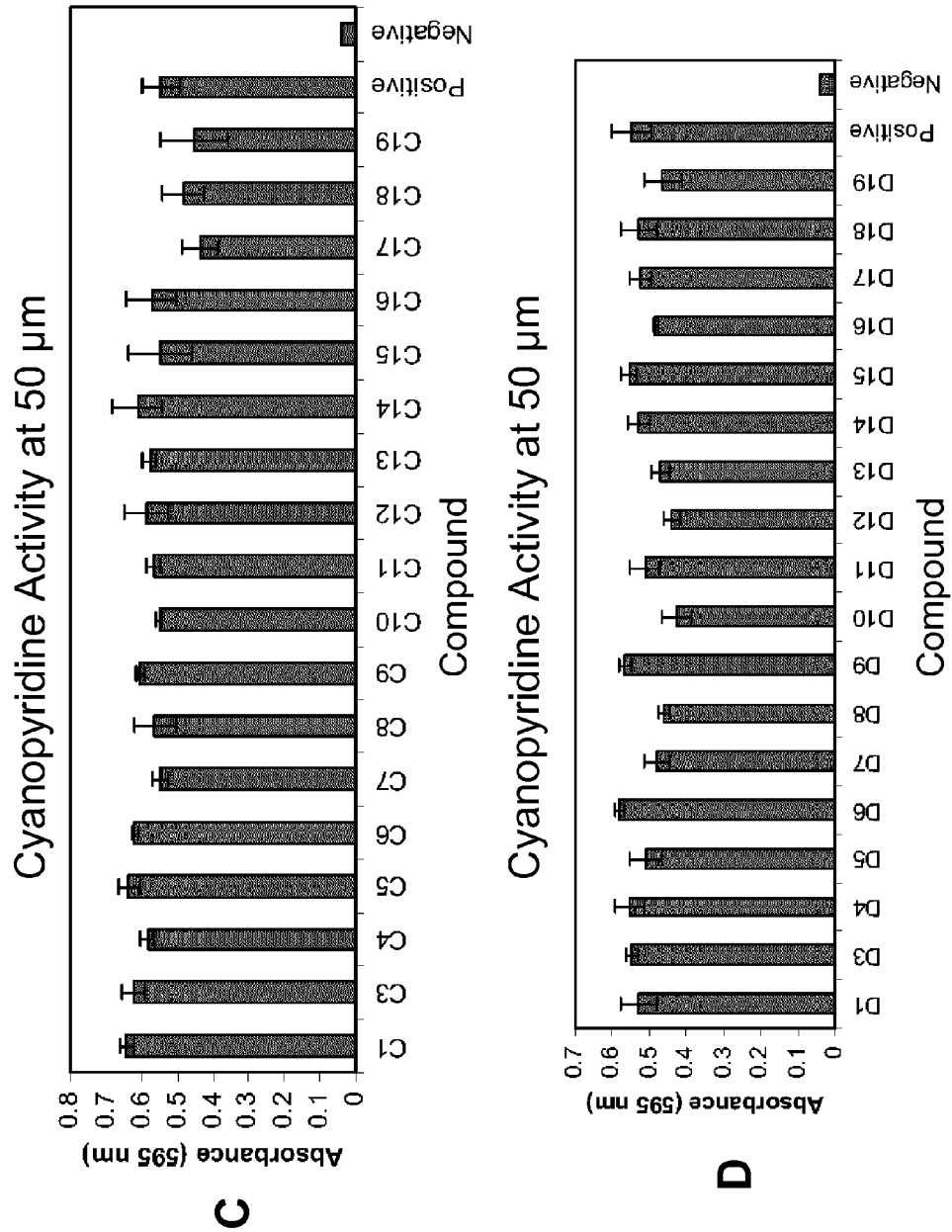
Figure 11:
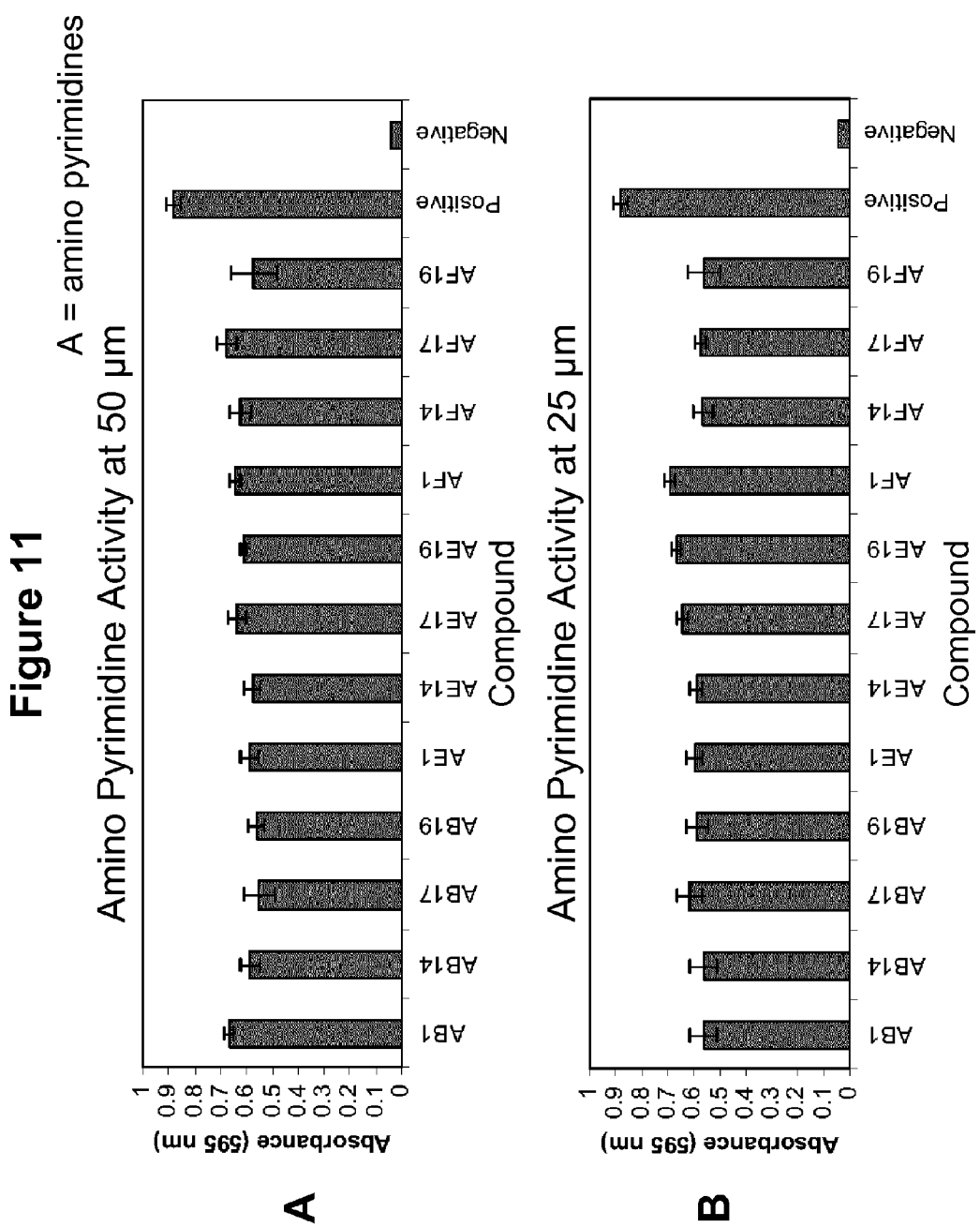
FIGS. 11A and 11B provide data showing the activity of certain amino-pyrimidine library members.
Figure 12:
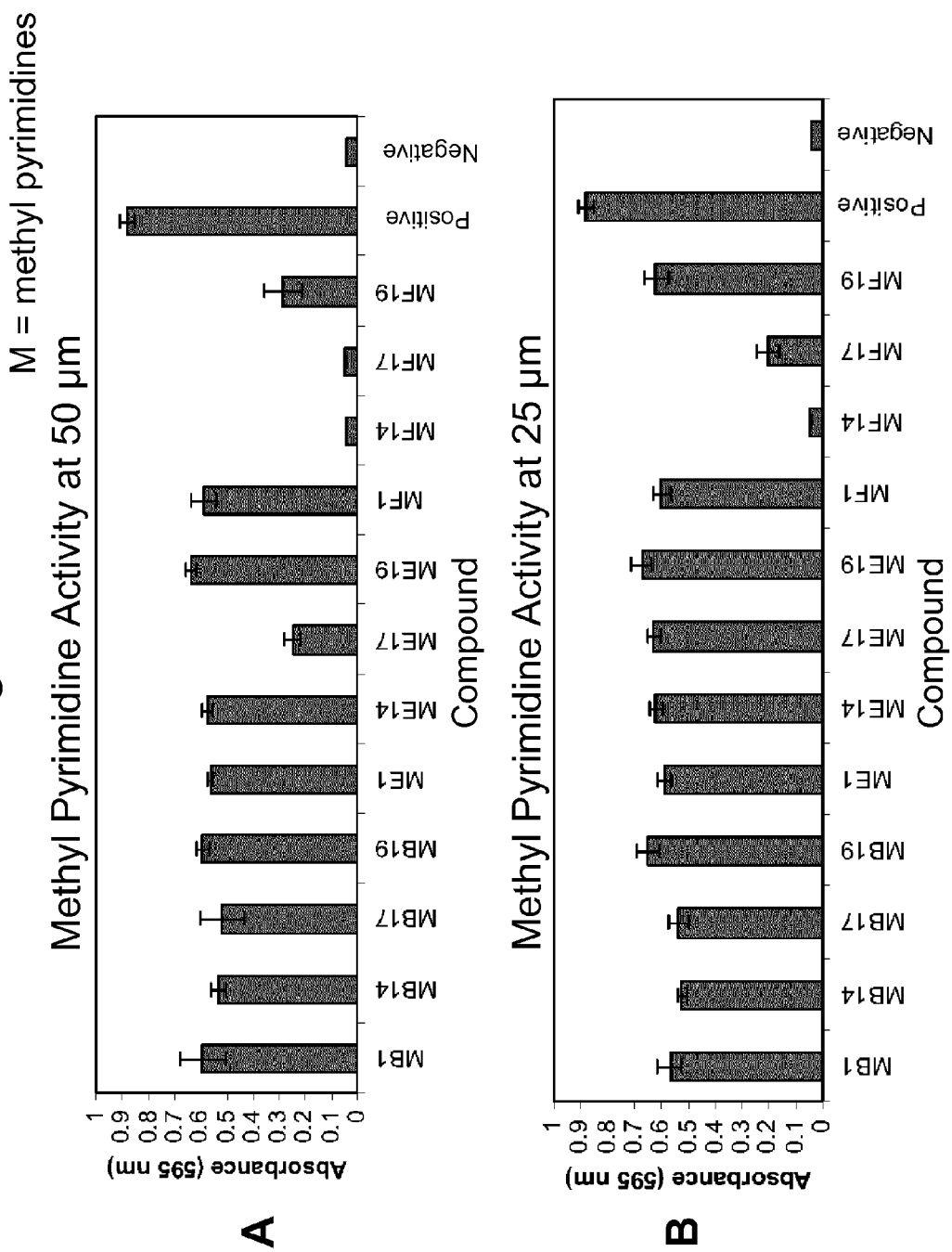
FIGS. 12A and 12B provide data showing the activity of certain methyl-pyrimidine library members.
Figure 13:
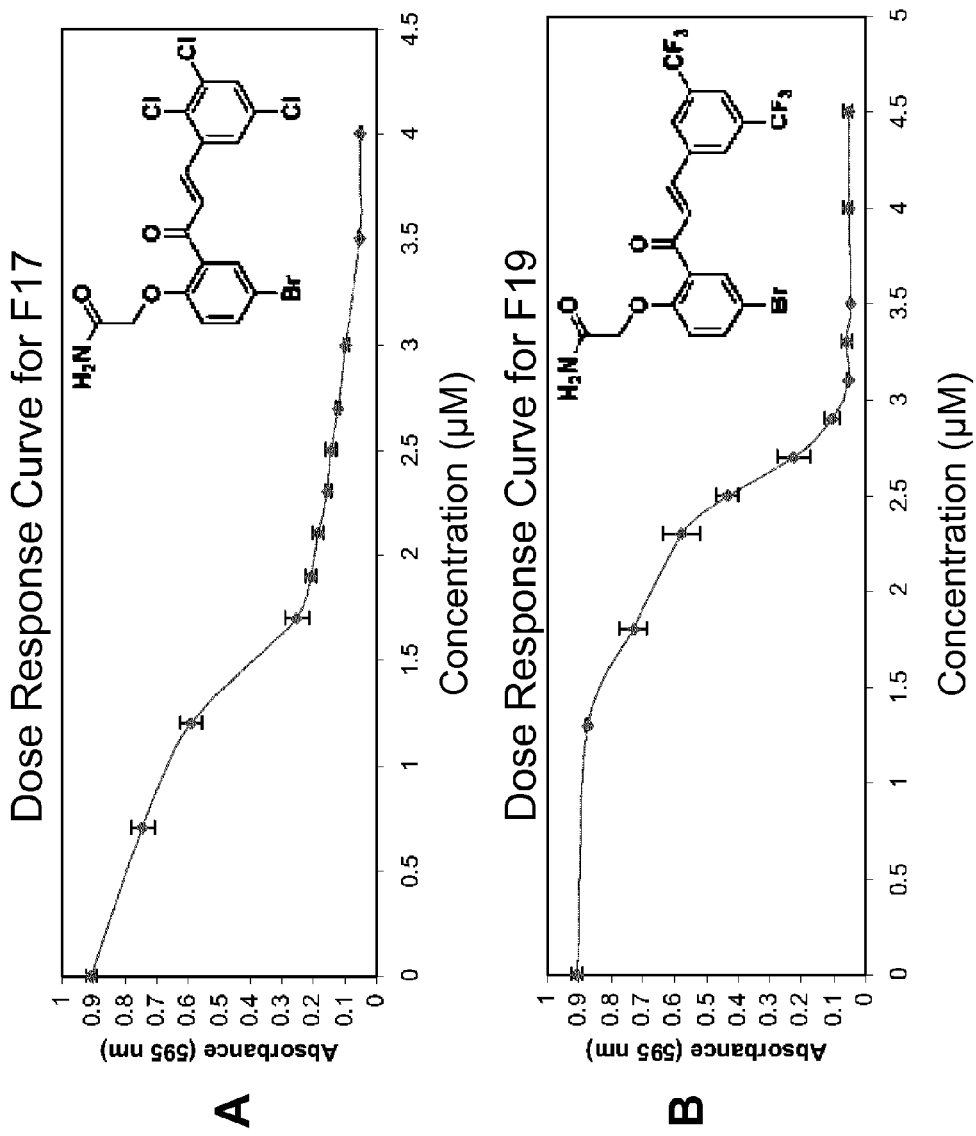
FIGS. 13A through 13E provide data showing dose responses for a number of library members.
Figure 13:
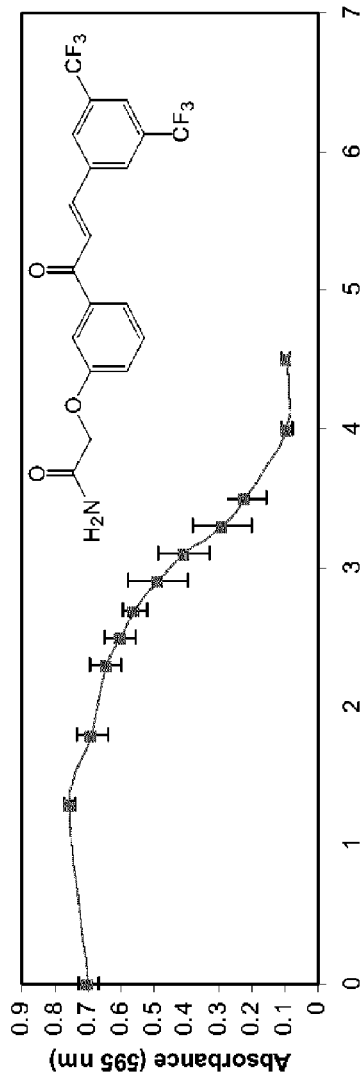
Figure 13:
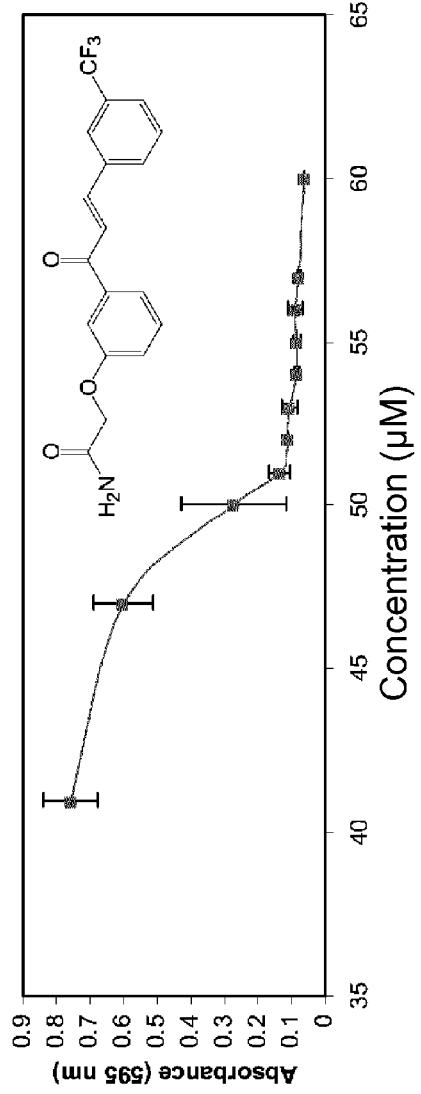
Figure 13:
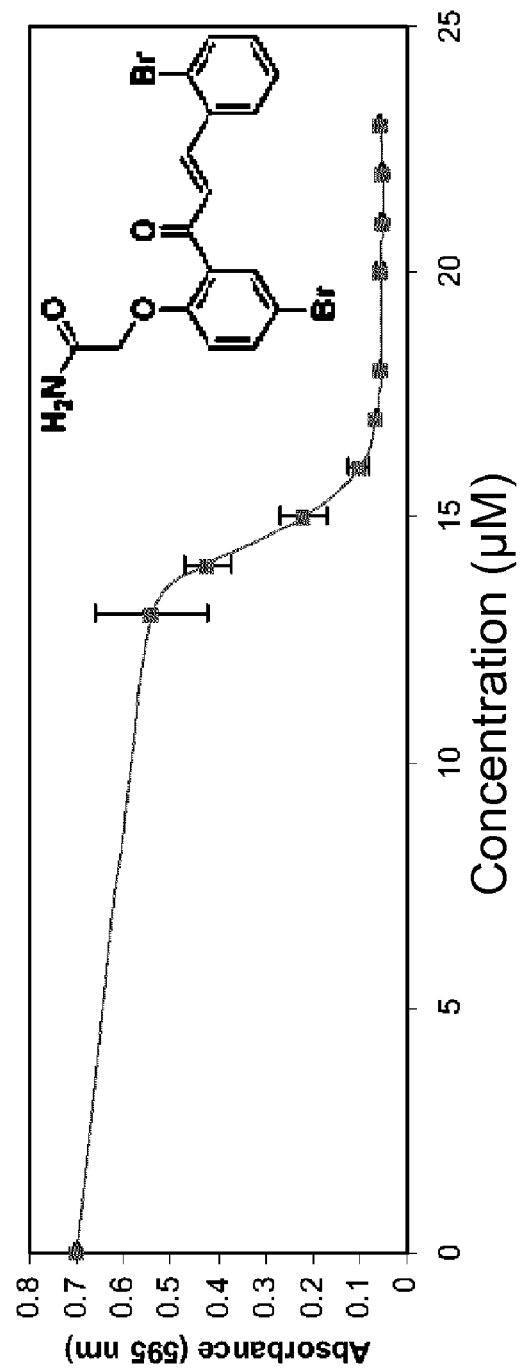

The third method evaluated was to determine antibacterial activity was an agar-overlay technique (as illustrated in FIG. 8), in which a macroarray was cleaved, overlaid with agar inoculated with *S. aureus*, and incubated for 18 h at 37° C. Macroarrays were cleaved for 1 h in a sealed desiccator saturated with TFA vapor. After the incubation period, triphenyl tetrazolium chloride (TTC) was added to the macroarray, allowing a clear determination of active antibacterial compounds. TTC is a redox indicator commonly used to show the presence or absence of live bacteria. Areas that appeared white indicated dead bacteria (i.e. antibacterial compound), whereas red areas indicated live bacteria (i.e. compound without antibacterial activity).

One drawback to the agar-overlay technique was that the entire compound was consumed during the assay. Therefore, it was impossible to determine the purities of the compounds that were being screened in the agar-overlay format, which could lead to mis-identification of inactive compounds that merely had low purities. To address this issue it was considered that creating "copies" of the macroarray would allow use of the agar-overlay assay and still have enough of the compound to either test against other bacterial strains or analyze purity by HPLC. A method was used in which the cleaved macroarray could be transferred to multiple cellulose sheets simultaneously. See WO 2008/016738 for more details of this method particularly as applied to macroarrays having Wang linkers. The copies are made by sandwiching a cleaved macroarray between solvent-soaked cellulose sheets and dry cellulose sheets. Pressure is applied, and the solvent is wicked upwards, transferring compound to the previously dry cellulose sheets in a spatially addressed manner. With each new macroarray copy, it is possible to simultaneously screen antibacterial activity of a compound against a number of important human pathogenic bacteria including, methicillin-resistant *S. aureus* (MRSA), *Staphylococcus epidermidis*, *Bacillus subtilis*, and *Klebsiella pneumoniae*.

Cleaved macroarrays are neutralized with ammonia vapor before being placed in a suitably sized agar dish. Freshly prepared agar inoculated with bacteria is poured over the entire macroarray, and the array was incubated for 18 h at 37° C. After 18 h, a solution of TTC is added and hits are identified as described above. Agar-overlay assays can also be used to screen antibacterial activity against *S. epidermidis*, *B. subtillis*, and *K. pneumoniae*. Estimated MICs were determined by cleaving the parent acetophenone building block from the macroarray and determining the approximate loading by HPLC analysis.

Prior to the agar-overlay assay, copies are made of the cleaved macroarray. In order to validate the agar-overlay screen, we use one copy for the agar-overlay method and another copy for a solution-phase MIC assay. In the solution phase assay, individual spots are punched out, placed in separate 4 mL glass vials, and eluted with acetonitrile. After solvent removal, loadings are estimated by analyzing an HPLC trace of the parent macroarray-cleaved acetophenone. Within a given series of acetophenones the corresponding Claisen-Schmidt condensation, as well as the other heterocycle generating reactions, proceeded with nearly 100% conversion. Therefore, we used the amount of cleaved acetophenone from one spot to estimate the amount of chalcone, pyrimidine, or cyanopyridine derivative on other spots. In general, compound amount (post-cleavage) ranged from 100-200 nmoles per spot, which was enough material to perform solution-phase antibacterial assays as well as HPLC or LC-MS analyses.

Macroarray compounds are dissolved in DMSO and pipetted into a 96-well multititer plate containing Luria-Bertani (LB) broth inoculated with MRSA. The final concentrations of the compounds selected, e.g., 50 μM, 25 μM, 12.5 μM, 6.3 μM, and 3.1 μM, with a final DMSO concentration of 2.5% for each compound in a given well. The plate is incubated with shaking at 37° C. for 18 h, and the absorbance is measured at 595 nm using a plate-reader. The approximate MIC can be determined by the complete absence of bacterial growth relative to our negative control (LB broth with no bacteria added). FIGS. 9A-9O, 10A-10F, 11A-11B and 12A-12B illustrate results of such assays with certain compounds of Formula I.

It was found that the agar-overlay assay provided a good primary screen for the macroarrays, as the compounds that showed activity in the agar-overlay assay (white spots) also showed good to strong antibacterial activity in the solution-phase assay. The screening methods can be used for a variety of microorganism, including bacteria and fungus. In particular, the screening methods can be employed to assess antibacterial activity against Gram-Negative and Gram-Positive bacteria.

FIGS. 13A-13E provide exemplary MIC data for several compounds of Formula I.

Figure 14:
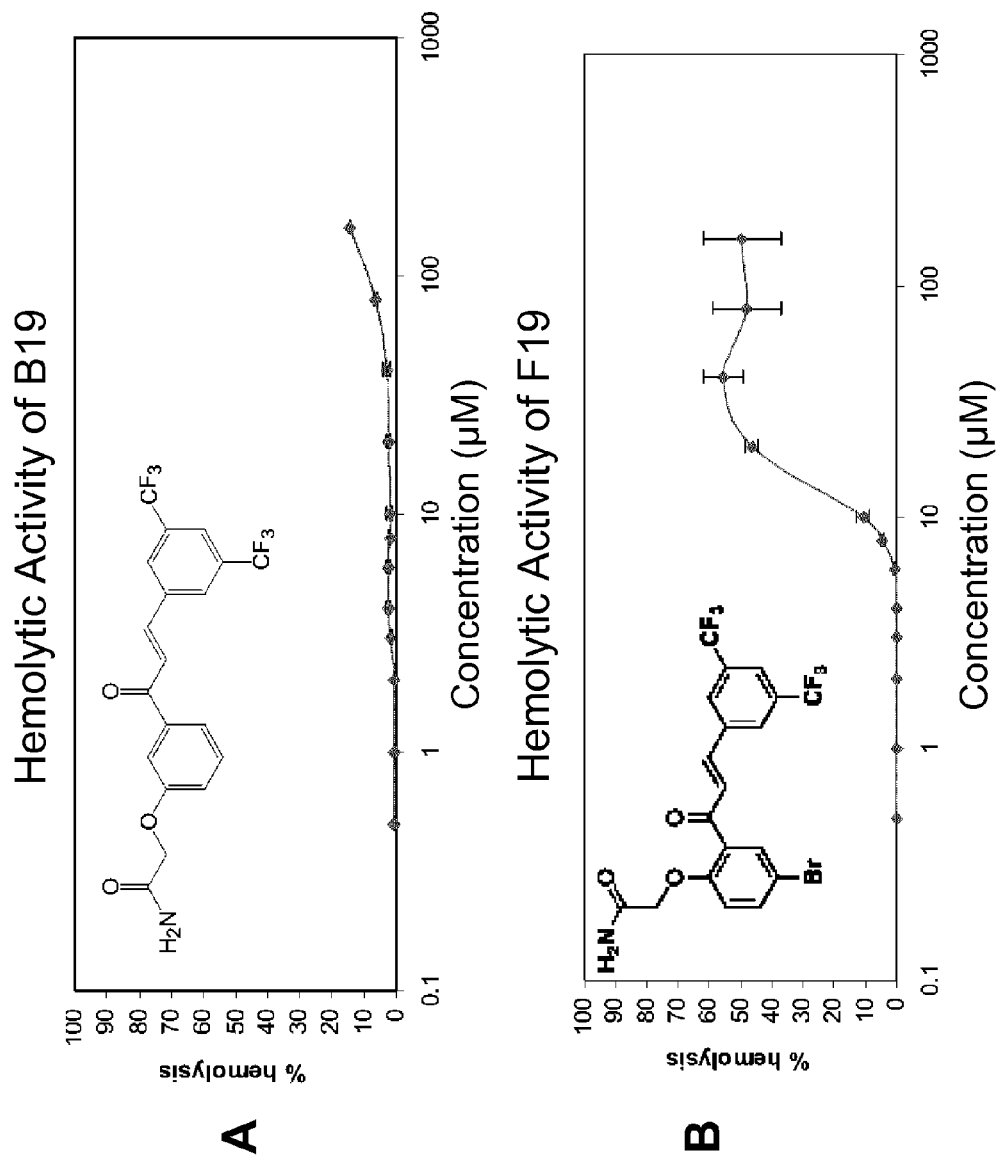
FIGS. 14A through 14C provide data showing hemolytic activity of a number of library members.
Figure 14:
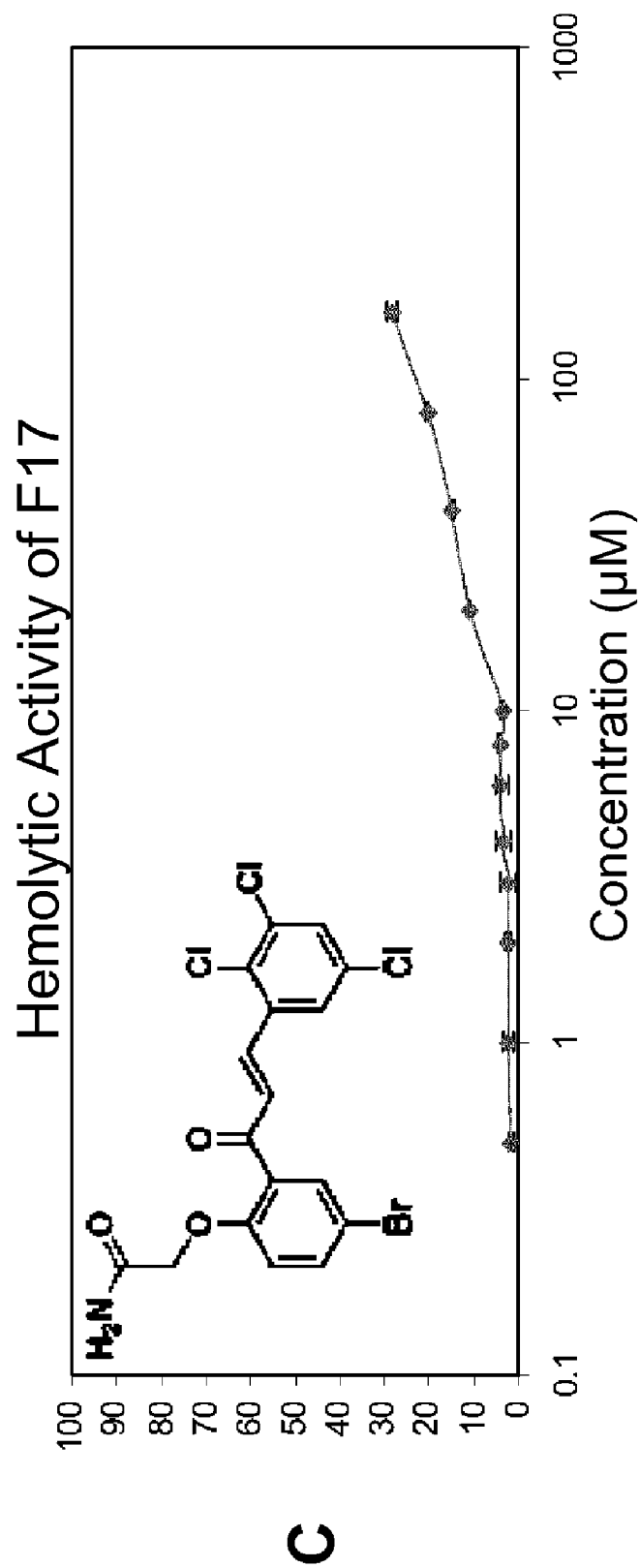

Compounds useful for therapeutic application preferably have low hemolytic activity. The hemolytic activity of several compounds of Formula I was assessed using standard methods as illustrated in FIGS. 14A-14C.

Figure 15:
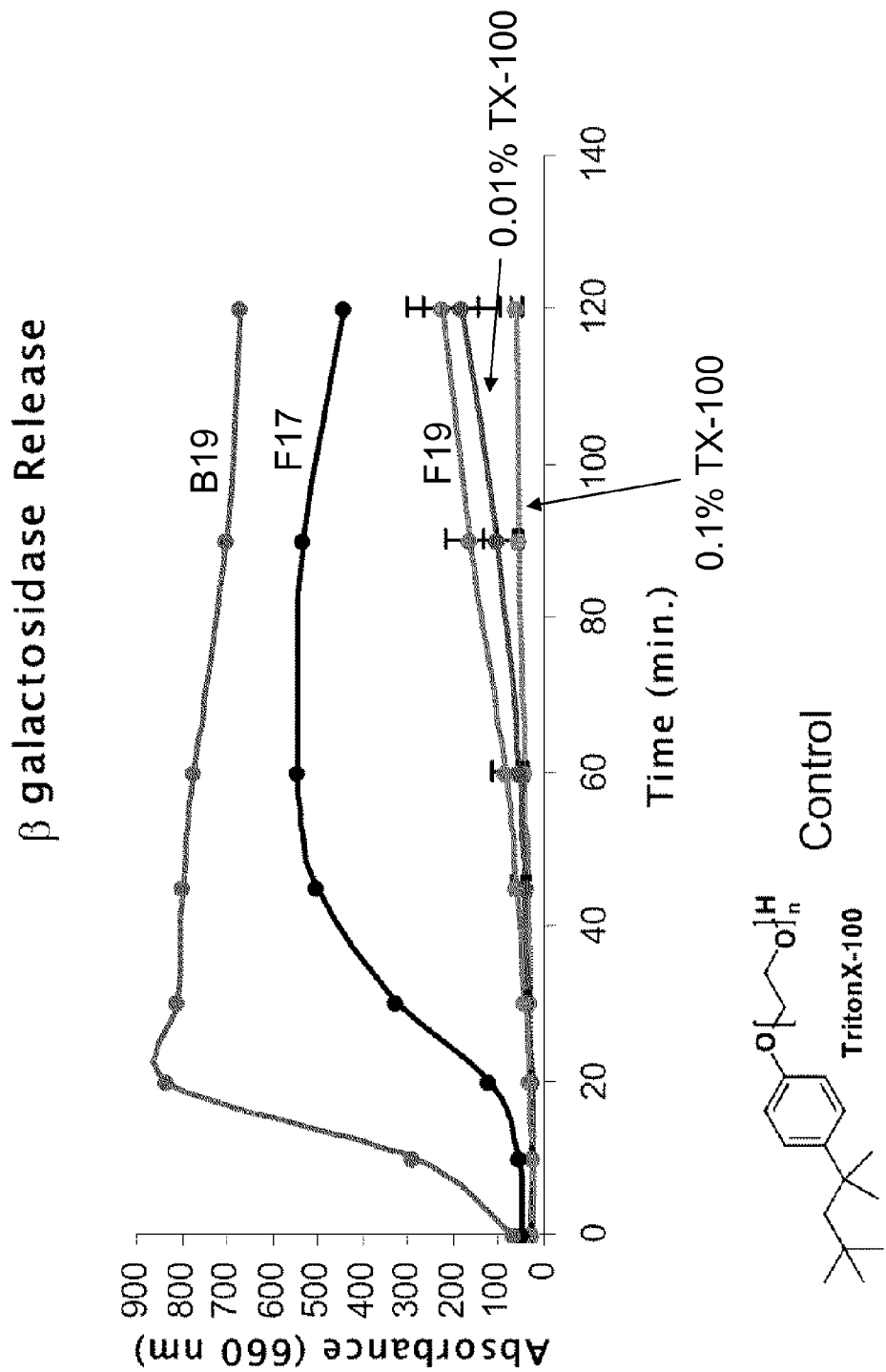
FIG. 15 provides data showing membrane permeability for a number of compounds.

Compounds useful for therapeutic application as antimicrobial activity preferably affect bacterial cell membrane permeability. FIG. 15 illustrates the affect of several compounds of Formula I on the permeability of bacterial cells.

| Compound | Support Purity (%)$^a$ | Support MIC (μM)$^b$ | Solution MIC (μM)$^c$ |
|---|---|---|---|
| F19 | 82 | <3.125 | 3.1 ± 0.2 |
| F17 | 87 | <3.125 | 3.5 ± 0.5 |
| B19 | 80 | <3.125 | 4.0 ± 0.5 |
| F5 | 97 | 12.5-25 | 17 ± 1.0 |
| B18 | 87 | 25-50 | 54 ± 1.0 |
| linezolid | — | — | 5.0 ± 1.0 |
| ciprofloxacin | — | — | 0.6 ± 0.2 |

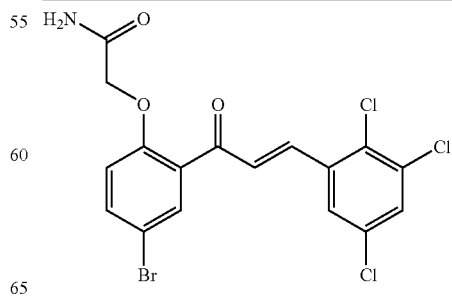

F17

-continued

| Compound | Support Purity (%)[a] | Support MIC (μM)[b] | Solution MIC (μM)[c] |
|---|---|---|---|

F19

F5

B19

B18

Table 1. Antibacterial activity of lead compounds from Rink support. (a) determined by HPLC trace at 254 nm. (b) solution-phase assay from cleaved macroarray. (c) authentic solution-phase sample.

Chalcones B19, F17, and F19 had antibacterial activity with MICs of 4.0±0.5 μM, 3.5±0.5 μM, and 3.1±0.2 μM, respectively (Table 1). (Note that compound names are based on the letter and number code of FIG. 4 which identifies the acetophenone and benzaldehyde used to form the base chalcone.) Several active chalcones, (B19, F17, F19, F5 and B18), were synthesized in solution to obtain more precise MIC values using our previously described solution phase assay. Notably, we identified chalcones that have antibacterial activities against MRSA in the low micromolar range and comparable to commercial therapeutics (ciprofloxican and linezolid).

In particular Compounds F19, F17 and B19 exhibited low solution MIC's (5 microliter or less) against MRSA and also exhibited low levels of hemolysis at 4× their MIC.

Materials and Methods
Bacteriological Assays

Bacteriological work was performed with strains obtained from ATCC. Luria-Bertani (LB) medium was used, as directed, for all bacterial work and was solidified with agar as needed. Overnight cultures were grown at 37° C. with shaking (*B. subtilis* was grown at 30° C.).

Disk Diffusion Assay

Compound spots were cleaved with TFA and neutralized with $NH_3$ as described herein. A 200-μL portion of diluted *S. aureus* 10390 ($10^6$ CFU/mL) was spread homogeneously across an agar plate. Compound spots were placed onto the agar, the plate was incubated at 37° C. for 18 h, and the diameters of the zones of inhibition were measured.

Agar Overlay TTC Assay

Macroarray copies were generated using the array transfer protocol described herein. Warm agar (15 mL) containing $10^6$ CFU/mL bacteria was poured into a Petri dish (9 cm diameter). The dish was swirled to eliminate air bubbles, and a macroarray copy (6×6 cm) was fully submerged in the agar. Following an 18 h incubation at 37° C., the plates were flooded with 0.1% (w/v) TTC in LB and allowed to develop for 1 h to visualize the zones of inhibition. Red zones indicated healthy bacteria, while white zones indicated that a compound on the macroarray inhibits growth of the bacterial strain.

MIC Determination

For estimated MIC determination, DMSO was added to the dried compound residue obtained from a single spot to afford ca. 100 μL of a 2 mM stock solution. Aliquots (5 μL) of these solutions were added to a 96-well plate, followed by 195 μL of diluted *S. aureus* 10390 ($10^6$ CFUs/mL) to yield ca. 50 μM final concentrations. The plates were swirled for 1 h to ensure compound dissolution, incubated for 12 h at 37° C., and the absorbance at 595 nm was recorded using a plate reader. Compounds that showed a selected level of growth inhibition at ca. 50 μM were subjected to further testing at C1-C3 concentrations (ca. 25 and 12.5 μM). Actual MIC values were determined for lead compounds resynthesized in solution using an analogous procedure with solutions of known concentration.

Analytical and Synthetic Instrumentation.

$^1$H NMR and $^{13}$C NMR spectra were recorded on a Bruker AC-300 spectrometer in deuterated solvents at 300 MHz and 75 MHz, respectively. Chemical shifts are reported in parts per million (ppm, δ) using tetramethyl silane (TMS) as a reference (0.0 ppm). Couplings are reported in hertz. LC-MS analyses were performed using a Shimadzu LCMS-2010a (Columbia, Md.) equipped with two pumps (LC-10ADvp), controller (SCL-10Avp), autoinjector (SIL-10Advp), UV diode array detector (SPD-M10Avp), and single quadrupole analyzer (by electrospray ionization, ESI). The LC-MS is interfaced with a PC running the Shimadzu LCSolutions software package (Version 2.04 Su2-H2). A Supelco (Bellefonte, Pa.) 15 cm×2.1 mm C-18 wide-pore reverse-phase column was used for all LC-MS work. Standard reverse-phase HPLC conditions for LC-MS analyses were as follows: flow rate=200 μL/min; mobile phase A=0.4% formic acid in $H_2O$; mobile phase B=0.2% formic acid in acetonitrile. HPLC analyses were performed using a Shimadzu HPLC equipped with a single pump (LC-10Atvp), solvent mixer (FCV-10Alvp), controller (SCL-10Avp), autoinjector (SIL-10AF), and UV diode array detector (SPD-M10Avp). A Shimadzu Premier 25 cm×4.6 mm C-18 reverse-phase column was used for all HPLC work. Standard reverse-phase HPLC conditions were as follows: flow rate=1.0 mL/min; mobile phase A=0.1% trifluoroacetic acid (TFA) in water; mobile phase B=0.1% TFA in acetonitrile. UV detection at 254 nm was used for all HPLC analyses. Compound purities were determined by integration of the peaks in HPLC traces measured at this wavelength.

Attenuated total reflectance (ATR)-IR spectra were recorded with a Bruker Tensor 27 spectrometer, outfitted with a single reflection MIRacle Horizontal ATR by Pike Technologies. A ZnSe crystal with spectral range 20,000 to 650 $cm^{-1}$ was used. UV spectra were recorded using a Cary 50 Scan UV-Vis spectrometer running Cary WinUV 3.00 software. Thin layer chromatography (TLC) was performed on silica gel 60 $F_{254}$ plates (E-5715-7, Merck). Sonication of reactions was performed in a laboratory ultrasound bath (Branson model #1510R-MT). All reported melting points are uncorrected.

Macroarray reactions subjected to oven heating were performed on a pre-heated bed of sand in a standard drying oven (VWR model #13OOU). Temperature measurements of planar surfaces were acquired using a non-contact IR thermometer (Craftsman model #82327) with an error of ±2.5%. An Eppendorf pipetteman with a calibrated range between 0.5 μL and 10.0 μL was used to "spot" or apply reagents onto planar membranes in a spatially addressed manner using disposable plastic tips. Washing steps were 5 min each. After each washing sequence, the macroarray was dried under a stream of $N_2$ for 20 min.

Solution-phase, microwave-assisted reactions were performed in a Milestone MicroSYNTH Labstation multimode microwave (MW) synthesis reactor.[i] This instrument is equipped with a continuous power source (1000 W max) and interfaced with an Ethos MicroSYNTH Lab Terminal PC running EasyWave reaction monitoring software. Using this reactor system, MW irradiation can be applied to reactions using either power (wattage) control or temperature control. Specialized, 70 mL Teflon/polyetheretherketone (PEEK) vessels, designed to withstand temperatures up to 200° C. and pressures up to 280 psi, were used for all MW-assisted reactions. The internal temperature of the reaction vessel was monitored using a fiber-optic temperature sensor enclosed in a protective ceramic sheath. At pressures above the 280-psi limit, the vessels are designed to release excess pressure by venting and then resealing themselves. No evidence of venting was observed during the course of the reactions described herein.

All chemical reagents were purchased from commercial sources (Alfa-Aesar, Aldrich, and Acros) and used without further purification. Solvents were purchased from commercial sources (Aldrich and J. T. Baker) and used as obtained, with the exception of dichloromethane ($CH_2Cl_2$), which was distilled over calcium hydride immediately prior to use. Planar cellulose membranes (Whatman 1Chr and 3MM chromatography paper, 20×20 cm squares) were purchased from Fisher Scientific and stored in a dessicator at room temperature until ready for use. All reaction on planar supports were performed under air.

TFA vapor compound cleavage procedure. Cleavage was performed either on compound spots (for the Kirby-Bauer disk diffusion assay and the solution-phase MIC assay) or the intact macroarray (for the TTC agar overlay assay). Compound spots were punched out of macroarrays using a standard desktop hole punch (spot diameter=6 mm) and placed in individual 4 mL vials. A 10 mL portion of TFA was added to the bottom of a glass vacuum dessicator (interior diameter 21 cm, interior height 20 cm). Up to 240 vials containing the spots (or one 12 cm×18 cm, intact macroarray) were placed on a perforated ceramic platform in the dessicator that was situated 7 cm above the TFA. The dessicator was evacuated to 60 mm Hg over a 10 min period. The dessicator was disconnected from the vacuum, sealed, and allowed to stand for an additional 50 min at room temperature. The vials (or intact macroarray) were removed from the dessicator and allowed to vent in a fume hood for 15 min. For routine LC-MS characterization or the solution-phase MIC assays, the compounds were eluted from the spots by adding acetonitrile (1.0 mL) to each vial. The vials were sealed and shaken for 15 min, after which the paper disks were removed, and the acetonitrile was evaporated under reduced pressure. For the Kirby-Bauer disk diffusion assay or the TTC agar overlay assay, the cleaved spots or macroarrays were subjected to an ammonia (NH3) neutralization step instead of elution (see biological assay section below). This cleavage method gave quantitative release of products (as determined by quantification of cleaved hydroxyacetophenone).

Full Bacteriological Assay Protocols
Kirby-Bauer Disk Diffusion Assay.

Preparation of Spots. Compound Spots were Subjected to the TFA cleavage conditions described above. The spots were next subjected to NH3 vapor to neutralize any remaining TFA. A 100 mL portion of concentrated NH4OH solution was poured into a 2.6 L Pyrex dish. Vials containing the spots (or intact macroarrays) were placed inside a small evaporating dish, and this was placed into the NH4OH solution. The Pyrex dish was covered, and NH3 vapor was allowed to slowly diffuse into the vials. After 1 h, the vials were removed from the NH3 chamber, and the spots were allowed to stand open in a fume hood for at least 15 min to vent prior to analysis in the following assays. This afforded dry, paper disks containing adsorbed compound. Vancomycin susceptibility test disks (30 μg per disk) and methicillin susceptibility disks (10 μg per disk) were used as controls as received.

Representative assay procedure. A 400 μL portion of S. aureus overnight culture was diluted with 100 mL of sterile LB broth to give ca. 1.0×106 colony forming units (CFUs) per mL. A 200 μL portion of this suspension was added to Petri dishes containing non-selective agar, and spread homogeneously across the agar with a sterile cotton swab.

Up to four compound disks (prepared as described above) were placed gently onto the bed of agar equidistant from each other. (Note: either face of the disk could be placed on top of the agar, as the compound was distributed uniformly throughout the disk.) The Petri dishes were incubated at 37° C. for 18 h. The plates were removed, and the diameters of the zones of inhibition were measured in mm using a ruler.

Macroarray Transfer Protocol.

A chalcone macroarray (12 cm×18 cm) was subjected to the TFA cleavage and $NH_3$ neutralization conditions described above, except that the spots were not punched out of the array. The intact, cleaved, and dried macroarray was cut into six square sections (12 spots each), and a concentrated fluorescent dye solutions in EtOAc was spotted (ca. 10 nL, using a glass capillary) in-between the compounds for later verification of macroarray transfer.

Untreated Whatman 3MM filter paper was cut into 6 cm×6 cm squares and arranged into a 2 cm high stack (30 squares). This stack was placed into a glass Petri dish (diameter=15 cm) containing 50 mL EtOH and allowed to soak up the solvent until saturated. A macroarray section was placed facedown on the stack, followed by four additional dry squares of Whatman 3MM. A flat aluminum block was placed on top of the stack and pressure (3 kg) was applied for 90 sec. The four sheets were then removed from the stack, separated with tweezers, allowed to dry, and visualized with a UV lamp (Centela Mineralight Lamp UVGL-58 at 366 nm) to confirm compound transfer. The fluorescent spots were marked with a

2 lead pencil and connected to form a grid. These macroarray copies were subjected to the TTC assay described in detail below. To prevent contamination in subsequent copies, the top two soaked sheets of the filter paper stack were removed after each transfer and replaced with fresh squares of EtOH-soaked filter paper.

This method gave a gradient of compound concentrations, with the last copy containing the most compound. The gradient was consistent across all locations on the array and for all compounds in the same structure class. Other solvents ($CH_2Cl_2$, MeOH) and longer transfer times were examined; the methods described here were found to be optimal.

Agar Overlay TTC Screening Protocol.

Test tubes were filled with 15 mL of 0.8% (w/v) agar in LB, autoclaved, and stored in a 55° C. water bath until needed. For bacterial overlay, an appropriate volume of overnight culture was added to each test tube. The tube was gently vortexed, and the contents (15 mL) were quickly poured into a sterile, polystyrene Petri dish (diameter=9 cm). The dish was swirled to eliminate lingering air bubbles, and a 12-spot macroarray copy (described above) was gently slid into the solution. The dish was swirled to completely immerse the membrane in agar, and the agar was allowed to cool. The dish was incubated for 18 h at 37° C. Following incubation, the plates were "flooded" by the addition of 8 mL of 0.1% (w/v) TTC solution in LB and allowed to develop for ca. 1 h to visualize the zones of inhibition. Red zones above the macroarray copy indicated healthy cells, while white zones indicated that a compound on the macroarray copy had growth inhibitory activity against the strain of interest.

Initially, we performed our overlays according to the procedures published by Silen et al (Silen, J. L.; Lu, A. T.; Solas, D. W.; Gore, M. A.; Maclean, D.; Shah, N. H.; Coffin, J. M.; Bhinderwala, N. S.; Wang, Y.; Tsutsui, K. T.; Look, G. C.; Campbell D. A.; Hale, R. L.; Navre, M.; DeLuca-Flaherty, C. R. *Antimicrob. Agents Chem.* 1998, 42, 1447-1453.) However, we found that all of the compounds "hit" using this method, and we were unable to determine our best hits. To better resolve the relative activities of our compounds, the agar volume was increased from eight to 15 mL.

Methicillin susceptibility test. We examined the susceptibility of our two *S. aureus* strains to methicillin using the agar overlay TTC assay. A susceptibility disk containing 10 μg of methicillin was placed in a Petri dish. Warm agar (0.8% in 15 mL LB) containing 106 CFU/mL of either *S. aureus* 10390 (SA) or methicillin-resistant *S. aureus* 33591 (MRSA) was poured over the disk. The dishes were incubated at 37° C. for 18 h and visualized with TTC.

Macroarray Overlay Data.

Estimated MIC Determination Protocol for Macroarray Compounds.

Preparation of spot samples and controls. An aliquot of DMSO (ca. 100 μL depending on the loading of the parent hydroxyacetophenone) was added to the dried compound residue obtained after TFA cleavage and elution from a single spot. This afforded a 2.0 mM "spot stock" solution for each spot. A small aliquot of each "spot stock" solution was saved for subsequent LC-MS analysis.

For the linezolid standard, 1.0 mL of acetonitrile was added to a single linezolid susceptibility test disk (30 μg per disk) in a 4 mL vial and vortexed for 15 min. The disk was removed, and the solution was concentrated under reduced pressure. The resulting residue was dissolved in 44 μL of DMSO to afford a 2.0 mM "spot stock" solution of linezolid.

Control "support" spots were punched from planar supports that had undergone all macroarray synthesis steps except for the loading of the initial hydroxyacetophenone building blocks. These samples allowed us to study the effects of the support background composition on bacterial growth. In addition, hydroxyacetophenone derived spots that had undergone all macroarray synthesis steps except for the Claisen-Schmidt condensation were used as "parent" controls. These samples allowed us to determine the effects of minor impurities resulting from unreacted acetophenone reacting in subsequent steps. "Spot stock" solutions were generated from each of these spots as described above. In all cases studied, neither the support nor the parent control spots affected *S. aureus* growth.

For estimated MIC screens, 5.0 μL portions of the "spot stock" solutions were added to the appropriate wells in a sterile, polystyrene 96-well plate to yield ca. 50 μM solutions (dependent on the initial loading of hydroxyacetopheneone and compound purity). To the positive and negative control wells, 5.0 μL of DMSO were added (positive controls contained bacteria but no compound, while negative controls had neither compound, nor bacteria). All estimated MIC assays were performed in quadruplicate. Note: the MIC value is defined as the lowest concentration where no bacterial growth occurs.

Representative estimated MIC assay procedure. This assay procedure is based in part on the method reported by Strøm et al. (Strøm, M. B.; Haug, E. B.; Skar, M. L.; Stensen, W.; Stiberg, T.; Svendsen, J. S. *J. Med. Chem.* 2003, 46, 1567-1570.) A 400 μL portion of overnight *S. aureus* 10390 culture was diluted with 100 mL of sterile LB broth to give ca. $10^6$ CFUs per mL. Aliquots (195 μL) of this solution were added to all of the wells in a sterile 96-well plate (except for the negative control wells; 195 μL of sterile LB broth were added to these wells). The plates were placed on an orbital shaker table and gently swirled for 1 h to ensure compound dissolution, and then incubated (without shaking) for 12 h at 37° C. The absorbance at 595 nm was recorded using a plate reader. Compounds that demonstrated complete growth inhibition had an absorbance equal to that of the negative control. Compounds exhibiting no growth inhibition had an absorbance equal to that of the positive control.

Compounds that showed a selected complete growth inhibition at ca. 50 μM were subjected to further testing. The original "spot stock" solutions of these compounds were diluted with DMSO to give ca. 25 and 13 μM final concentrations and tested for inhibitory activities using the procedure described above.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomer and enantiomer of the compound described individually or in any combination. When an atom is described herein, including in a composition, any isotope of such atom is intended to be included. Specific names of compounds are intended to be exemplary, as it is known that one of ordinary skill in the art can name the same compounds differently. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Methods of this invention comprise the step of administering a "therapeutically effective amount" of the present therapeutic formulations containing the present compounds, to treat, reduce or regulate a disease state in a patient, including a disease state involving one or more infectious agents such as bacteria. The term "therapeutically effective amount," as used herein, refers to the amount of the therapeutic formulation, that, when administered to the individual is effective to treat, reduce or regulate a disease state in a patient, including a disease state involving one or more infectious agents such as bacteria. As is understood in the art, the therapeutically effective amount of a given compound or formulation will depend at least in part upon, the mode of administration (e.g. intravenous, oral, topical administration), any carrier or vehicle employed, and the specific individual to whom the formulation is to be administered (age, weight, condition, sex, etc.). The dosage requirements need to achieve the "therapeutically effective amount" vary with the particular formulations employed, the route of administration, and clinical objectives. Based on the results obtained in standard pharmacological test procedures, projected daily dosages of active compound can be determined as is understood in the art.

Any suitable form of administration can be employed in connection with the therapeutic formulations of the present invention. The therapeutic formulations of this invention can be administered intravenously, in oral dosage forms, intraperitoneally, subcutaneously, or intramuscularly, all using dosage forms well known to those of ordinary skill in the pharmaceutical arts.

The therapeutic formulations of this invention can be administered alone, but may be administered with a pharmaceutical carrier selected upon the basis of the chosen route of administration and standard pharmaceutical practice.

The therapeutic formulations of this invention and medicaments of this invention may further comprise one or more pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety.

We claim:

1. A compound having antimicrobial activity which has the formula:

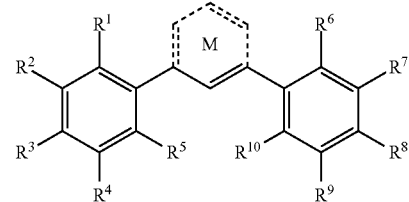

and salts, and esters thereof,
where:
M is

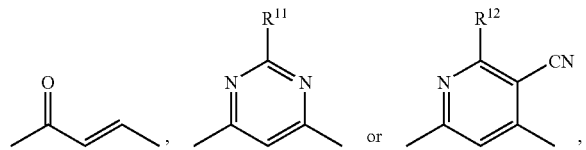

where $R^{11}$ is a C1-C6 alkyl group, or a —NRR'group and $R^{12}$ is a C1-C6 alkyl group, where R and R' are independently selected from hydrogen, or a C1-C6 alkyl group;
at least one of $R^1$ or $R^2$ is selected from:
—O—$(CH_2)_n$—CO—$NH_2$, where n is an integer ranging from 1-6, or
at least one of $R^1$-$R^5$ is selected from:

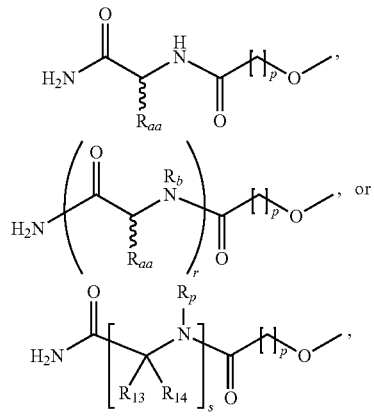

where p are integers ranging from 1 to 6, r and s are integers ranging from 1 to 100;
$R_{aa}$ is selected from hydrogen, a C1-8 alkyl group, a C2-C8 alkenyl group, a C2-C8 alkynyl group, a C6-C13 aryl group, a C6-C13 aralkyl group, a C2-C8 ether group, a C2-C8 thither group, a C3-C8 cycloalkyl group, a C3-C8 cycloalkenyl group, a C3-C10 heterocyclic group having 1-3 heteroatoms, or a C3-C13 heteroaromatic group having 1-3 heteroatoms, each of which groups are optionally substituted with one or more halogens, —$OR$, —$SR_a$, C3-C3-alkyl, —COOH, —COO$^-$, —$NR_aR'_a$, —$NR_aR'_aR''_a$, —$CONR_aR'_a$, —$NR_a$—$C(NR_aR'_a)$=$NR_a$, or —$NR_a$—$C(NR_aR'_a)$=$NR_aR'^+_a$ groups, where $R_a$, $R'_a$ and $R''_a$ are independently hydrogen or C1-C3 alkyl groups, $R_b$ is hydrogen, or a C1-C3 alkyl; or $R_b$ and $R_{aa}$ together with the atoms to which they are attached form an optionally substituted C5-C8 heterocyclic ring having 1 or 2 heteroatoms;

$R_p$ is selected from hydrogen, a C1-8 alkyl group, a C2-C8 alkenyl group, a C2-C8 alkynyl group, a C6-C13 aryl group, a C2-C8 ether group, a C2-C8 thioether group, a C3-C8 cycloalkyl group optionally having 1 or 2 heteroatoms, a C3-C8 cycloalkenyl group optionally having 1 or 2 heteroatoms, a C3-C13 heteroaromatic group having 1-3 heteroatoms, all of which are optionally substituted with one or more of —$OR_c$, —$SR_c$, C1-C3-alkyl, —COOH, —COO$^-$, —$NR_cR'_c$, —$NR_cNR'_cR''_c$, —$CONR_cR'_c$, —$N_{Rc}$—$C(NR_cR'_c)$=$NR_c$, and —$NR_c$—$C(NR_cR'_c)$=$NR_cR'^+_c$, where $R_c$, $R'_c$ and $R''_c$ are independently hydrogen or a C1-C3 alkyl group;

each $R_{13}$ and $R_{14}$ is independently selected from hydrogen; a C1-C6 alkyl group optionally substituted with one or more halogens; or a benzyl group or a phenyl group optionally substituted with one or more halogens, hydroxyl groups or C1-C3 alkyl groups or one of $R_{13}$ or $R_{14}$ together with $R_p$ and the atoms to which they are attached form an optionally substituted C4-C8 heterocyclic group which contains 1 or 2 heteroatoms and which optionally contains 1 or 2 double bonds;

the remaining $R^1$-$R^5$ are selected from hydrogen, halogen, a hydroxyl group, a —$NR_dR'_d$ group, a —CN group, an azide group, a —$NO_2$ group, an optionally substituted C1-C12 alkyl group, an optionally substituted C2-C12 alkenyl group, an optionally substituted C2-C12 alkynyl group, an optionally substituted C6-C13 aryl group, an optionally substituted C1-C12 alkoxy group, an optionally substituted C6-C13 aryloxy group, or an optionally substituted C3-C8 heterocycloalkyl group, and $R^6$-$R^{10}$ are independently selected from hydrogen, halogen, a hydroxyl group, a —$NR_dR'_d$ group, a —CN group, an azide group, a —$NO_2$ group, an optionally substituted C1-C12 alkyl group, an optionally substituted C2-C12 alkenyl group, an optionally substituted C2-C12 alkynyl group, an optionally substituted C6-C13 aryl group, an optionally substituted C1-C12 alkoxy group, an optionally substituted C6-C13 aryloxy group, or a —O—$(CH_2)_m$—CO—$NH_2$ group, where m is 1-6, where $R_d$ and $R'_d$ are selected from hydrogen, C1-C6 alkyl, C3-C8 cycloalkyl, C4-C8 heterocycloakyl and C6-C13 aryl, and where optional substitution of $R^1$-$R^{10}$ groups is substitution with one or more halogen, —$OR_e$, —$SR_e$, —COOH, —COO$^-$, —$NR_eR'_e$, —$NR_eR'_eR''_e$, —$CONR_eR'_e$, —$NR_e$—$C(NR_eR'_e)$=$NR_e$, —$NR_e$—$C(NR_eR'_e)$=$NR_eR'^+_e$, or C1-C3-alkyl group optionally substituted with one or more halogens, —OH, —SH, —COOH, —COO$^-$, C1-C3 alkoxy groups, —$NR_eR'_e$, or —$CONR_eR'_e$, where $R_e$, $R'_e$, and $R''_e$ are selected from hydrogen, a C1-C3 alkyl group, or a C6-C13 aryl group each of which is optionally substituted with one or more halogens, —OH, —SH, —COOH, —COO$^-$, or C1-C3 alkoxy; provided that not every $R^6$-$R^{10}$ is hydrogen.

2. A compound of claim 1, wherein $R^1$ or $R^2$ is a —O—$(CH_2)_n$—CO—$NH_2$ group, where n is 1-6 and the remaining $R^1$-$R^5$ are independently selected from hydrogen, halogen, a hydroxyl group, a —$NR_dR'_d$ group, a —CN group, an azide group, a —$NO_2$ group, an optionally substituted C1-C12 alkyl group, an optionally substituted C2-C12 alkenyl group, an optionally substituted C2-C12 alkynyl group, an optionally substituted C6-C13 aryl group, an optionally substituted C1-C12 alkoxy group, an optionally substituted C6-C13 aryloxy group, or an optionally substituted C3-C8 heterocycloalkyl group.

3. A compound of claim 2 where $R^{11}$ is a methyl group or a —$NH_2$ group and $R^{12}$ is a methyl group.

4. A compound of claim 2, wherein $R^1$ is a —O—$(CH_2)_n$—CO—$NH_2$ group, where n is 1-6.

5. A compound of claim 1 having formula:

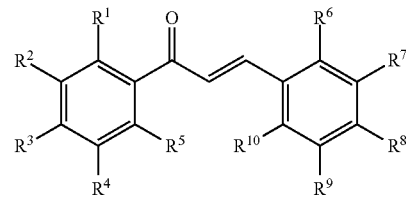

and salts, and esters thereof.

6. A compound of claim 5, wherein $R^1$ or $R^2$ is a —O—$(CH_2)_n$—CO—$NH_2$ group, where n is 1-6 and the remaining $R^1$-$R^5$ are independently selected from hydrogen, halogen, a hydroxyl group, a —$NR_dR'_d$ group, a —CN group, an azide group, a —$NO_2$ group, an optionally substituted C1-C12 alkyl group, an optionally substituted C2-C12 alkenyl group, an optionally substituted C2-C12 alkynyl group, an optionally substituted C6-C13 aryl group, an optionally substituted C1-C12 alkoxy group, an optionally substituted C6-C13 aryloxy group, or an optionally substituted C3-C8 heterocycloalkyl group.

7. A compound of claim 6 wherein $R^2$ is a —O—$(CH_2)_n$—CO—$NH_2$ group, where n is 1-6 and $R^1$, and $R^3$-$R^5$ are hydrogens.

8. A compound of claim 7 wherein $R^6$-$R^{10}$ are selected from hydrogen, a chlorine, a bromine, or a trifluoromethyl group.

9. A compound of claim 6, wherein $R^1$ is a —O—$(CH_2)_n$—CO—$NH_2$ group, where n is 1-6, $R^4$ is hydrogen, a chlorine or a bromine, and $R^2$, $R^3$ and $R^5$ are hydrogens.

10. A compound of claim 9 wherein $R^6$-$R^{10}$ are selected from hydrogen, halogen, a C1-C3 alkyl group, a C1-C3 haloalkyl group, a C1-C3 alkoxy group, a phenyl group, or a phenoxy group.

11. A compound of claim 9 wherein $R^6$-$R^{10}$ are selected from hydrogen, a chlorine, a bromine, or a trifluoromethyl group.

12. A compound of claim 6 wherein $R^1$ or $R^2$ is a —O—$(CH_2)_n$—CO—$NH_2$ group, where n is 1-6, $R^4$ is a halogen and at least one of $R^6$-$R^{10}$ is a halogen or a halogenated alkyl group.

13. A compound of claim 6 wherein $R^1$ is a —O—$(CH_2)_n$—CO—$NH_2$ group, where n is 1-6, and at least one of $R^6$-$R^{10}$ is a halogen or a halogenated alkyl group.

14. A compound of claim 13 wherein at least $R^7$ and $R^9$ are halogens or halogenated alkyl groups.

15. A compound of claim 14 wherein $R^4$ is hydrogen, a halogen, a —CN group, an azide group, a —NO$_2$ group, a C1-C3 alkyl group or a halogenated C1-C3 alkyl group.

16. A compound of claim 15 wherein $R^4$ is hydrogen, a bromine or a chlorine.

17. A compound of claim 14 wherein both of $R^7$ and $R^9$ are halogens or halogenated alkyl groups and $R^6$, $R^8$ and $R^{10}$ are selected from hydrogen or C1-C3 alkyl groups.

18. A compound of claim 17 wherein $R^4$ is hydrogen, a halogen, a —CN group, an azide group, a —NO$_2$ group, or a halogenated C1-C3 alkyl group.

19. A compound of claim 18 wherein $R^4$ is hydrogen, a bromine or a chlorine.

20. The compound of claim 1 selected from:

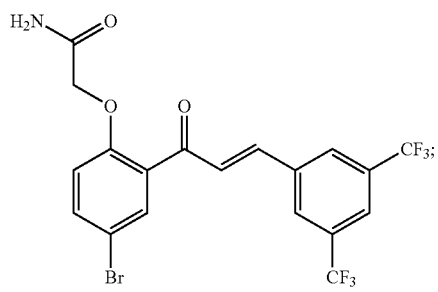

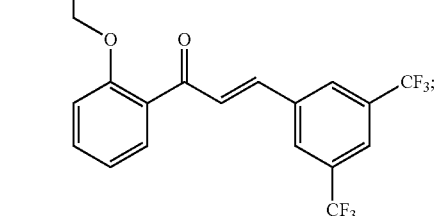

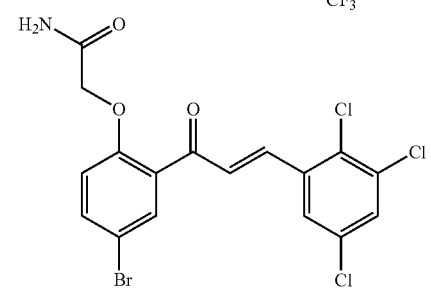

or salts or esters thereof.

21. A compound of claim 1 having formula:

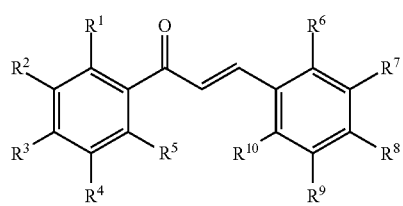

and salts, and esters thereof wherein $R^1$ is selected from:
a —O—(CH$_2$)$_n$—CO—NH$_2$ group, where n is 1-6;

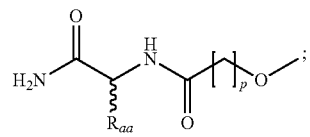

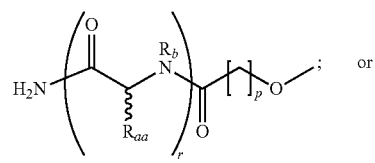

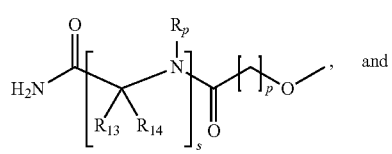

$R^7$ and $R^9$ are halogens or halogenated alkyl groups.

22. A compound of claim 21 wherein $R^4$ is hydrogen, a halogen, a —CN group, an azide group, a —NO$_2$ group, a C1-C3 alkyl group or a halogenated C1-C3 alkyl group.

23. A compound of claim 21 wherein $R^4$ is hydrogen, a bromine or a chlorine.

24. A compound of claim 21 wherein $R^6$, $R^8$ and $R^{10}$ are selected from hydrogen or C1-C3 alkyl groups.

25. A compound of claim 21 wherein $R^4$ is a hydrogen or a halogen; $R^2$, $R^3$, and $R^5$ are hydrogens; $R^7$ and $R^9$ are independently halogens or halogenated alkyl groups, $R^6$ is a halogen or hydrogen, and $R_8$ and $R^{10}$ are hydrogens.

26. A compound of claim 21 wherein $R^4$ is a hydrogen, chlorine or bromine; $R^2$, $R^3$, and $R^5$ are hydrogens; $R^7$ and $R^9$ are independently chlorine bromine or trifluoromethyl groups, $R^6$ is a chlorine, bromine or hydrogen, and $R_8$ and $R^{10}$ are hydrogens.

27. A compound of the formula selected from:

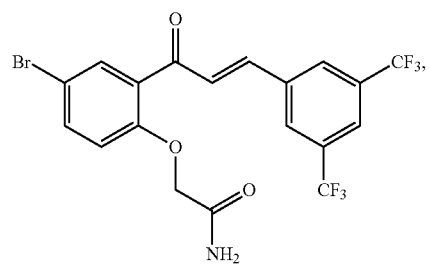

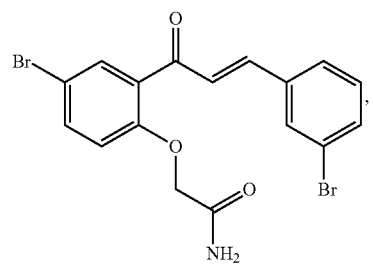

-continued

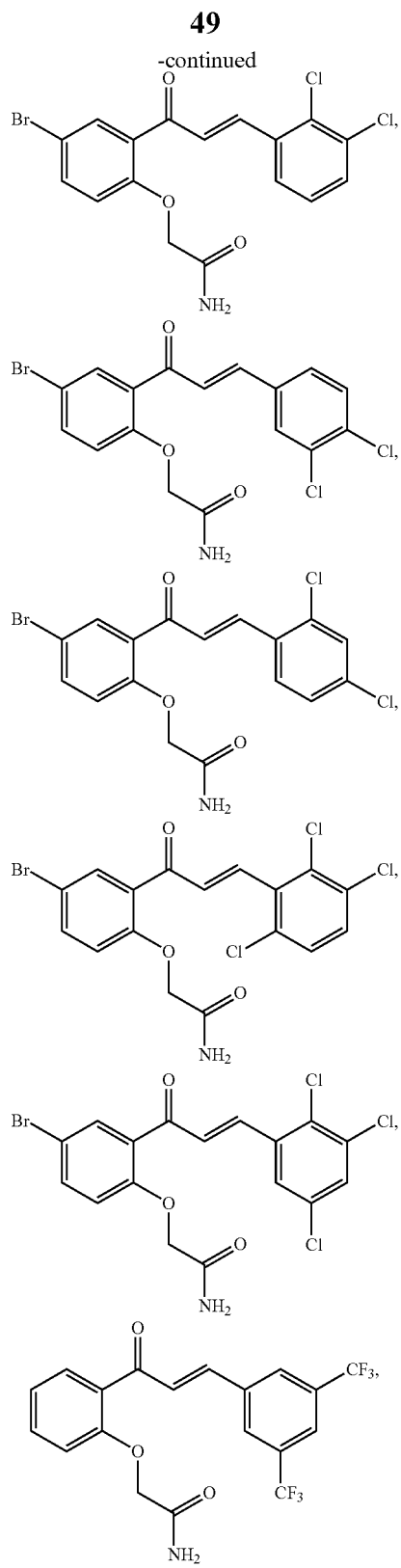

-continued

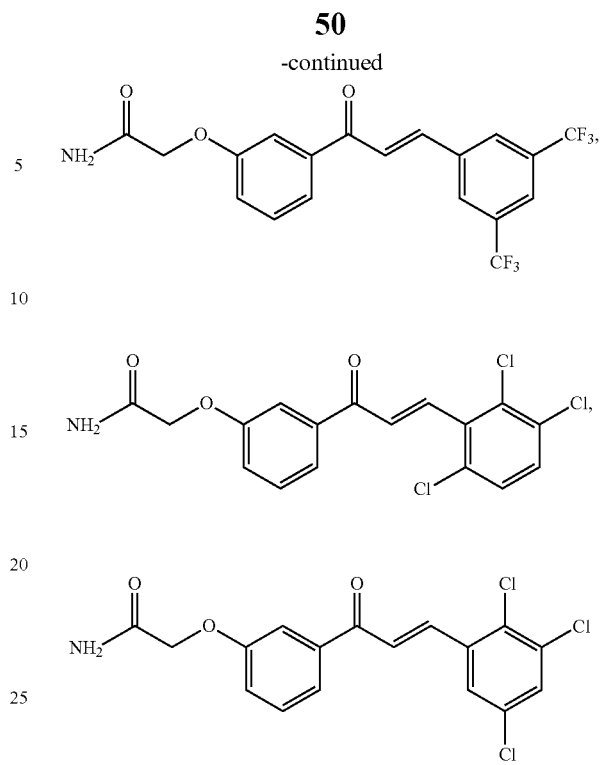

or salts and esters thereof.

28. A pharmaceutical composition which comprises a compound of claim 1 in a therapeutically effective amount for inhibition of an infectious agent and a pharmaceutically acceptable carrier.

29. A method of treating a bacterial infection in a subject comprising the step of administering a therapeutically effective amount of a compound of claim 1 or a pharmaceutical formulation thereof to said subject in need thereof.

30. A method of inhibiting growth of a microorganism comprising the step of contacting said microorganism with an effective amount of a compound of claim 1 or a pharmaceutical formulation thereof, wherein said microorganism is a bacteria.

31. The method of claim 30 wherein said bacteria are Gram-positive bacteria.

32. The method of claim 30 wherein said bacteria are selected from the group consisting of *Bacillus, Listeria, Staphylococcus, Streptococcus, Enterococcus, Corynebacterium, Propionibacterium* and *Clostridium*.

33. The method of claim 30 wherein said bacteria are selected from the group consisting of: *S. aureus, S. epidermidis,* and *B. subtilis*.

* * * * *